(12) United States Patent
Reb et al.

(10) Patent No.: US 9,439,861 B2
(45) Date of Patent: Sep. 13, 2016

(54) MICROSPHERES USEFUL FOR THERAPEUTIC VASCULAR EMBOLIZATION

(71) Applicant: Biosphere Medical, SA, South Jordan, UT (US)

(72) Inventors: Philippe Reb, Themericourt (FR); Marion Pierre, Neuilly Plaisance (FR); Barbara De Gioannis, Liancourt (FR); James Krom, Belmont, MA (US)

(73) Assignee: Biosphere Medical, SA, South Jordan, UT (US)

( * ) Notice: Subject to any disclaimer, the term of this patent is extended or adjusted under 35 U.S.C. 154(b) by 413 days.

(21) Appl. No.: 13/890,038

(22) Filed: May 8, 2013

(65) Prior Publication Data

US 2013/0252900 A1    Sep. 26, 2013

Related U.S. Application Data

(62) Division of application No. 13/014,172, filed on Jan. 26, 2011, now abandoned.

(60) Provisional application No. 61/460,742, filed on Jan. 27, 2010.

(30) Foreign Application Priority Data

Jan. 27, 2010  (EP) .................................. 10305093

(51) Int. Cl.
  *A61K 9/16*   (2006.01)
  *A61L 24/06*  (2006.01)
  (Continued)

(52) U.S. Cl.
  CPC .............. *A61K 9/16* (2013.01); *A61K 9/1682* (2013.01); *A61K 38/39* (2013.01); *A61L 24/06* (2013.01);
  (Continued)

(58) Field of Classification Search
  None
  See application file for complete search history.

(56) References Cited

U.S. PATENT DOCUMENTS 3,003,986 A * 10/1961 Long ..................... B01J 19/18
                                              422/135
3,797,485 A    3/1974  Urquhart
(Continued)

FOREIGN PATENT DOCUMENTS

EP    1195389 A1   4/2002
EP    1656957      5/2005
(Continued)

OTHER PUBLICATIONS

Boschetti, 'Polyacrylamide Derivatives to the Service of Bioseparations', Journal of Biochemical and Biophysical Methods 19: 21-36, 1989.
(Continued)

*Primary Examiner* — Isaac Shomer
(74) *Attorney, Agent, or Firm* — Stoel Rives LLP

(57) ABSTRACT

Provided herein, for example, are microspheres comprising a gelatin or gelatin substitute and a copolymer of a N-tris-hydroxymethyl methylacrylamide monomer unit, a diethylaminoethylacrylamide monomer unit and a N,N-methylene-bis-acrylamide monomer unit. Also provided are methods of producing microspheres comprising a gelatin or gelatin substitute and a copolymer of a N-tris-hydroxymethyl methylacrylamide monomer unit, a diethylaminoethylacrylamide monomer unit and a N,N-methylene-bis-acrylamide monomer unit. Further provided herein, for example, are compositions comprising the microspheres and methods of using the microspheres and compositions thereof.

24 Claims, 21 Drawing Sheets

(51) Int. Cl.
| | |
|---|---|
| C08F 2/44 | (2006.01) |
| C08J 3/24 | (2006.01) |
| C08L 33/26 | (2006.01) |
| C08F 220/54 | (2006.01) |
| A61K 38/39 | (2006.01) |
| A61B 6/00 | (2006.01) |

(52) U.S. Cl.
CPC ............ *C08F 2/44* (2013.01); *C08F 220/54* (2013.01); *C08J 3/246* (2013.01); *C08L 33/26* (2013.01); *A61B 6/504* (2013.01); *A61L 2430/36* (2013.01); *C08J 2333/26* (2013.01); *C08J 2389/00* (2013.01)

(56) References Cited

U.S. PATENT DOCUMENTS

| | | | |
|---|---|---|---|
| 4,413,070 | A | 11/1983 | Rembaum |
| 4,480,078 | A * | 10/1984 | Gujarathi ............... C08F 2/22 523/201 |
| 4,536,387 | A | 8/1985 | Sakamoto et al. |
| 4,622,362 | A | 11/1986 | Rembaum |
| 4,801,458 | A | 1/1989 | Hidaka et al. |
| 4,990,340 | A | 2/1991 | Hidaka et al. |
| 5,281,968 | A | 1/1994 | Iwanaga |
| 5,635,215 | A | 6/1997 | Boschetti et al. |
| 2002/0103331 | A1 | 8/2002 | Zeh et al. |
| 2004/0002169 | A1* | 1/2004 | Kraus, Jr. ............... B03C 1/00 436/526 |
| 2004/0096662 | A1 | 5/2004 | Lanphere et al. |
| 2006/0144339 | A1* | 7/2006 | Walker ............... A01K 5/0291 119/51.5 |

FOREIGN PATENT DOCUMENTS

| | | |
|---|---|---|
| JP | 60215365 | 10/1985 |
| JP | 6020934 | 1/1994 |
| JP | 6508139 | 9/1994 |
| JP | 2001294603 | 10/2001 |
| JP | 2002155104 A | 5/2002 |
| JP | 2003534406 A | 11/2003 |
| JP | 2004115694 B2 | 4/2004 |
| WO | WO9206702 | 4/1992 |
| WO | 9221327 | 12/1992 |
| WO | WO 9221327 A1 * | 12/1992 ............... A61K 9/16 |
| WO | WO9612510 | 5/1996 |
| WO | WO9944643 | 9/1999 |
| WO | WO0170289 | 9/2001 |
| WO | 0172281 | 10/2001 |
| WO | 0189501 | 11/2001 |

OTHER PUBLICATIONS

Laurent et al., 'Etude Histologique de Plusieurs Materiaux D'Embolisation et d'un Nouveau Type de Material Spherique et Adhesif', Innovation et Technologie en Hiplogie et Medicine 10(3): 357-366, 1989.

Mazza et al., 'Polymer Design in Dye Chromatography: Polymeric Supports', in Protein-Sye Interactions: Developments and Applications, Vijayalaksnmi M.A. et., Elsiver Appl. Sciences, Elsevier Sci. Publ. Ltd. pp. 126-136, 1989.

Brown et al., 'Syntheses and Copolymerizations of New Water-Soluble Polyiodinated Acrylic Monomers', Makromol. Chem., Rapid Commun. 6: 503-57, 1985.

Obrenovitch et al., 'Microcarrier Culture of Fibroblastic Cells on Modified Trisacryl Beads', Biol. Cell 46: 249-256, 1982.

Thanoo et al., 'Barium Sulphate-Loaded p(HEMA) Microspheres as Artificial Emboli: Preparation and Properties', Biomaterials, vol. 11 No. 7, pp. 477-481, 1990.

Horak et al., 'Hydrogels in Endovascular Embolization', Biomaterials, vol. 9 No. 4, pp. 367-371, 1988.

Horak et al., 'Hydrogels in Endocascular Embolization III: Radiopaque Shoerical Paricles, Their Preparation and Properties', Biomaterials, vol. 8 No. 2, pp. 142-145, 1987.

Beaujeux et al., 'Trisacryl Gelatin Microspheres for Therapeutic Embolization II: Preliminary Clinical Evaluation in Tumors and Arteriovenous Malformations', AJNR, vol. 17 No. 3, pp. 541-548, 1996.

Laurent et al., 'Trisacryl Gelatin Microspheres for Therapeutic Embolization I: Development and in Vitro Evaluation,' AJNR vol. 17 No. 3, pp. 533-540, 1996.

Notice of Allowance dated Dec. 23, 1996 for U.S. Appl. No. 08/471,303.

Office Action dated May 7, 1996 for U.S. Appl. No. 08/471,303.

Office Action dated Oct. 16, 1995 for U.S. Appl. No. 08/471,303.

Response to Restriction Requirement dated Jul. 24, 2012 for U.S. Appl. No. 13/014,172.

European Search Report dated Mar. 13, 2015 for ER10305093.6.

International Search Report dated Sep. 19, 1992 for PCT/US1992/04265.

International Search Report dated Jan. 26, 2011 for PCT/EP2011/051059.

International Search Report dated Sep. 16, 1992 for PCT/US92/04265.

* cited by examiner

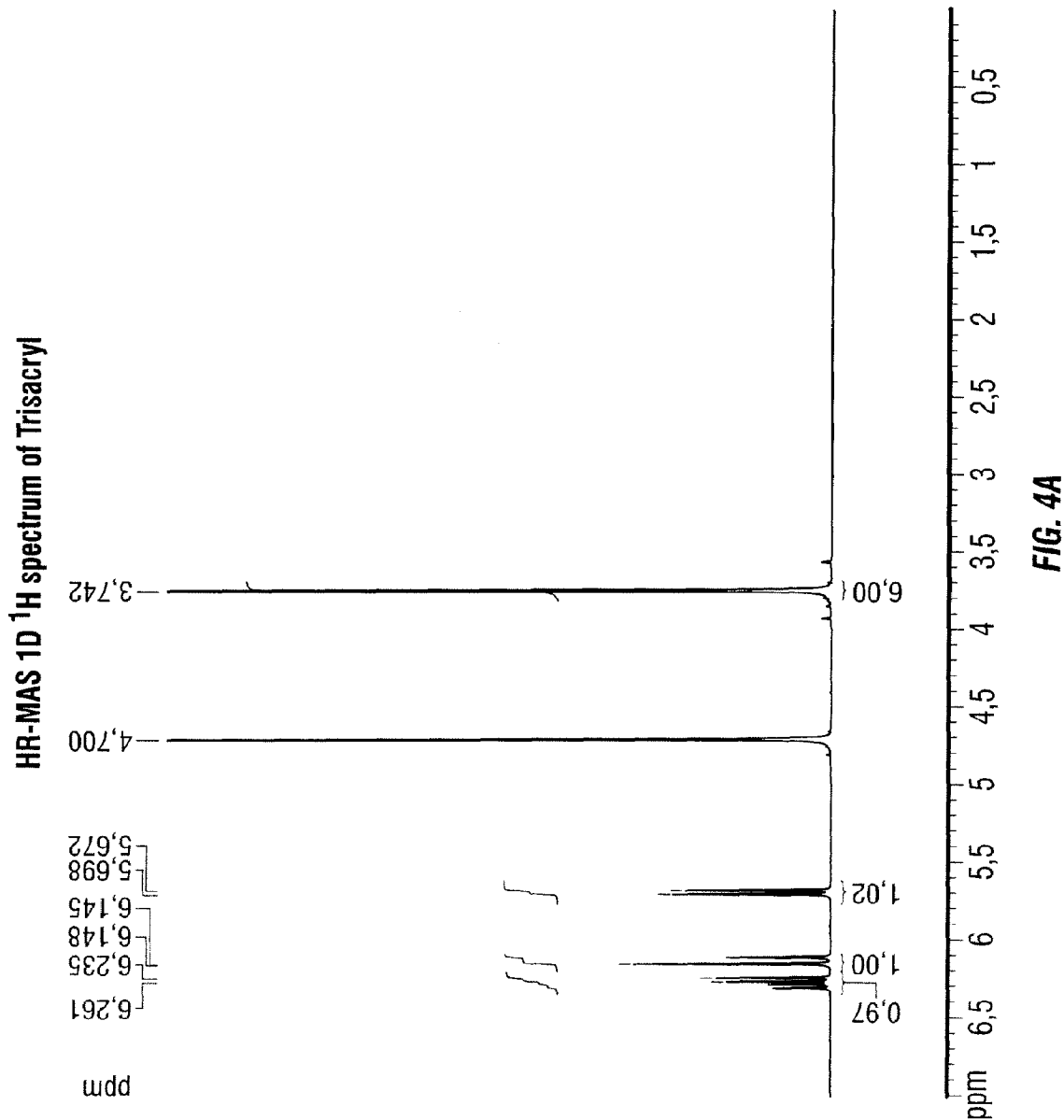

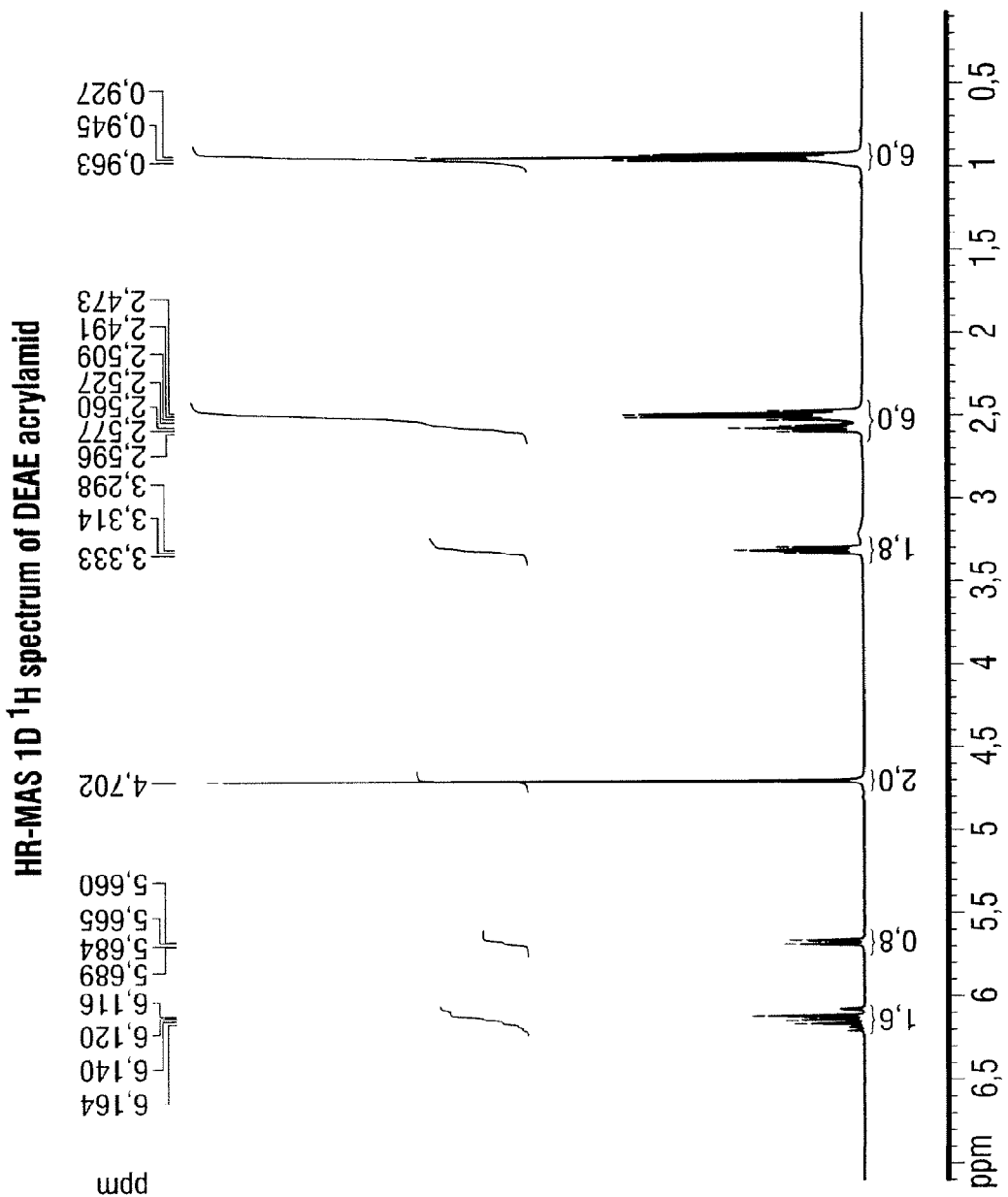

| N° atom | δ (ppm) in D$_2$O |
|---|---|
| | $^1$H |
| 1 | 6.26-6.14 |
| 2 | 5.69 |
| 7,8,9 | 3.65 |

| N° atom | δ (ppm) in D$_2$O |
|---|---|
| | $^1$H |
| 1,11 | 6.16 |
| 2,9 | 5.71 |
| 6 | 4.65 |

| N° atom | δ (ppm) in D₂O |
|---|---|
| | ¹H |
| 1 | 6.14 |
| 2 | 5.68 |
| 6 | 3.31 |
| 7 | 2.58 |
| 9,10 | 2.49 |
| 11,12 | 0.94 |

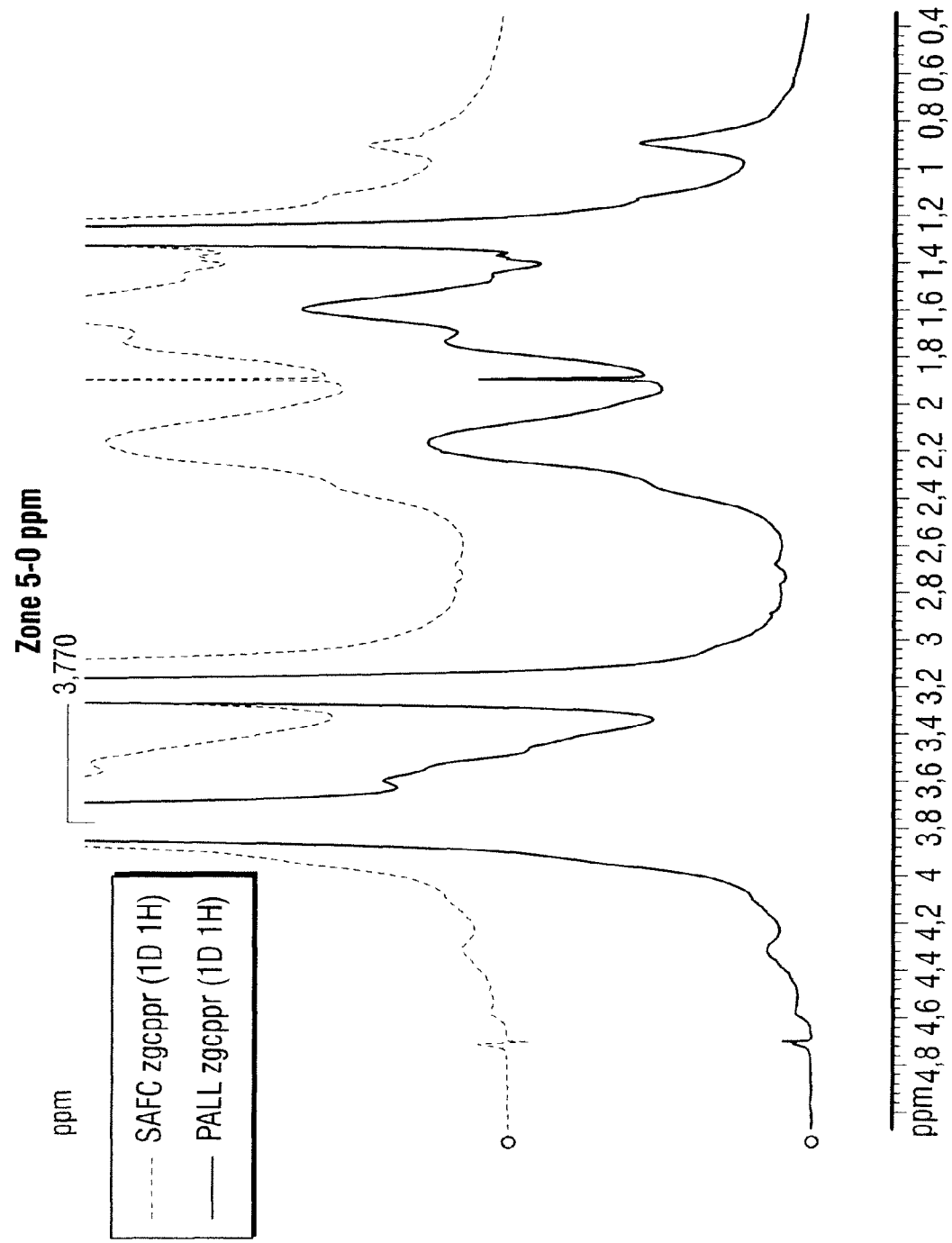

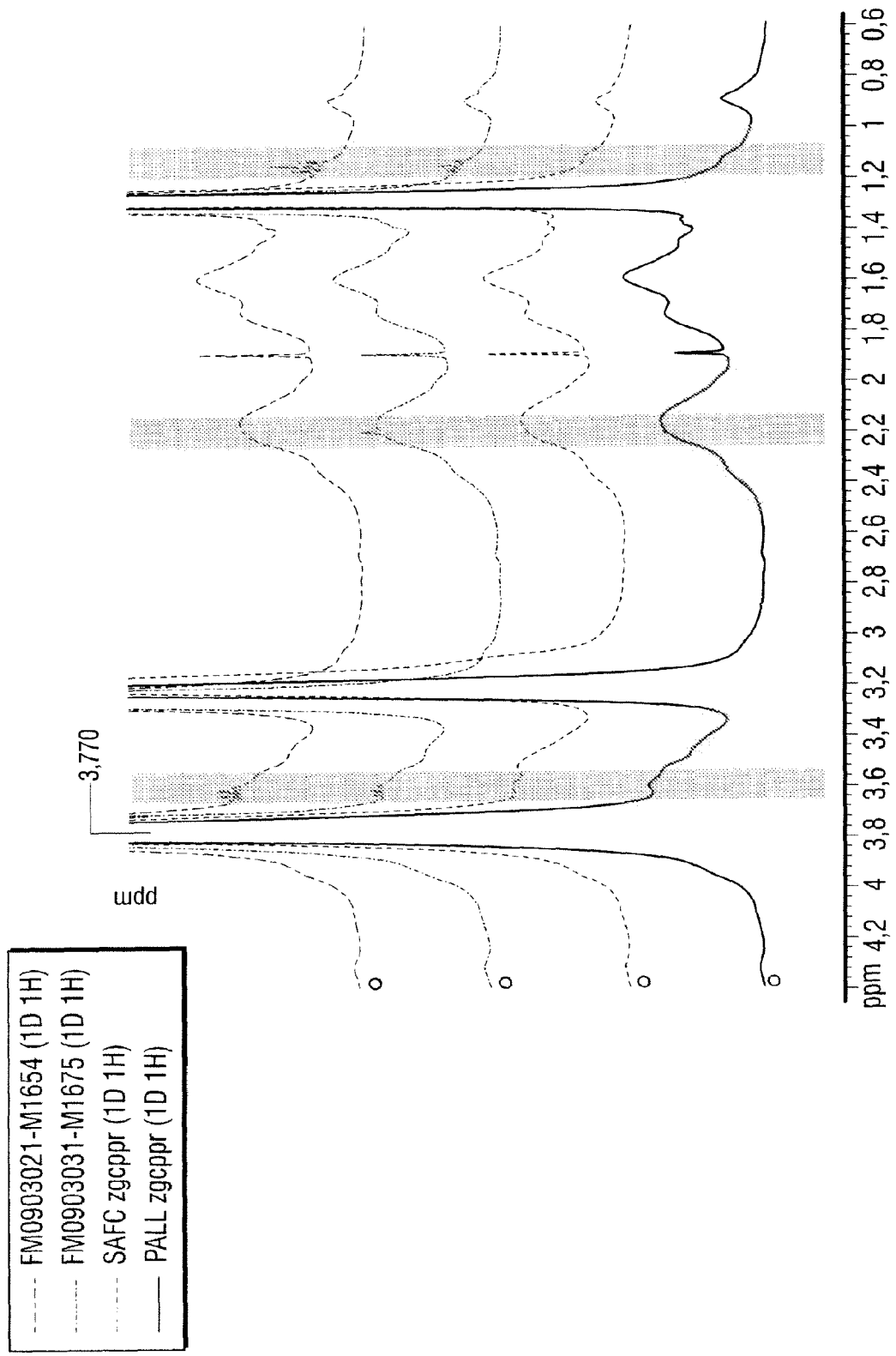

MICROSPHERES USEFUL FOR THERAPEUTIC VASCULAR EMBOLIZATION

CROSS-REFERENCE TO RELATED APPLICATIONS

This patent application is a divisional of U.S. patent application Ser. No. 13/014,172, entitled MICROSPHERES USEFUL FOR THERAPEUTIC VASCULAR EMBOLIZATION, filed on Jan. 26, 2011, which claims priority to U.S. Ser. No. 61/460,742 filed on Jan. 27, 2010, and EP Serial No. 10305093.6 filed on Jan. 27, 2010, each of which is incorporated herein by reference in its entirety.

FIELD

Provided herein, for example, are microspheres comprising a gelatin or gelatin substitute and a copolymer of a N-tris-hydroxymethyl methylacrylamide monomer unit, a diethylaminoethylacrylamide monomer unit and a N,N-methylene-bis-acrylamide monomer unit. Also provided are methods of producing microspheres comprising a gelatin or gelatin substitute and a copolymer of a N-tris-hydroxymethyl methylacrylamide monomer unit, a diethylaminoethylacrylamide monomer unit and a N,N-methylene-bis-acrylamide monomer unit. Further provided herein, for example, are compositions comprising the microspheres and methods of using the microspheres and compositions thereof.

BACKGROUND

Therapeutic vascular occlusion (i.e., embolization) is used to prevent or treat certain pathological conditions in situ. It can be administered by means of catheters making it possible, under imagery control, to position particulate occlusion agents (i.e., emboli) in the circulatory system. It has a variety of medical applications such as in the treatment of tumors, including, e.g., uterine fibroids, vascular malformations and hemorrhagic processes. For example, vascular occlusion can suppress pain, limit blood loss on the surgical intervention to follow embolization or even bring on a tumoral necrosis and avoid the operation. In the case of vascular malformations, vascular occlusion enables the blood flow to the normal tissues to be normalized, aids in surgery and limits the risk of hemorrhage. In the hemorrhagic processes, vascular occlusion can produce a reduction of flow, which promotes cicatrisation of the arterial opening(s). Moreover, depending on the pathological conditions treated, embolization can be used for temporary as well as permanent purposes.

Different types of emboli have been used for embolization, for example, liquid agents (e.g., acrylic glues, gels or viscous suspensions) as well as particulate agents (e.g., miscellaneous polymers, dura mater, gelatin sponges, spheres, balloons or spirals), including EmboSphere® trisacryl gelatin microspheres (BioSphere Medical, Rockland, Mass.) (see also, e.g., U.S. Pat. Nos. 5,635,215 and 5,648,100).

Among the various occlusion agents, microspheres have demonstrated better embolic properties over other solid emboli. However, the quality and yield of the microspheres often varies due to materials used in the production process and methods of making them.

Accordingly, there remains a need for methods of producing microspheres with, e.g., a better yield productivity and possibly better uniformity or purity. In addition, there also remains a need for microspheres with, for example, a better or more consistent quality from production batch to production batch that are capable of providing optimized embolic effects.

SUMMARY

The methods provided herein relate generally to microspheres and compositions comprising the microspheres. Also provided herein are methods of producing and using the microspheres.

Provided herein, in one aspect, is a microsphere comprising: (a) a copolymer comprising a N-tris-hydroxymethyl methylacrylamide monomer unit, a diethylaminoethylacrylamide monomer unit and a N,N-methylene-bis-acrylamide monomer unit, and (b) crosslinked gelatin. In certain embodiments, the microsphere exhibits in a $^1$H NMR spectrum, a first peak from about 3.5 ppm to about 4 ppm, a second peak from about 3 ppm to about 3.5 ppm, and a third peak from about 1 ppm to about 1.5 ppm. In specific embodiments, (i) the integration ratio of the second peak to the first peak is about 0.50 to about 0.65, (ii) the integration ratio of the third peak to the first peak is about 0.55 to about 0.75 (e.g., about 0.61 to about 0.75), or (iii) a combination of (i) and (ii). In certain embodiments, the N-tris-hydroxymethyl methylacrylamide monomer unit is an ultra-pure monomer unit, the diethylaminoethylacrylamide monomer is an ultra-pure monomer unit and/or the N,N-methylene-bis-acrylamide monomer unit is an ultra-pure monomer.

In another aspect, provided herein is a microsphere comprising: (a) a copolymer prepared by copolymerizing a N-tris-hydroxymethyl methylacrylamide monomer, a diethylaminoethylacrylamide monomer and a N,N-methylene-bis-acrylamide monomer, and (b) crosslinked gelatin. In certain embodiments, the microsphere exhibits in a $^1$H NMR spectrum, a first peak from about 3.5 ppm to about 4 ppm, a second peak from about 3 ppm to about 3.5 ppm, and a third peak from about 1 ppm to about 1.5 ppm. In specific embodiments, (i) the integration ratio of the second peak to the first peak is about 0.50 to about 0.65, (ii) the integration ratio of the third peak to the first peak is about 0.55 to about 0.75 (e.g., about 0.61 to about 0.75), or (iii) a combination of (i) and (ii). In certain embodiments, the N-tris-hydroxymethyl methylacrylamide monomer is an ultra-pure monomer, the diethylaminoethylacrylamide monomer is an ultra-pure monomer and/or the N,N-methylene-bis-acrylamide monomer is an ultra-pure monomer.

In another aspect, provided herein is a method of making microspheres comprising: (a) preparing an aqueous solution comprising (i) a N-tris-hydroxymethyl methylacrylamide monomer, (ii) a diethylaminoethylacrylamide monomer, (iii) a N,N-methylene-bis-acrylamide monomer, and (iv) gelatin, wherein the N-tris-hydroxymethyl methylacrylamide monomer is an ultra-pure monomer, the diethylaminoethylacrylamide monomer is an ultra-pure monomer and/or the N,N-methylene-bis-acrylamide monomer is an ultra-pure monomer; (b) adding the aqueous solution to a liquid organic phase (e.g., an oil, such as a mineral oil, such as a paraffin oil) that has low miscibility in water, before or while stirring; thereby producing microspheres comprising a copolymer comprising N-tris-hydroxymethyl methylacrylamide, diethylaminoethylacrylamide and N,N-methylene-bis-acrylamide monomer units; (c) crosslinking the gelatin. In some embodiments, the method further comprises subjecting the microspheres to sonication (e.g., ultrasonication) prior to crosslinking the gelatin. In one embodiment, the aqueous solution is added through a feed ring to the liquid organic phase. Also provided herein are microspheres produced by these methods.

In a another aspect, provided herein are methods of embolization in a subject, comprising administering to the subject the microsphere(s) provided herein.

In yet another aspect, provided herein are methods of managing or treating an angiogenesis-dependent disease in a subject, comprising administering to the subject the microsphere(s) provided herein.

TERMINOLOGY

Unless defined otherwise, all technical and scientific terms used herein have the same meaning as is commonly understood by one of ordinary skill in the art. All patents, applications, published applications and other publications are incorporated herein by reference in their entirety. In the event that there is a plurality of definitions for a term herein, those in this section prevail unless stated otherwise.

The term "about" or "approximately" means within 20%, such as within 15%, within 10%, within 9%, within 8%, within 7%, within 6%, within 5%, within 4%, within 3%, within 2%, within 1%, within 0.5% or less of a given value or range.

As used herein, "administer," "administration" and "administering" refers to the act of injecting or otherwise physically delivering a substance as it exists outside the body (e.g., a particle or microsphere provided herein) into a patient, such as by, but not limited to, pulmonary (e.g., inhalation), mucosal (e.g., intranasal), intradermal, intravenous, intraarterial, intrabiliary, intraocular, intraosseous, intramuscular delivery and/or any other method of physical delivery described herein or known in the art. In specific embodiments, the microspheres are delivered using a syringe and/or a catheter. When a disease, or a symptom thereof, is being treated or otherwise managed, administration of the substance typically occurs after the onset of the disease or symptoms thereof. When a disease, or symptom thereof, is being prevented, administration of the substance typically occurs before the onset of the disease or symptoms thereof. Such administration, in certain embodiments, results in the delivered particles (e.g., a microsphere provided herein) contacting the target area (e.g., a blood vessel, tissue or organ).

The term "angiography" refers to a type of x-ray that is done to image blood vessels in various parts of the body (e.g., liver, prostate, uterine), so as to determine whether the vessels are diseased, narrowed, enlarged or blocked altogether. In certain embodiments, an angiogram (e.g., x-ray) is taken by injecting a contrast material to highlight the vessels, after passing a catheter into an artery leading to the body area of interest. "Superselective angiography" refers to angiography with the use of a smaller catheter may be passed through a larger one into a branch artery supplying a small area of tissue or a tumor.

The term "arteriovenous malformation," "AVM," "vascular malformation" refers to a group of diseases wherein at least one (and most typically, many) abnormal communications between arteries and veins occur, resulting in a local tumor-like mass composed predominantly of blood vessels. Such disease may be either congenital or acquired.

The term "benign prostatic hyperplasia" refers to the increase in size of the prostate, for example, in middle-aged and elderly men.

As used herein, "crosslink," "crosslinked" and "crosslinking" generally refer to the linking of two or more stabilizing materials, including lipid, protein, polymer, carbohydrate, surfactant stabilizing materials, bioactive therapeutic factor and/or bioactive agents, by one or more bridges. The bridges may be composed of one or more elements, groups, or compounds, and generally serve to join an atom from a first stabilizing material molecule to an atom of a second stabilizing material molecule. The crosslink bridges may involve covalent and/or non-covalent associations. Any of a variety of elements, groups, and/or compounds may form the bridges in the crosslinks, and the stabilizing materials may be crosslinked naturally or through synthetic means. For example, crosslinking may occur in nature in material formulated from peptide chains which are joined by disulfide bonds of cystine residues, as in keratins, insulins and other proteins. Alternatively, crosslinking may be effected by suitable chemical modification, such as, for example, by combining a compound, such as a stabilizing material, and a chemical substance that may serve as a crosslinking agent, which may cause to react by, for example, exposure to heat, high-energy radiation, and the like. Examples include crosslinking by sulfur to form disulfide linkages, crosslinking using organic peroxides, crosslinking of unsaturated materials by means of high-energy radiation, crosslinking with dimethylol carbamate, and the like. In certain embodiments of the microspheres provided herein, the gelatin is crosslinked.

The term "cell adhesion promoter" as used herein means any material that, because of their presence in or association with the microspheres, promotes or enhances the adhesiveness of cells to the surface of the microspheres. These materials are often proteins that are bound to the surface of the microspheres through covalent bonds of the proteins and the polymers.

As used herein, "chemical modification" refers to the changes of chemical properties and characteristics of the microspheres, either during their production process or by way of mixing or contacting them with various agents or tissues, such that the microspheres have the ability to perform, in addition to embolization, other functions, for example, once injected into the body.

The term "effective amount" as used herein refers to the amount of a therapy (e.g., a microsphere or composition provided herein) which is sufficient to partially or completely occlude a blood vessel, such as an artery or vein. Such occlusion may be temporary or permanent. In certain embodiments, the effective amount will further ameliorate the severity and/or duration of a given disease and/or a symptom related thereto. In certain embodiments of the methods provided herein, an effective amount of the microspheres is administered to the patient.

The term "embolization" or "therapeutic embolization" as used herein refers to a partial or total occlusion of vessels where the blood is flushing, for example, selective occlusion of blood vessels by purposely introducing emboli into the vessels. For example, embolization allows occlusion of arteries or veins either to correct a dysfunction (e.g., an arteriovenous malformation) or to stop or slow the blood flow (e.g., to a solid tumor/cancer growth). In certain embodiments, embolization is a passive operation in the sense that no active molecules are carried and/or delivered where the embolic material is deposited.

The term "in combination" as used herein in the context of the administration of other therapies refers to the use of more than one therapy. The use of the term "in combination" does not restrict the order in which therapies are administered to a subject. A first therapy can be administered before (e.g., 1 minute, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject, for example, which had, has, or is susceptible to a given disease. Any additional therapy can be administered in any order with the other additional therapies. In certain embodiments, the particles provided herein can be administered in combination with one or more therapies (e.g., therapies that are not microspheres that are currently administered to prevent, treat, manage, and/or ameliorate a given disease or other symptom related thereto). Non-limiting examples of therapies that can be administered in combination with the particles provided herein include analgesic agents, anesthetic agents, antibiotics, or immunomodulatory agents or any other agent listed in the *U.S. Pharmacopoeia—National Formulary* (2009) U.S. Pharmacopoeia, including revisions, and/or *Physician's Desk Reference* (2009) 63$^{rd}$ ed., Thomson Reuters.

As used herein, the term "impurity" or "impurities" refers to substances present in a confined amount of material or compound (e.g., a monomer or monomer unit), which differ from the chemical composition of the material or compound. Impurities can be naturally occurring or added during or resulting from the synthesis of a material or compound.

As used herein, "injectable" means capable of being administered, delivered or carried into the body via syringe, catheters, needles or other means for injecting or infusing the microspheres in a liquid medium. In certain embodiments, the particles provided herein are injectable particles.

As used herein, a liquid or solution that has "low miscibility in water" refers to a liquid or solution having about 50% or less, about 40% or less, about 35% or less, about 30% or less, about 25% or less, about 20% or less, about 15% or less, about 10% or less, about 5% or less, about 4% or less, about 3% or less, about 2% or less, about 1% or less, about 0.5%, about 0.1% or less, or about 0% miscibility in water at 25° C. In a specific embodiment, the liquid or solution has about 5% or less miscibility in water at 25° C. In another specific embodiment, the liquid or solution has about 1% or less miscibility in water at 25° C. In some embodiments, the liquid or solution is immiscible.

As used herein, the terms "manage," "managing," and "management" refer to the beneficial effects that a subject derives from a therapy (e.g., microspheres provided herein), which does not result in a cure of the disease. In certain embodiments of the methods provided herein, a subject is administered one or more therapies to "manage" a given disease or one or more symptoms related thereto, so as to prevent the progression or worsening of the disease.

As used herein, the term "microspheres" refers to a polymer or one or more combinations of polymers made into bodies of various sizes. The microspheres as used herein can be in any shape. In certain embodiments, the microspheres are substantially spherical shape. These structures of the microspheres may be generally spherical or spheroid in shape or bounded by imaginary spherical or spheroid shapes. In some embodiments, the surfaces of the microspheres provided herein appear smooth under magnification of up to 1000 times, such as up to 100 times, up to 10 times, 0 times or a range thereof. The microspheres may be sterilized by any method known in the art, for example, by irradiation, such as gamma or beta irradiation. The microspheres provided herein may comprise other materials as described and defined herein. However, it will be appreciated, that the term "microsphere" represents a convenient description for the purposes of explanation of the compositions and methods provided herein, and that, in certain embodiments, the exemplary microspheres described herein are not necessarily limited to being precisely spherical in shape (e.g., are particles).

The term "monomer" refers to a small molecule that may become chemically bonded to other monomers to form a polymer or copolymer. Reference to certain properties or characteristics of a monomer herein can also apply to the corresponding monomer unit and vice versa.

The term "monomer unit" refers to a monomer in a polymer or copolymer.

The term "pharmaceutically acceptable" as used herein means being approved by a regulatory agency of the Federal or a state government, or listed in the U.S. Pharmacopeia, European Pharmacopeia or other generally recognized pharmacopeia for use in animals, and more particularly in humans.

As used herein, the terms "prevent," "preventing," and "prevention" refer to the total or partial inhibition of a given disease; the total or partial inhibition of the development or onset of disease progression of given disease, or a symptom related thereto in a subject.

As used herein, the term "side effects" encompasses unwanted and adverse effects of a therapy. Unwanted effects are not necessarily adverse. An adverse effect from a therapy might be harmful or uncomfortable or risky. Examples of side effects include, but are not limited to, rhinitis, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (58$^{th}$ ed., 2004).

The term "sonication" refers to the act of applying sound energy (e.g., ultrasonication) to agitate particles in a sample (e.g., microspheres).

As used herein, "stabilizing material" or "stabilizing compound" refers to any material which is capable of improving the stability of compositions, targeting ligands and/or other bioactive therapeutic factors described herein, including, for example, mixtures, suspensions, emulsions, dispersions, vesicles, or the like.

The term "stem cells" refers to cells that have the capacity to self-renew and to generate differentiated progeny. In certain embodiments, the stem cells are mesenchymal stem cells.

The term "sticking" or "aggregated" refers to the state where an object or article (e.g., a microsphere) is in tight physical contact with one or more objects or articles and is inseparable from other objects or articles without external forces (e.g., gathering into a mass or whole). In certain embodiments, a sticking or aggregated microsphere refers to a microsphere that is in tight physical contact with one or more microspheres, for example, due to the gelatin or a gelatin substitute. The term "unsticking," "non-sticking," "unaggregated" or "non-aggregated" refers to the state free from tight physical contact or adhesion. In certain embodiments, an unsticking, non-sticking, unaggregated or non-aggregated microsphere refers to a microsphere that is substantially free or completely free from tight physical contact with other microspheres. The percentage of sticking microspheres in a population can be determined, for example, by observation under a microscope.

As used herein, the terms "subject" and "patient" are used interchangeably. As used herein, a subject is a mammal such as a non-primate (e.g., cows, pigs, horses, cats, dogs, rats, rabbits, etc.) or a primate (e.g., monkey and human) comprising administration of particles as provided herein. In some embodiments, the patient is in need of treatment or management of the disease or symptom thereof. In specific embodiments, the subject is a human.

As used herein, the term "substantially spherical" or "generally spherical" refers to a shape that is close to a perfect sphere, which is defined as a volume that presents the lowest external surface area. Specifically, "substantially spherical" as used herein means, when viewing any cross-section of the particle (e.g., under a microscope), the difference between the average major diameter and the average minor diameter is less than 20%, less than 15%, less than 10%, less than 5%, or less than 1%. In some embodiments, the surfaces of the microspheres provided herein appear smooth under magnification of up to 1000 times, such as up to 100 times, up to 10 times, 0 times or a range thereof.

The terms "therapeutic agent" or "therapeutic drug" can be used interchangeably herein and refers to any therapeutically active substance that is delivered to a bodily conduit of a living being to produce a desired, usually beneficial, effect.

As used herein, the term "therapy" refers to any protocol, method and/or agent that can be used in the management, treatment and/or amelioration of a given disease, or a symptom related thereto. In certain embodiments, the terms "therapies" and "therapy" refer to a biological therapy, supportive therapy, and/or other therapies known to one of skill in the art, such as medical personnel, useful in the management or treatment of a given disease, or symptom related thereto.

As used herein, the terms "treat," "treatment" and "treating" refer to the reduction or amelioration of the progression, severity, and/or duration of a disease or a symptom thereof.

As used herein, the term "ultra-pure" refers to the state of a compound or material (e.g., monomer or monomer unit) having a very low level of impurities compared to a compound or material (e.g., monomer or monomer unit) that is undiluted or unmixed with extraneous compounds or materials. In certain embodiments, the impurity is a salt. In some embodiments, the level of impurities present in a compound or material can be expressed as a percentage (%); for example, an ultra-pure monomer or an ultra-pure monomer unit can have less than 1%, less than 2%, less than 3%, less than 4%, less than 5%, less than 6%, less than 7%, less than 8%, less than 9%, less than 10%, less than 15%, less than 20%, less than 25% of impurities or any range thereof. In certain embodiments, the level of impurities is determined by the bromine test (see, e.g., Examples 3 and 6). In other embodiments, the level of impurities is determined by HPLC (see e.g., Examples 2 and 5).

The term "uterine fibroid" or "leiomyoma" refers to non-cancerous tumors composed of certain types of muscle fibers and fibrous connective tissue of the uterus.

BRIEF DESCRIPTION OF THE DRAWINGS

FIG. 1A depicts the differences in the sensitivities of purity observed using a bromination reaction (right bars, as provided by manufacturer BioSepra) and HPLC (left bars) for given lots of DEAE monomer (T209, U088 and U089) obtained from BioSepra. FIG. 1B depicts the difference in the sensitivities of purity for two different lots of trisacryl (R426 and R402 obtained from BioSepra) observed using a bromination reaction (right bars) or HPLC (left bars), and the data are shown with an assumption of 100% purity of a recrystallized trisacryl (TA-R) obtained and compared with trisacryl monomer from SAFC prior to recrystallization (TA).

FIG. 2A shows microspheres before crosslinking, initially (left panel) and after 15 min of ultrasonication (right panel). The percentage of sticking microspheres decreases from about 7% to about 0.2% with ultrasonication. FIG. 2B demonstrates microspheres after crosslinking without (left panel) or with (right panel) ultrasonication prior to crosslinking Sieving was done after the ultrasonication step. The percentage of sticking microspheres decreases from about 3% to nearly about 0% with ultrasonication. FIG. 2C shows microspheres before crosslinking, initially (left panel) and after 2×15 min. of ultrasonication (right panel). The percentage of sticking microspheres decreases from about 9.2% to about 1.6% with ultrasonication.

FIGS. 4A-4G illustrate the high resolution magic angle spinning (HR-MAS) one-dimensional (ID) $^1$H spectra of starting materials and microspheres. FIGS. 4A-D illustrate the HR-MAS one-dimensional $^1$H spectra of trisacryl (4A), gelatin (4B), MBA (4C) and DEAE acrylamide (4D). FIG. 4E-4G show the attribution of 1H nuclei of trisacryl (4E), MBA (4F) and DEAE acrylamide (4G).

FIGS. 5A-5J illustrate the one-dimensional $^1$H NMR spectra of microspheres made from materials of different sources. FIGS. 5A-5D illustrate the NMR spectra of samples SAFC FMP 128 and PALL FMP 130. FIG. 5A is the superposition of the NMR spectra showing a similarity between the corresponding main peaks (marked as A, B and C) identified from the spectra. FIG. 5B shows the NMR spectra in the region of 9-5 ppm. FIG. 5C shows the NMR spectra in the region of 5-0 ppm. FIG. 5D shows the NMR spectra in the region of 3.4-1.2 ppm. FIGS. 5E-5J illustrate the NMR spectra of samples SAFC FMP 128, PALL FMP 130, FM0903031-M1675 and FM0903021-M1654. FIG. 5E shows a comparison of the NMR spectra. FIG. 5F shows the NMR spectra of 2.6-1.5 ppm. FIG. 5G shows the spectra in the region of 3.4-1.2 ppm. FIG. 5H shows the NMR spectra in the region of 9-5 ppm. FIG. 5I shows a superposition of the spectra (FIG. 5I). FIG. 5J shows the NMR spectra after deconvolution.

DETAILED DESCRIPTION

Figure 1A:
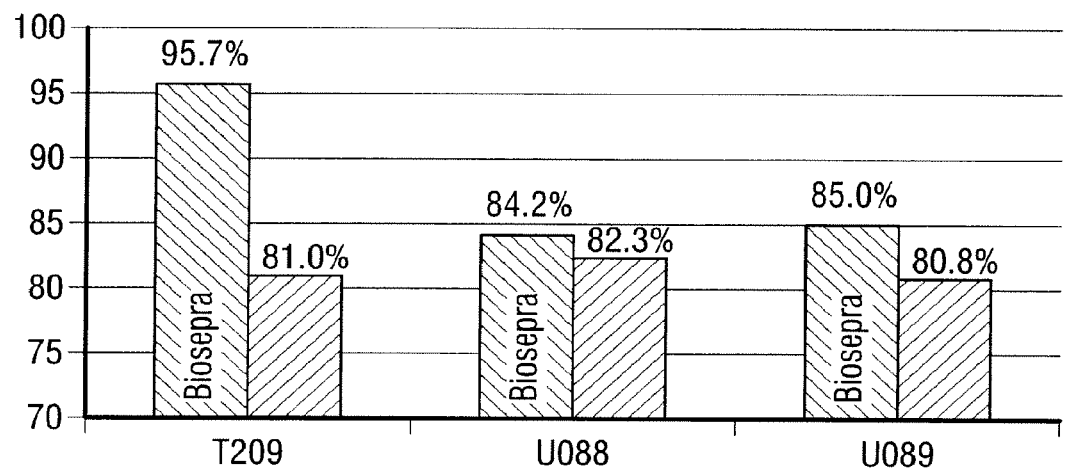
FIGS. 1A-1B illustrate a comparison of the purity of monomers.

The microspheres provided herein are, in certain embodiments, non-toxic to organs, tissues and cells, biocompatible, and adhesive to various cells and tissues at the site of implantation by means of the cell growth they promote. In addition, in certain embodiments, these microspheres are non-resorbable and non-biodegradable, and thus are stable, durable, and will maintain their general shape and position once implanted at a desired site. In further embodiments, the microspheres are also stable in suspension which allows the microspheres or other solid substrates to be formulated and stored in suspension and injected with different liquids.

A. Microspheres for Embolization

In one aspect, provided herein is a microsphere comprising: (a) a copolymer comprising a N-tris-hydroxymethyl methylacrylamide monomer unit, a diethylaminoethylacrylamide monomer unit and a N,N-methylene-bis-acrylamide monomer unit, and (b) a crosslinked gelatin or gelatin substitute. In another aspect, provided herein is a microsphere comprising (a) a copolymer prepared by copolymerizing a N-tris-hydroxymethyl methylacrylamide monomer, a diethylaminoethylacrylamide monomer and a N,N-methylene-bis-acrylamide monomer, and (b) a crosslinked gelatin or gelatin substitute. In specific embodiments, one, two or all three of the N-tris-hydroxymethyl methylacrylamide, diethylaminoethylacrylamide and a N,N-methylene-bis-acrylamide monomers (or monomer units) are ultra-pure monomers (or monomer units). In certain embodiments, the microsphere exhibits in a $^1$H NMR spectrum, a first peak (e.g., from about 3.5 ppm to about 4 ppm), a second peak (e.g., from about 3 ppm to about 3.5 ppm), and a third peak (e.g., from about 1 ppm to about 1.5 ppm). In specific embodiments, the integration ratio of the second peak to the first peak is from about 0.50 to about 0.65 and/or the integration ratio of the third peak to the first peak is from about 0.55 to about 0.75 (e.g., about 0.61 to about 0.75).

In one embodiment, the microsphere comprises: (a) a copolymer comprising a N-tris-hydroxymethyl methylacrylamide monomer unit, a diethylaminoethylacrylamide monomer unit and a N,N-methylene-bis-acrylamide monomer unit, and (b) crosslinked gelatin; wherein the microsphere exhibits in a $^1$H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is about 0.50 to about 0.65, (ii) the integration ratio of the third peak to the first peak is about 0.55 to about 0.75 (e.g., about 0.61 to about 0.75), or (iii) a combination of (i) and (ii). In another embodiment, the microsphere comprises (a) a copolymer prepared by copolymerizing a N-tris-hydroxymethyl methylacrylamide monomer, a diethylaminoethylacrylamide monomer and a N,N-methylene-bis-acrylamide monomer, and (b) crosslinked gelatin; wherein the microsphere exhibits in a $^1$H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is about 0.50 to about 0.65, (ii) the integration ratio of the third peak to the first peak is about 0.55 to about 0.75 (e.g., about 0.61 to about 0.75), or (iii) a combination of (i) and (ii). In certain embodiments, the first peak is at about 3.77 ppm, the second peak is at about 3.2 ppm, the third peak is at about 1.3 ppm, or a combination thereof. In other embodiments, the integration ratio of the second peak to the first peak is about 0.574, or wherein the integration ratio of the third peak to the first peak is about 0.625. In some embodiments, the microsphere is at 25° C. and/or in a deuterated solvent when the $^1$H NMR spectrum is recorded (e.g., at 400 MHz).

In some embodiments, one or more of the monomers (or monomer units) is an ultra-pure monomer (or monomer units). In certain embodiments, the N-tris-hydroxymethyl methylacrylamide monomer, the diethylaminoethylacrylamide monomer and/or the N,N-methylene-bis-acrylamide monomer are each ultra-pure monomers. In specific embodiments, the N-tris-hydroxymethyl methylacrylamide monomer comprises less than 9% of impurities and/or the diethylaminoethylacrylamide monomer comprises less than 2% of impurities (e.g., as determined by HPLC (see, e.g., Examples 2 and 5) or by a bromine test (see, e.g., Examples 3 and 6). In certain embodiments, the N-tris-hydroxymethyl methylacrylamide monomer, the diethylaminoethylacrylamide monomer and the N,N-methylene-bis-acrylamide monomer are each ultra-pure monomers. In one embodiment, the N-tris-hydroxymethyl methylacrylamide monomer is an ultra-pure monomer, while the diethylaminoethylacrylamide monomer and N,N-methylene-bis-acrylamide monomer are not ultra-pure monomers. In another embodiment, the N-tris-hydroxymethyl methylacrylamide monomer and the diethylaminoethylacrylamide monomer are each ultra-pure monomers, while the N,N-methylene-bis-acrylamide monomer is not an ultra-pure monomer. In some embodiments, the N-tris-hydroxymethyl methylacrylamide monomer and the N,N-methylene-bis-acrylamide monomer are each ultra-pure monomers, while the diethylaminoethylacrylamide monomer is not an ultra-pure monomer. In one embodiment, the diethylaminoethylacrylamide monomer is an ultra-pure monomer, while the N-tris-hydroxymethyl methylacrylamide monomer and the N,N-methylene-bis-acrylamide monomer are not ultra-pure monomers. In another embodiment, the diethylaminoethylacrylamide monomer and the N,N-methylene-bis-acrylamide monomer are each ultra-pure monomers, while the N-tris-hydroxymethyl methylacrylamide is not an ultra-pure monomer. In one embodiment, the N,N-methylene-bis-acrylamide monomer is an ultra-pure monomer, while the N-tris-hydroxymethyl methylacrylamide monomer and the diethylaminoethylacrylamide monomer are not ultra-pure monomers. In another embodiment, the diethylaminoethylacrylamide monomer is an ultra-pure monomer while the N-tris-hydroxymethyl methylacrylamide monomer is not. In yet another embodiment, both the N-tris-hydroxymethyl methylacrylamide and diethylaminoethylacrylamide monomers are ultra-pure monomers. In further embodiments, the hydrophobicity or ionic character of these monomers can be modified as deemed necessary by introducing for example, without limitation, hydrocarbon chains and/or hydrophilic ionizable chemical groups, which can, for example, be used to facilitate drug-loading characteristics of the microsphere (e.g., ionic interactions between the copolymer and the drug). For example, in certain embodiments, the monomer or polymer is modified to add acidic functional groups (e.g., addition of sodium acrylate or vinyl sulfonate to monomer mixture), which can, for example interact with amine functions in a given drug (e.g., doxorubicin or other anthracyclines). In a specific embodiment, monomer is modified with sulfonate groups. the In some embodiments, the monomer has a moisture content of from about 5% to about 0%, such as 5% or less, 4% or less, 3% or less, 2% or less or 1% or less. Moisture content can be determined using methods known in the art, such as NMR analysis.

In some embodiments, the gelatin is crosslinked, for example, to or within the copolymer of the microsphere. In other embodiments, the gelatin is not crosslinked. The gelatin as used herein can be from any source. Exemplary sources include, but are not limited to, collagens extracted from bones, connective tissues, organs and some intestines of cattle, pigs, and horses. In a specific embodiment, the gelatin is a porcine gelatin. In specific embodiments, the gelatin is pharmaceutical and/or food grade gelatin, which can be obtained from commercial suppliers, such as PB Leiner (Vilvoorde, Belgium).

In a second aspect, provided herein are microspheres prepared by a process comprising: (a) preparing an aqueous solution comprising (i) a N-tris-hydroxymethyl methylacrylamide monomer, (ii) a diethylaminoethylacrylamide monomer, (iii) a N,N-methylene-bis-acrylamide monomer, and (iv) gelatin, wherein the N-tris-hydroxymethyl methylacrylamide monomer, the diethylaminoethylacrylamide monomer and/or the N,N-methylene-bis-acrylamide monomer is an ultra-pure monomer; (b) adding the aqueous solution to a liquid organic phase (e.g., an oil, such as a mineral oil, such as a paraffin oil) that has low miscibility in water, before or while stirring; thereby producing microspheres comprising a copolymer comprising N-tris-hydroxymethyl methylacrylamide, diethylaminoethylacrylamide and N,N-methylene-bis-acrylamide monomer units; (c) optionally subjecting the microspheres to sonication (e.g., ultrasonication); and (d) crosslinking the gelatin. Embodiments of the process are described in Section C below.

Microspheres provided herein can have any shape. In specific embodiments, these microspheres are substantially spherical in shape. In certain embodiments, the microspheres are uniform shape.

In certain embodiments, the microspheres provided are calibrated to a certain size range. Such calibration can be achieved using method known in the art, such as by one or more rounds of sieving using an appropriately sized mesh sieve.

In certain embodiments, the microspheres provided herein have a diameter from about 1 μm to 2000 μm, such as from about 10 μm to 1000 μm, from about 40 μm to about 120 μm, from about 100 μm to about 300 μm, from about 300 μm to about 500 μm, from about 500 μm to about 700 μm, from about 700 μm to about 900 μm, or from about 900 μm to about 1200 μm. These diameters can permit the microspheres to be delivered to target blood vessels, tissues or organs in vivo via catheter, needle (e.g., a 18 gauge or smaller needle), tubing, or the like by various pathways including vascular, intraductal, transesophogeal, subcutaneous, subdermal, submucosal, transbronchial, or interstitial. In certain embodiments, the microspheres can be eliminated through macrophages or other elements of the immune system or the lymphatic system.

In certain embodiments, the microspheres are uniform in size. In certain embodiments, the microspheres are uniform in size, wherein the difference in diameter between individual microspheres is from about 0 μm to about 100 μm, from about 0 μm to about 50 μm, or from about 0 μm to about 25 μm, such as 100 μm or less, about 50 μm or less, about 25 mm or less, about 10 mm or less or about 5 μm or less.

In certain embodiments, the microspheres are in a population wherein greater than 68% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 70% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 75% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 80% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 85% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 90% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof. In one embodiment, the microspheres are in a population wherein greater than 95% have a diameter of ±20% of the mean diameter, ±10% of the mean diameter, ±15% of the mean diameter, ±10% of the mean diameter, ±9% of the mean diameter, ±8% of the mean diameter, ±7% of the mean diameter, ±6% of the mean diameter, ±5% of the mean diameter, ±4% of the mean diameter, ±3% of the mean diameter, ±2% of the mean diameter, or ±1% of the mean diameter, or any range thereof.

In some embodiments, less than 1%, less than 0.9%, less than 0.8%, less than 0.7%, less than 0.6%, less than 0.5%, less than 0.4%, less than 0.3% or less than 0.2%, less than 0.1% or 0% (or a range thereof) of microspheres in a population are outside of a given extended range (e.g., ±50 μm±100 μm, ±150 μm, ±200 μm, ±250 μm or ±300 μm) of the microspheres. As an exemplary illustration, if the diameter of a population of calibrated microspheres is from 500 μm to 700 μm (the range), then the extended range can be, for example, ±100 μm, e.g., wherein 99% of the microspheres are of a size range of from 400 μm to 800 μm, and 1% of the microspheres are of a size range outside the extended range. In another exemplary embodiment, the range is 500 μm to 700 μm, with the nominal range being 600 μm, wherein 80% of the population is ±100 μm of the nominal range (i.e., an extended range of 500 μm to 700 μm), 99% of the population is ±200 μm of the nominal range (i.e., 400 μm to 800 μm), with 0.5% to 1% of the population being larger than 800 μm and the remaining 0% to 0.5% being of the population smaller than 400 μm (for a total of 100%). In certain embodiments, the nominal range is from about 50 μm to 2000 μm, such as 80 μm, 100 μm, 200 μm, 300 μm, 400 μm, 500 μm, 600 μm, 700 μm, 800 μm, 900 μm, 1000 μm, 1100 μm, 1150 μm, 1200 μm, 1300 μm, 1400 μm, 1500 μm, 1600 μm, 1700 μm, 1800 μm, 1900 μm, 2000 μm or any range thereof.

The microspheres are stable in suspension, which allows the microspheres to be formulated and stored in suspension and injected with different liquids. More specifically, the hydrophilic nature of the microspheres permits placing them in suspension, and in particular, in the form of sterile and non-pyrogenic or pyrogen-free injectable solutions, while avoiding the formation of aggregates or adhesion to the walls of storage containers and implantation devices, such as catheters, syringes, needles, and the like.

Microspheres provided herein can be implanted, such as by injection, in various locations of the body. The polymeric material for use in the compositions and methods provided herein is non-toxic to tissues and cells and is biocompatible, i.e., generally does not cause inflammation. The microspheres can maintain their general shape and position once implanted at a desired site. The microspheres provided herein are compressible and, in specific embodiments, can be injected through needles of 18 gauge or smaller.

In certain embodiments, the microspheres are injectable through a needle of 18 gauge or smaller and are not capable of being eliminated, or have reduced elimination, by the immune or lymphatic system. In some embodiments, the polymers are coated with agents which promote cell adhesion. In certain embodiments, the microspheres comprise a cell adhesion promoter in addition to the gelatin or gelatin substitute. Various types of cell adhesion promoters well known in the art can be used. In some embodiments, the cell adhesion promoter is selected from collagen, gelatin, carboxymethyl (CM) dextran, DEAE dextran, glucosaminoglycans, fibronectin, lectins, polycations (such as polylysine, chitosan), any other natural or synthetic biological cell adhesion agent or any combinations thereof. In certain embodiments, the stability of the microspheres is increased by reticulating the adhesion agent. In the case of gelatin, for example, the reticulating agent can be chosen among the difunctional chemical agents reacting on the gelatin amines (e.g., glutaraldehyde, formaldehyde, glyoxal, and the like). In some embodiments, the cell adhesion promoter is present in the microsphere, or other solid substrate, in an amount from about 0.1 g/ml to 1 g/ml of settled microspheres.

In certain embodiments, the microspheres are visible in the light and within the body by, for example, further comprising a marking agent. In some embodiment, microspheres can be marked after their synthesis. This can be done, for example, by grafting of fluorescent markers derivatives (including, for example, fluorescein isothiocyanate (FITC), rhodamine isothiocyanate (RITC) and the like). In some embodiments, a detectable monomer can be obtained by chemical coupling of the monomer with a marker, which can be: a chemical dye, such as Cibacron Blue or Procion Red HE-3B, making possible a direct visualization of the microspheres, a magnetic resonance imaging agent (erbium, gadolinium or magnetite); a contrasting agent, such as barium or iodine salts, including, for example, (acrylamido-3-propionamido)-3-triiodo-2,4,6-benzoic acid. In the case of barium or magnetite salts, they can be directly introduced in powered form in the initial monomer solution. In a certain embodiment, the contrast agent is a radiopaque contrast agent, such as a non-ionic contrast agent. In some embodiments, the contrast agent is mixed with the microsphere prior to, during and/or after injection into the patient. In a specific embodiment, the patient is administered a composition comprising a contrast agent (e.g., a non-ionic contrast agent) and microspheres provided herein.

Cell adhesion promoters or marking agents can be introduced on microspheres by chemical coupling procedures well known in affinity chromatography. The introduction can also be accomplished by diffusion within the gel network that constitutes the microsphere and then trapping the diffused molecules in place by precipitation or chemical cross-linking. In some embodiments, living cells (e.g., stem cells) are attached to the microspheres forming layers of cells therein or thereon that link with surrounding tissues and can enhance the long-term stability of the beads.

1. N-Tris-Hydroxymethyl Methylacrylamide Monomer

N-tris-hydroxymethyl methylacrylamide can also be known as trisacryl, N-[1,3-dihydroxy-2-(hydroxymethyl)propan-2-yl]prop-2-enamide; TRIS-acrylamide; N-[tris(hydroxymethyl)methyl]acrylamide; N-acryloyltris(hydroxymethyl)aminomethane; or N-acryloyl-tris(hydroxymethyl)aminomethane. In certain embodiments, N-tris-hydroxymethyl methylacrylamide is defined as having a CAS Registry Number 13880-05-2, a molecular formula of $C_7H_{13}NO_4$, a molecular weight of about 175.2 grams per mole, and a structure of:

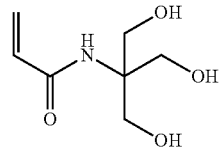

N-tris-hydroxymethyl methylacrylamide monomers are commercially available (e.g., PALL Biosepra, France or Sigma Aldrich Fine Chemicals (SAFC), product number 78561) or can be synthesized (see, e.g., Example 4). In certain embodiments, the N-tris-hydroxymethyl methylacrylamide monomer is synthesized according to the following scheme:

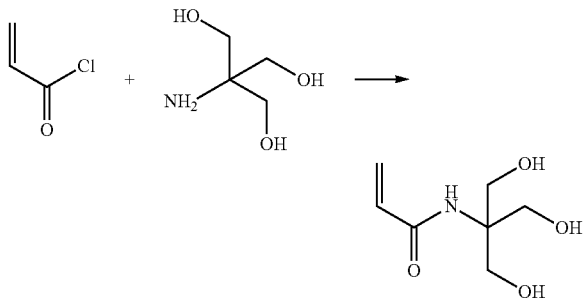

In certain embodiments, the N-tris-hydroxymethyl methylacrylamide monomer is an ultra-pure monomer. In specific embodiments, the ultra-pure N-tris-hydroxymethyl methylacrylamide monomer comprises from 0% to 9% of impurities, i.e., substances other than N-tris-hydroxymethyl methylacrylamide such as excess starting materials or derivatives thereof (e.g., acryloyl chloride or 2-amino-2-(hydroxymethyl)propane-1,3-diol), by-products or inorganic salts, for example, as determined by the bromine test (e.g., as provided in Example 6). In some embodiments, the N-tris-hydroxymethyl methylacrylamide monomer comprises from 25% to 0% impurities, such as from 25% to 20%, from 25% to 15%, from 25% to 10%, from 25% to 5%, from 25% to 1%, from 25% to 0%, from 20% to 15%, from 20% to 10%, from 20% to 5%, from 20% to 1%, from 20% to 0%, from 15% to 10%, from 15% to 5%, from 15% to 1%, from 15% to 0%, from 10% to 5%, from 10% to 1%, from 10% to 0%, from 5% to 1%, from 5% to 0% (e.g., as determined by HPLC, e.g., as provided in Example 5). In other embodiments, the N-tris-hydroxymethyl methylacrylamide monomer comprises from 25% to 0% impurities, such as from 25% to 20%, from 25% to 15%, from 25% to 10%, from 25% to 5%, from 25% to 1%, from 25% to 0%, from 20% to 15%, from 20% to 10%, from 20% to 5%, from 20% to 1%, from 20% to 0%, from 15% to 10%, from 15% to 5%, from 15% to 1%, from 15% to 0%, from 10% to 5%, from 10% to 1%, from 10% to 0%, from 5% to 1%, from 5% to 0% (e.g., as determined by HPLC, e.g., as provided in Example 5). In some embodiments, the N-tris-hydroxymethyl methylacrylamide monomer comprises less than 25%, less than 24%, less than 23%, less than 22%, less than 21%, less than 20%, less than 9%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by the bromine test, e.g., as provided in Example 6). In other embodiments, the N-tris-hydroxymethyl methylacrylamide monomer comprises less than 25%, less than 24%, less than 23%, less than 22%, less than 21%, less than 20%, less than 9%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by HPLC, e.g., as provided in Example 5). In specific embodiments, the N-tris-hydroxymethyl methylacrylamide monomer comprises less than 9%, less than 8%, less than 7%, less than 6%, less than 5%, less than 4%, less than 3%, less than 2%, less than 1%, or 0% of impurities, or any range thereof (e.g., as determined by the bromine test, e.g., as provided in Example 6). In other embodiments, the N-tris-hydroxymethyl methylacrylamide monomer comprises less than 9%, less than 8%, less than 7%, less than 6%, less than 5%, less than 4%, less than 3%, less than 2%, less than 1%, or 0% of impurities, or any range thereof (e.g., as determined by HPLC, e.g., as provided in Example 5).

2. Diethylaminoethylacrylamide Monomer

Diethylaminoethylacrylamide can also be known as DEAE, DEAE acrylamide, N-((2-diethylamino)ethyl)acrylamide; N-(2-diethylaminoethyl)prop-2-enamide; N-((2-diethylamino)ethyl)acrylamide; N-(2-(diethylamino)ethyl) acrylamide; or N-(2-(diethylamino)ethyl)-2-propenamide.

In certain embodiments, diethylaminoethylacrylamide is defined as having a molecular formula of $C_9H_{18}N_2O$, a molecular weight of about 170.3 grams per mole, and a structure of:

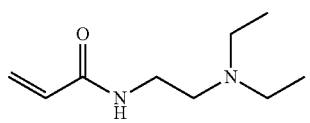

Diethylaminoethylacrylamide monomers are commercially available (e.g., PALL Biosepra, France or SAFC) or can be synthesized (see, e.g., Example 1). In certain embodiments, the diethylaminoethylacrylamide monomer is synthesized according to the following scheme:

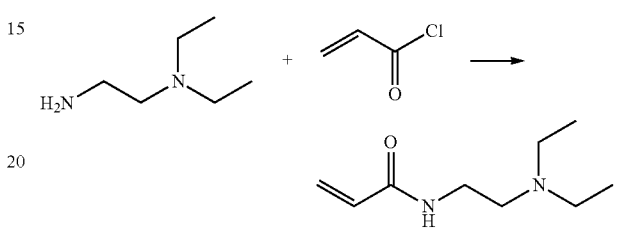

In certain embodiments, the diethylaminoethylacrylamide monomer is an ultra-pure monomer. In specific embodiments, the ultra-pure diethylaminoethylacrylamide monomer, comprises from 0% to 2% of impurities, i.e., substances other than diethylaminoethylacrylamide such as excess starting materials or derivatives thereof (e.g., acryloyl chloride, N,N,N',N'-tetramethylethylenediamine or N,N-diethylethylenediamine), by-products or inorganic salts (as determined by the bromine test, e.g., as provided in Example 3). In some embodiments, the diethylaminoethylacrylamide monomer comprises from 20% to 0% impurities, such as from 20% to 15%, from 20% to 10%, from 20% to 5%, from 20% to 1%, from 20% to 0%, from 15% to 10%, from 15% to 5%, from 15% to 1%, from 15% to 0%, from 10% to 5%, from 10% to 1%, from 10% to 0%, from 5% to 1%, from 5% to 0% (e.g., as determined by the bromine test, e.g., as provided in Example 3). In other embodiments, the diethylaminoethylacrylamide monomer comprises from 20% to 0% impurities, such as from 20% to 15%, from 20% to 10%, from 20% to 5%, from 20% to 1%, from 20% to 0%, from 15% to 10%, from 15% to 5%, from 15% to 1%, from 15% to 0%, from 10% to 5%, from 10% to 1%, from 10% to 0%, from 5% to 1%, from 5% to 0% (e.g., as determined by HPLC, e.g., as provided in Example 2). In some embodiments, the diethylaminoethylacrylamide monomer comprises less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by the bromine test, e.g., as provided in Example 3). In other embodiments, the diethylaminoethylacrylamide monomer comprises less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by HPLC, e.g., as provided in Example 2). In specific embodiments, the DEAE monomer comprises less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by the bromine test, e.g., as provided in Example 3). In other specific embodiments, the DEAE monomer comprises less than 5%, less than 4%, less than 3%, less than 2.75%, less than 2.5%, less than 2.25%, less than 2%, less than 1.75%, less than 1.5%, less than 1.25%, less than 1%, less than 0.25%, less than 0.5%, less than 0.25% or 0% of impurities or any range thereof (e.g., as determined by HPLC, e.g., as provided in Example 2). The DEAE monomer can be provided in a liquid or solid form. In certain embodiments, the DEAE monomer is provided in a liquid amine form. In specific embodiments, the DEAE monomer is not provided in a powder salt form (powder).

3. N,N-Methylene-Bis-Acrylamide Monomer

N,N-methylene-bis-acrylamide can also be known as MBA, N-[(prop-2-enoylamino)methyl]prop-2-enamide; methylenediacrylamide; methylenebisacrylamide; N,N'-methylenediacrylamide; N,N'-methylenebisacrylamide; or N,N'-methylidenebisacrylamide.

In certain embodiments, N,N-methylene-bis-acrylamide is defined as having a molecular formula of $C_7H_{10}N_2O_2$, a molecular weight of about 154.2 grams per mole, and a structure of:

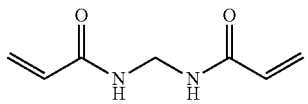

N,N-methylene-bis-acrylamide monomers are commercially available (e.g., PALL Biosepra, France or SAFC) or can be synthesized. In certain embodiments, the N,N-methylene-bis-acrylamide monomer is synthesized according to the following scheme:

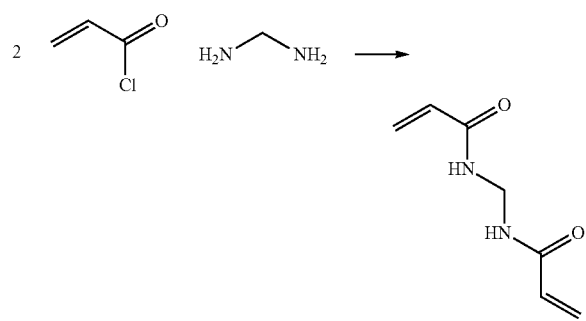

In certain embodiments, the N,N-methylene-bis-acrylamide monomer is an ultra-pure monomer. In specific embodiments, the ultra-pure N,N-methylene-bis-acrylamide monomer comprises from 0% to 9% of impurities, i.e., substances other than N,N-methylene-bis-acrylamide monomer such as excess starting materials or derivatives thereof, by-products or inorganic salts (e.g., as determined by the bromine test). In other embodiments, the ultra-pure N,N-methylene-bis-acrylamide monomer comprises from 0% to 9% of impurities, i.e., substances other than N,N-methylene-bis-acrylamide monomer such as excess starting materials or derivatives thereof, by-products or inorganic salts (e.g., as determined by HPLC). In some embodiments, the N,N-methylene-bis-acrylamide monomer comprises less than 9%, less than 8%, less than 7%, less than 6%, less than 5%, less than 4%, less than 3%, less than 2%, less than 1%, less than 0.5% or 0% of impurities, or any range thereof (e.g., as determined by the bromine test). In some embodiments, the N,N-methylene-bis-acrylamide monomer comprises less than 9%, less than 8%, less than 7%, less than 6%, less than 5%, less than 4%, less than 3%, less than 2%, less than 1%, less than 0.5% or 0% of impurities, or any range thereof (e.g., as determined by HPLC).

The purity of any of the monomers provided herein can be assessed by a variety of methods known in the art. For example, the content of impurities can be determined by the content of double bonds in the monomers, for example, the bromine test (see, e.g., Examples 3 and 6). The bromine test can be used to determine if the compound contains any double $C\!\!=\!\!C$ bonds, or the alkene functional group, because alkenes can react readily with bromine to produce color change. Exemplary bromination reaction:

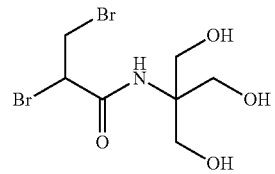 [SMILES: O=C(NC(CO)(CO)CO)C(Br)CBr]

The bromine reacts with the double bond and the consumption of bromine determines the quantity of double bond present, which is then used to evaluate so the purity, or the real presence of a monomer (e.g., trisacryl). The standard deviation can be at least +/−3% using this reaction. The quantity of double bonds present can correspond to the purity of the monomer present, because side products should not be present in large quantities. Exemplary side products are:

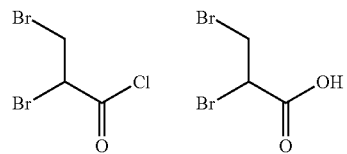 [SMILES: O=C(Cl)C(Br)CBr ; O=C(O)C(Br)CBr]

The impurities present in the monomers can also be detected by other methods with a higher detection sensitivity (e.g., high performance liquid chromatography (HPLC), gas chromatography (GC) or nuclear magnetic resonance (NMR)). In an illustrative example, an HPLC analysis can be performed to assess the purity of N-tris-hydroxymethyl methylacrylamide monomers by running the monomer samples on a Waters Atlantic $C_{18}$ column (e.g., 5 μm, 4.6×250 mm) and detecting the absorption at a specific wavelength, for example, at about 230 nm (see, e.g., Examples 2 and 5). The purity of the tested monomers can be determined, for example, by comparing the HPLC curve of the tested samples to the HPLC curve of a control monomer with known purity.

In certain embodiments, the DEAE monomer comprises less than 2.5%, less than 2%, less than 1.5%, or less than 1% of each or both of the following impurities (e.g., as determined by HPLC), either alone or in combination:

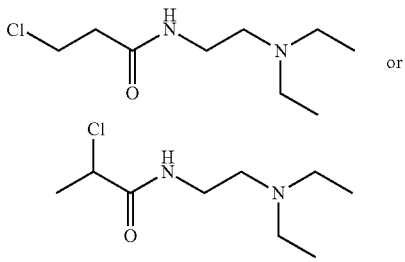

In some embodiments, the microsphere comprises about 1% to about 95% by weight of a N-tris-hydroxymethyl methylacrylamide monomer (e.g., an ultra-pure monomer). In certain embodiments, the microsphere comprises a N-tris-hydroxymethyl methylacrylamide monomer (e.g., an ultra-pure monomer) in an amount selected from the group consisting of about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, and about 95% by weight (or in range thereof).

In certain embodiments, the microsphere comprises about 1% to about 95% by weight of a diethylaminoethylacrylamide monomer (e.g., an ultra-pure monomer). In certain embodiments, the microsphere comprises a diethylaminoethylacrylamide monomer (e.g., an ultra-pure monomer) in an amount selected from the group consisting of about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, and about 95% by weight (or in range thereof).

In other embodiments, the microsphere comprises about 1% to about 95% by weight of a N,N-methylene-bis-acrylamide monomer (e.g., an ultra-pure monomer). In certain embodiments, the microsphere comprises a N,N-methylene-bis-acrylamide monomer (e.g., an ultra-pure monomer) in an amount selected from the group consisting of about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, and about 95% by weight (or in range thereof).

In one embodiment, the microsphere comprises from about 58% to about 66% by weight of a N-tris-hydroxymethyl methylacrylamide monomer, from about 22% to about 26% by weight of a diethylaminoethylacrylamide monomer and about 6% to about 7% by weight of a N,N-methylene-bis-acrylamide monomer, and about 0% to about 13% by weight of gelatin or gelatin substitute, such that the total is 100%.

The microspheres provided herein can, in certain embodiments, comprise in any combination of the percentages by weight of the above-listed monomers (e.g., one or more ultra-pure monomers).

In certain embodiments, microspheres provided herein prepared from one or more of the N-tris-hydroxymethyl methylacrylamide, diethylaminoethylacrylamide and/or N,N-methylene-bis-acrylamide ultra-pure monomers provided herein or comprising one or more of the N-tris-hydroxymethyl methylacrylamide, diethylaminoethylacrylamide and/or N,N-methylene-bis-acrylamide ultra-pure monomer units provided herein (e.g., using a method provided herein) can result in the reduction or one of more side effects in a subject following injection as compared to the same microsphere prepared without the one or more ultra-pure monomers. Without wishing to be bound by theory, the reduced side effects can be the result of the decreased amount of impurities (e.g., a reaction side product, such as ethanol or acrylic acid, unreacted monomers and/or inhibitors) in the prepared microspheres.

In other embodiments, microspheres provided herein prepared from one or more of the N-tris-hydroxymethyl methylacrylamide, diethylaminoethylacrylamide and/or N,N-methylene-bis-acrylamide ultra-pure monomers provided herein or comprising one or more of the N-tris-hydroxymethyl methylacrylamide, diethylaminoethylacrylamide and/or N,N-methylene-bis-acrylamide ultra-pure monomer units provided herein (e.g., using a method provided herein) can result in an increase in polymerization efficiency (e.g., wherein more of the monomer is incorporated into the polymer and/or better crosslinking efficiency) as compared to the same microsphere prepared without the one or more ultra-pure monomers.

In another embodiment, microspheres provided herein prepared from one or more of the N-tris-hydroxymethyl methylacrylamide, diethylaminoethylacrylamide and/or N,N-methylene-bis-acrylamide ultra-pure monomers provided herein or comprising one or more of the N-tris-hydroxymethyl methylacrylamide, diethylaminoethylacrylamide and/or N,N-methylene-bis-acrylamide ultra-pure monomer units provided herein (e.g., using a method provided herein) can result in an increase in gel point as compared to the same microsphere prepared without the one or more ultra-pure monomers. Increased gel points can result in a faster polymerization reaction, which can further lead to a decrease in the number of aggregated microspheres in a population. Methods for assessing gel point in polymerization reactions are known in the art (see, e.g., Nita et al. (2007) Rheol. Acta 46, 595-600).

In yet other embodiments, microspheres provided herein prepared from one or more of the N-tris-hydroxymethyl methylacrylamide, diethylaminoethylacrylamide and/or N,N-methylene-bis-acrylamide ultra-pure monomers provided herein or comprising one or more of the N-tris-hydroxymethyl methylacrylamide, diethylaminoethylacrylamide and/or N,N-methylene-bis-acrylamide ultra-pure monomer units provided herein (e.g., using a method provided herein) can result in an improvement in the overall manufacturing process of the microspheres, which can lead to an improvement in the yield and/or overall quality of the microspheres (e.g., less broken and/or aggregated microspheres), a more consistent product, better uniformity in size, narrower size distribution, better uniformity in shape, or any combination thereof, as compared to the same microsphere prepared without the one or more ultra-pure monomers.

4. NMR Analysis of Microsphere

In certain embodiments, the microsphere provided herein, when analyzed by NMR spectroscopy (see e.g., Example 14), exhibits a first peak (e.g., from about 3.5 ppm to about 4.0 ppm), a second peak (e.g., from about 3.0 ppm to about 3.5 ppm, and a third peak (e.g., from about 1.0 ppm to about 1.4 ppm) in a one-dimensional (1D) $^1$H NMR spectrum. In some embodiments, the NMR can be performed by an NMR spectrometer, for example, by an Avance I Bruker spectrometer ($^1$H), equipped with a tuned 4 mm HR-MAS probehead ($^1$H, $^{13}$C, lock $^2$H) or a similar equipment. In certain embodiments, the high resolution magic angle spinning (HR-MAS) technique can be employed to analyze the microsphere. Without wishing to be bound by any theory, the HR-MAS technique was initially developed for the combinatorial chemistry using the solid phase synthesis. The HR-MAS is particularly useful for the analysis of samples not fully soluble or containing solids. It gives very good results when the sample has the property of swelling or increasing the mobility in an appropriated solvent. HR-MAS NMR can be considered a hybrid technique between solid state NMR and classical solution state NMR. Similar to solid state NMR, the use of magic angle spinning (MAS) effectively removes spectral line broadening resulting from chemical shift anisotropy, homonuclear dipolar interactions, and magnetic susceptibility.

In some embodiments, the $^1$H NMR spectrum can be recorded at from 100 MHz and 900 MHz, such as at 100 MHz, 200 MHz, 300 MHz, 400 MHz, 500 MHz, 600 MHz, 700 MHz, 800 MHz, or 900 MHz, or a range thereof. In a specific embodiment, the $^1$H NMR spectrum is recorded at 400 MHz. In certain embodiments, the microsphere can be dispersed in any solvent compatible with the NMR analysis. Exemplary solvents include, but are not limited to, deuterated solvents such as deuterated water, acetic acid-d$_4$, acetone-d$_6$, acetonitrile-d$_3$, benzene-d$_6$, chloroform-d, dichloromethane-d$_2$, N,N-dimethyl formamide-d$_7$, dimethyl sulfoxide-d$_6$, ethanol-d$_6$, methanol-d$_4$, nitromethane-d$_3$, pyridine-d$_5$, tetrahydrofuran-d$_8$, toluene-d$_8$, trifluoroacetic acid-d$_4$, and trifluoroethanol-d$_3$, and other solvents such as carbon disulphide, 1,1,2,2-tetrachloroethane, carbon tetrachloride, diethyl ether (−100° C.), dimethyl ether (−100° C.), 1,4-dioxan, trichlorofluoromethane, nitrobenzene, tetrahydrofuran (−100° C.). In a specific embodiment, the solvent is deuterated water (D$_2$O).

In certain embodiments, the microsphere can be analyzed by NMR spectroscopy at a temperature of from about 0° C. to about 80° C., such as from about 10° C. to about 50° C., from about 15° C. to about 35° C., from about 20° C. to about 25° C. (e.g., the room temperature), or from about 0° C. to about 5° C., or any range thereof. In a specific embodiment, the microsphere is analyzed at a temperature of about 25° C.

In a specific embodiment, the microspheres are analyzed in an a one-dimensional 1D $^1$H NMR spectrum, using the parameters essentially as provided in Example 14 (e.g., Table 10), and the first, second and third peaks and/or the integration ratios of the second peak to the first peak (normalized to 1) and the third peak to the first peak are determined.

The first peak exhibited by the microsphere in the $^1$H NMR spectrum may be attributed, for example, to the tris-hydroxymethyl groups (e.g., C(CH$_2$OH)$_3$) in the copolymer of the microsphere. In certain embodiments, the first peak exhibited by the microsphere in the $^1$H NMR spectrum is from about 3.60 ppm to about 3.95 ppm, such as from about 3.65 ppm to about 3.90 ppm, from about 3.70 ppm to about 3.85 ppm, or from about 3.75 ppm to about 3.80 ppm, or any range thereof. In a specific embodiment, the first peak exhibited by the microsphere in the $^1$H NMR spectrum is at about 3.77 ppm.

The second peak exhibited by the microsphere in the $^1$H NMR spectrum may be attributed, for example, to the CH$_2$ groups linked to the basic nitrogen atom (e.g., (CH$_2$N (CH$_2$CH$_3$)$_2$)). In certain embodiments, the second peak exhibited by the microsphere in the $^1$H NMR spectrum is from about 3.05 ppm to about 3.45 ppm, such as from about 3.10 ppm to about 3.40 ppm, from about 3.15 ppm to about 3.35 ppm, from about 3.20 ppm to about 3.30 ppm, or from about 3.15 ppm to about 3.25 ppm, or any range thereof. In a specific embodiment, the second peak exhibited by the microsphere in the $^1$H NMR spectrum is at about 3.2 ppm.

The third peak exhibited by the microsphere in the $^1$H NMR spectrum may be attributed, for example, to the groups in the β position of the carboxamide group in the polymerized structure of the microsphere (e.g., CH$_2$—CHCONH). In certain embodiments, the third peak exhibited by the microsphere in the $^1$H NMR spectrum is from about 1.01 ppm to about 1.49 ppm, such as from about 1.05 ppm to about 1.47 ppm, from about 1.10 ppm to about 1.45 ppm, from about 1.15 ppm to about 1.40 ppm, or from about 1.25 ppm to about 1.35 ppm or any range thereof. In a specific embodiment, the third peak exhibited by the microsphere in the $^1$H NMR spectrum is at about 1.3 ppm. In some embodiments, (i) the second peak is at about 3.245 ppm or less, such as about 3.211 ppm or less or about 3.192 ppm or less; (ii) the third peak is at about 1.297 ppm or less, such as about 1.283 ppm or less or about 1.276 ppm or less; (ii) or any combination of (i) and (ii). In one embodiment, the second peak is not at 3.212 or 3.246 (+/−0.002 or 0.005) ppm and/or the third peak is not at 1.284 or 1.298 (+/−0.002 or 0.005) ppm.

In certain embodiments, the integration ratio of the second peak to the first peak exhibited by the microsphere in the $^1$H NMR spectrum is from about 0.498 to about 0.650, such as from about 0.53 to about 0.63, from about 0.55 to about 0.60, or any range thereof. In some embodiments, the integration ratio of the second peak to the first peak exhibited by the microsphere in the $^1$H NMR spectrum is about 0.50, 0.51, 0.52, 0.53, 0.54, 0.55, 0.56, 0.57, 0.58, 0.59, 0.60, 0.61, 0.62, 0.63, 0.64, or 0.65, or any range thereof. In certain embodiments, the integration ratio of the second peak to the first peak exhibited by the microsphere in the $^1$H NMR spectrum is about 0.571, 0.572, 0.573, 0.574, 0.575, 0.576, 0.577, 0.578, or 0.579, or any range thereof. In a specific embodiment, the integration ratio of the second peak to the first peak exhibited by the microsphere in the $^1$H NMR spectrum is about 0.574.

Integration ratios can be calculated using methods known in the art, for example, by normalizing the first peak to the value of 1 and them comparing the ratio of the second (or third) peak to the first peak. Without wishing to be bound by theory, it is thought that the integration ratios can be used to directly correlate to the proportion of each material that is incorporated into the polymer chain. That is, higher integration ratios can correlate with more monomers and/or a higher proportion of monomers and less impurities incorporated into the final polymer product, as well as an overall better efficiency of polymerization.

In some embodiments, the integration ratio of the second peak to the first peak exhibited by a microsphere comprising a copolymer prepared by copolymerizing (i) an ultra-pure N-tris-hydroxymethyl methylacrylamide monomer, (ii) an ultra pure diethylaminoethylacrylamide monomer, (iii) an ultra-pure N,N-methylene-bis-acrylamide monomer, (iv) an ultra-pure N-tris-hydroxymethyl methylacrylamide monomer and an ultra pure diethylaminoethylacrylamide monomer, (v) an ultra-pure N-tris-hydroxymethyl methylacrylamide monomer and an ultra-pure an N,N-methylene-bis-acrylamide monomer, (vi) an ultra pure diethylaminoethylacrylamide monomer and an ultra-pure an N,N-methylene-bis-acrylamide monomer, or (vii) an ultra-pure N-tris-hydroxymethyl methylacrylamide monomer, an ultra pure diethylaminoethylacrylamide monomer, and an ultra-pure an N,N-methylene-bis-acrylamide monomer in the $^1$H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, as compared to the same microsphere prepared without the ultra-pure monomer(s).

In some embodiments, the integration ratio of the second peak to the first peak exhibited by a microsphere comprising (i) an ultra-pure N-tris-hydroxymethyl methylacrylamide monomer unit, (ii) an ultra pure diethylaminoethylacrylamide monomer unit, (iii) an ultra-pure N,N-methylene-bis-acrylamide monomer unit, (iv) an ultra-pure N-tris-hydroxymethyl methylacrylamide monomer unit and an ultra pure diethylaminoethylacrylamide monomer unit, (v) an ultra-pure N-tris-hydroxymethyl methylacrylamide monomer unit and an ultra-pure an N,N-methylene-bis-acrylamide monomer unit, (vi) an ultra pure diethylaminoethylacrylamide monomer unit and an ultra-pure an N,N-methylene-bis-acrylamide monomer unit, or (vii) an ultra-pure N-tris-hydroxymethyl methylacrylamide monomer unit, an ultra pure diethylaminoethylacrylamide monomer unit, and an ultra-pure an N,N-methylene-bis-acrylamide monomer unit in the $^1$H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, as compared to the same microsphere that do not comprise the ultra-pure monomer unit(s) (prepared without the respective ultra-pure monomer(s)).

In certain embodiments, the integration ratio of the third peak to the first peak exhibited by the microsphere in the $^1$H NMR spectrum is from about 0.53 to about 0.75, such as from about 0.57 to about 0.60, from about 0.60 to about 0.65, from about 0.61 to about 0.75 or from about 0.61 to about 0.65 or any range thereof. In certain embodiments, the integration ratio of the third peak to the first peak exhibited by the microsphere in the $^1$H NMR spectrum is about 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, or 0.75, or any range thereof. In certain embodiments, the integration ratio of the third peak to the first peak exhibited by the microsphere in the $^1$H NMR spectrum is about 0.611, 0.612, 0.613, 0.614, 0.615, 0.616, 0.617, 0.618, 0.619, 0.620, 0.621, 0.622, 0.623, 0.624, 0.625, 0.626, 0.627, 0.628, or 0.629, or any range thereof. In a specific embodiment, the integration ratio of the third peak to the first peak exhibited by the microsphere in the $^1$H NMR spectrum is about 0.625.

In some embodiments, the integration ratio of the third peak to the first peak exhibited by a microsphere comprising a copolymer prepared by copolymerizing (i) an ultra-pure N-tris-hydroxymethyl methylacrylamide monomer, (ii) an ultra pure diethylaminoethylacrylamide monomer, (iii) an ultra-pure an N,N-methylene-bis-acrylamide monomer, (iv) an ultra-pure N-tris-hydroxymethyl methylacrylamide monomer and an ultra pure diethylaminoethylacrylamide monomer, (v) an ultra-pure N-tris-hydroxymethyl methylacrylamide monomer and an ultra-pure an N,N-methylene-bis-acrylamide monomer, (vi) an ultra pure diethylaminoethylacrylamide monomer and an ultra-pure an N,N-methylene-bis-acrylamide monomer or (vii) an ultra-pure N-tris-hydroxymethyl methylacrylamide monomer, an ultra pure diethylaminoethylacrylamide monomer, and an ultra-pure an N,N-methylene-bis-acrylamide monomer in the $^1$H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, as compared to the same microsphere prepared without the ultra-pure monomer(s).

In some embodiments, the integration ratio of the third peak to the first peak exhibited by a microsphere comprising (i) an ultra-pure N-tris-hydroxymethyl methylacrylamide monomer unit, (ii) an ultra pure diethylaminoethylacrylamide monomer unit, (iii) an ultra-pure N,N-methylene-bis-acrylamide monomer unit, (iv) an ultra-pure N-tris-hydroxymethyl methylacrylamide monomer unit and an ultra pure diethylaminoethylacrylamide monomer unit, (v) an ultra-pure N-tris-hydroxymethyl methylacrylamide monomer unit and an ultra-pure an N,N-methylene-bis-acrylamide monomer unit, (vi) an ultra pure diethylaminoethylacrylamide monomer unit and an ultra-pure an N,N-methylene-bis-acrylamide monomer unit, or (vii) an ultra-pure N-tris-hydroxymethyl methylacrylamide monomer unit, an ultra pure diethylaminoethylacrylamide monomer unit, and an ultra-pure an N,N-methylene-bis-acrylamide monomer unit in the $^1$H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, as compared to the same microsphere that do not comprise the ultra-pure monomer unit(s) (prepared without the respective ultra-pure monomer(s)).

In some embodiments, (a) the integration ratio of the second peak to the first peak exhibited by a microsphere comprising a copolymer prepared by copolymerizing (i) an ultra-pure N-tris-hydroxymethyl methylacrylamide monomer, (ii) an ultra pure diethylaminoethylacrylamide monomer, (iii) an ultra-pure an N,N-methylene-bis-acrylamide monomer, (iv) an ultra-pure N-tris-hydroxymethyl methylacrylamide monomer and an ultra pure diethylaminoethylacrylamide monomer, (v) an ultra-pure N-tris-hydroxymethyl methylacrylamide monomer and an ultra-pure an N,N-methylene-bis-acrylamide monomer, (vi) an ultra pure diethylaminoethylacrylamide monomer and an ultra-pure an N,N-methylene-bis-acrylamide monomer or (vii) an ultra-pure N-tris-hydroxymethyl methylacrylamide monomer, an ultra pure diethylaminoethylacrylamide monomer, and an ultra-pure an N,N-methylene-bis-acrylamide monomer in the ¹H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, and (b) the integration ratio of the third peak to the first peak exhibited by a microsphere comprising a copolymer prepared by copolymerizing (i) an ultra-pure N-tris-hydroxymethyl methylacrylamide monomer, (ii) an ultra pure diethylaminoethylacrylamide monomer, (iii) an ultra-pure an N,N-methylene-bis-acrylamide monomer, (iv) an ultra-pure N-tris-hydroxymethyl methylacrylamide monomer and an ultra pure diethylaminoethylacrylamide monomer, (v) an ultra-pure N-tris-hydroxymethyl methylacrylamide monomer and an ultra-pure an N,N-methylene-bis-acrylamide monomer, (vi) an ultra pure diethylaminoethylacrylamide monomer and an ultra-pure an N,N-methylene-bis-acrylamide monomer or (vii) an ultra-pure N-tris-hydroxymethyl methylacrylamide monomer, an ultra pure diethylaminoethylacrylamide monomer, and an ultra-pure an N,N-methylene-bis-acrylamide monomer, respectively, in the ¹H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof; and (b)

In other embodiments, (a) the integration ratio of the second peak to the first peak exhibited by a microsphere comprising (i) an ultra-pure N-tris-hydroxymethyl methylacrylamide monomer unit, (ii) an ultra pure diethylaminoethylacrylamide monomer unit, (iii) an ultra-pure N,N-methylene-bis-acrylamide monomer unit, (iv) an ultra-pure N-tris-hydroxymethyl methylacrylamide monomer unit and an ultra pure diethylaminoethylacrylamide monomer unit, (v) an ultra-pure N-tris-hydroxymethyl methylacrylamide monomer unit and an ultra-pure an N,N-methylene-bis-acrylamide monomer unit, (vi) an ultra pure diethylaminoethylacrylamide monomer unit and an ultra-pure an N,N-methylene-bis-acrylamide monomer unit, or (vii) an ultra-pure N-tris-hydroxymethyl methylacrylamide monomer unit, an ultra pure diethylaminoethylacrylamide monomer unit, and an ultra-pure an N,N-methylene-bis-acrylamide monomer unit in the ¹H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, and (b) the integration ratio of the third peak to the first peak exhibited by a microsphere comprising (i) an ultra-pure N-tris-hydroxymethyl methylacrylamide monomer unit, (ii) an ultra pure diethylaminoethylacrylamide monomer unit, (iii) an ultra-pure N,N-methylene-bis-acrylamide monomer unit, (iv) an ultra-pure N-tris-hydroxymethyl methylacrylamide monomer unit and an ultra pure diethylaminoethylacrylamide monomer unit, (v) an ultra-pure N-tris-hydroxymethyl methylacrylamide monomer unit and an ultra-pure an N,N-methylene-bis-acrylamide monomer unit, (vi) an ultra pure diethylaminoethylacrylamide monomer unit and an ultra-pure an N,N-methylene-bis-acrylamide monomer unit, or (vii) an ultra-pure N-tris-hydroxymethyl methylacrylamide monomer unit, an ultra pure diethylaminoethylacrylamide monomer unit, and an ultra-pure an N,N-methylene-bis-acrylamide monomer unit in the ¹H NMR spectrum is from about 5% to about 100% higher, such as about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof, as compared to the same microsphere that do not comprise the ultra-pure monomer unit(s) (prepared without the respective ultra-pure monomer(s)).

Also provided herein is a microsphere comprising (a) a copolymer prepared by copolymerizing a N-tris-hydroxymethyl methylacrylamide monomer, a diethylaminoethylacrylamide monomer and a N,N-methylene-bis-acrylamide monomer, wherein one, two or three of the monomers is an ultra-pure monomer, and (b) crosslinked gelatin; wherein the microsphere exhibits in a ¹H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is higher than the integration ratio of the same microsphere prepared without the ultra-pure monomer(s), (ii) the integration ratio of the third peak to the first peak is higher than the integration ratio of the same microsphere prepared without the ultra-pure monomer(s), or (iii) the integration ratio of the second peak to the first peak and the integration ratio of the third peak to the first peak are each higher than the respective integration ratios of same microsphere prepared without the ultra-pure monomer(s). In some embodiments, the integration ratio of the second peak to the first peak and/or the integration ratio of the third peak to the first peak is independently selected from about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof.

Also provided herein is a microsphere comprising (a) a copolymer comprising a N-tris-hydroxymethyl methylacrylamide monomer unit, a diethylaminoethylacrylamide monomer unit and a N,N-methylene-bis-acrylamide monomer unit, wherein one, two or three of the monomers units is an ultra-pure monomer unit, and (b) crosslinked gelatin; wherein the microsphere exhibits in a ¹H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is higher than the integration ratio of the same microsphere that does not comprise the ultra-pure monomer unit(s) (prepared without the respective ultra-pure monomer(s)), (ii) the integration ratio of the third peak to the first peak is higher than the integration ratio of the same microsphere p same microsphere that does not comprise the ultra-pure monomer unit(s) (prepared without the respective ultra-pure monomer(s)), or (iii) the integration ratio of the second peak to the first peak and the integration ratio of the third peak to the first peak are each higher than the respective integration ratios of same microsphere that does not comprise the ultra-pure monomer unit(s) (prepared without the respective ultra-pure monomer(s)). In some embodiments, the integration ratio of the second peak to the first peak and/or the integration ratio of the third peak to the first peak is independently selected from about 5% higher, about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, or any range thereof.

In specific embodiments, the microsphere is an ultra-pure microsphere. In certain embodiments, the ultra-pure microsphere comprises 10% or less, 9% or less, 8% or less, 7% or less, 6% or less, 5% or less, 4% or less, 3% or less, 2% or less, 1% or less or 0% of impurities by weight. In some embodiments, the ultra-pure microsphere comprise 90% or more, 91% or more, 92% or more, 93% or more, 94% or more, 95% or more, 96% or more, 97% or more, 98% or more, 99% or more, or 100% by weight of N-tris-hydroxymethyl methylacrylamide, diethylaminoethylacrylamide, N,N-methylene-bis-acrylamide and gelatin.

In one embodiment, provided herein is a microsphere comprising: (a) a copolymer comprising a N-tris-hydroxymethyl methylacrylamide monomer unit, a diethylaminoethylacrylamide monomer unit and a N,N-methylene-bis-acrylamide monomer unit, and (b) crosslinked gelatin; wherein the microsphere exhibits in a $^1$H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is from 0.50 to about 0.65, (ii) the integration ratio of the third peak to the first peak is from 0.61 to about 0.75, or (iii) a combination of (i) and (ii). In one embodiments, the first peak is at about 3.77 ppm, the second peak is at about 3.2 ppm, the third peak is at about 1.3 ppm, or a combination thereof. In some embodiments, the integration ratio of the second peak to the first peak is about 0.574, or wherein the integration ratio of the third peak to the first peak is about 0.625. In one embodiments, the microsphere of claim 1, wherein the microsphere is at 25° C. and/or in a deuterated solvent when the $^1$H NMR spectrum is recorded and/or the $^1$H NMR spectrum is recorded at 400 MHz. In some embodiments, one, two or three of the N-tris-hydroxymethyl methylacrylamide, diethylaminoethylacrylamide and N,N-methylene-bis-acrylamide monomer units is an ultra-pure monomer unit. In certain embodiments, the N-tris-hydroxymethyl methylacrylamide monomer unit comprises less than 9% of impurities and/or the diethylaminoethylacrylamide monomer unit comprises less than 2% of impurities (e.g., as determined by the bromine test). In certain embodiments, the N-tris-hydroxymethyl methylacrylamide monomer unit comprises less than 9% of impurities and/or the diethylaminoethylacrylamide monomer unit comprises less than 2% of impurities (e.g., as determined by HPLC). In another embodiment, the microsphere has a diameter from about 1 μm to about 2000 μm, from about 40 μm to about 120 μm, from about 100 μm to about 300 μm, from about 300 μm to about 500 μm, from about 500 μm to about 700 μm, from about 700 μm to about 900 μm, or from about 900 μm to about 1200 μm.

B. Compositions

The microspheres provided herein can be used in a composition (e.g., pharmaceutical composition) with a pharmaceutically acceptable liquid or other biocompatible carrier.

In certain embodiments, the microspheres or the microspheres in the compositions are substantially uniform in size. For example, in certain embodiments, the difference in diameter between individual microspheres is from about 0 μm to about 100 μm, from about 0 μm to about 50 μm, or from about 0 μm to about 25 μm. In some embodiments, the microspheres have differences in diameter of 100 μm or less, about 50 μm or less, about 25 mm or less, about 10 mm or less or about 5 μm or less.

In certain embodiments, the microspheres in the compositions have a diameter from about 1 μm to 2000 μm, from about 10 μm to 1000 μm, from about 40 μm to about 120 μm, from about 100 μm to about 300 μm, from about 300 μm to about 500 μm, from about 500 μm to about 700 μm, from about 700 μm to about 900 μm, or from about 900 μm to about 1200 μm.

In certain embodiments, the microspheres are in a population wherein greater than 68% have a diameter of ±20% of the mean, ±10% of the mean, or ±5% of the mean diameter. In one embodiment, the microspheres are in a population wherein greater than 75% have a diameter of ±20% of the mean, ±15% of the mean, ±10% of the mean or ±5% of the mean diameter, or a range thereof.

The composition can be in the form of a suspension, a hydrogel, or an emulsion. The composition can also be a suspension of microspheres in the liquid. The hydrophilic nature of the microspheres permits placing them in suspension, and in particular, in the form of sterile and non-pyrogenic or pyrogen-free injectable solutions, while avoiding the formation of aggregates or adhesion to the walls of storage containers and implantation devices, such as catheters, syringes, needles, and the like.

In some embodiments, a catheter is used for the administration. In a specific embodiment, a selectively positioned catheter is used. Such catheter has a guiding catheter inserted into a main artery, a microcatheter with or without a steerable microguide wire, and a hemostatic valve that provides a tight seal between the guiding catheter and the microcatheter, so that a continuous heparin flush can be used to prevent blood clotting.

In specific embodiments, the microspheres or the pharmaceutical compositions are suitable for injection. In specific embodiments, the microspheres and/or compositions comprising the microspheres are sterile. The microspheres can be sterilized by any method known in the art, for example, by irradiation, such as gamma or beta irradiation. In certain embodiments, the microspheres are prepared aseptically using aseptic techniques. In some embodiments, the microspheres prepared aseptically comprise a therapeutic agent or drug.

The pharmaceutically acceptable liquid can be, without limitation, saline, a buffer-solution, water, an isotonic solution, a biological fluid or a mixture thereof. The liquid can also be a salt solution, and, in certain embodiments, is composed of cations selected from the group consisting of sodium, potassium, calcium, magnesium, iron, zinc, and ammonium, for example, in an amount of from about 0.01M to about 5M. In certain embodiments, the microspheres are suspended in, or otherwise administered to a subject in combination with lipiodol and optionally a drug (e.g., doxorubicin) or other therapeutic agent.

The composition can comprise the microspheres in an amount from about 10% to about 90% by weight and the liquid (or other biocompatible carrier) in an amount from about 10% to about 90% by weight. The composition can also comprise the microspheres in an amount from about 10% to about 50% by weight and the liquid (or other biocompatible carrier) in an amount from about 50% to about 90% by weight.

Acceptable pharmaceutical carriers for therapeutic use include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin or immunoglobulins, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium and/or non-ionic surfactants such as tween, pluronics or PEG.

In some embodiments, the composition or formulation comprises the microspheres provided herein, for example as a dry powder, which can be provided in a container, such as a vial or syringe. The microspheres can be mixed with one or more pharmaceutical carriers and/or one or more other components provided herein (e.g., a marking agent and/or a therapeutic agent, such as a drug) provided herein prior to, during or after use (e.g., before, during or after injection into a patient).

In some embodiments, the biocompatible carrier is an aqueous-based solution, a hydro-organic solution, an organic solution, a non-aqueous solution, or a mixture thereof. In certain embodiments, the biocompatible carrier comprises a salt composed of cations, such as sodium, potassium, calcium, magnesium, iron, zinc, ammonium, and mixtures thereof, for example, in an amount of from about 0.01M to about 5M.

In certain embodiments, the microspheres of the composition are visible in the light and within the body, for example, by further comprising a marking agent. In some embodiment, microspheres can be marked after their synthesis. This can be done, for example, by grafting of fluorescent markers derivatives (including, for example, fluorescein isothiocyanate (FITC), rhodamine isothiocyanate (RITC) and the like). In some embodiments, a detectable monomer can be obtained by chemical coupling of the monomer with a marker, which can be: a chemical dye, such as Cibacron Blue or Procion Red HE-3B, making possible a direct visualization of the microspheres, a magnetic resonance imaging agent (erbium, gadolinium or magnetite); a contrasting agent, such as barium or iodine salts, (including, for example, (acrylamido-3-propionamido)-3-triiodo-2,4,6-benzoic acid. In the case of barium or magnetite salts, they can be directly introduced in powered form in the initial monomer solution.

In a certain embodiment, the composition comprises a contrast agent or other marking agent, such as a radiopaque contrast agent, such as a non-ionic contrast agent. In some embodiments, the contrast agent is mixed with the microspheres in the composition prior to, during and/or after injection into the patient. In a specific embodiment, the patient is administered a composition comprising a contrast agent (e.g., a non-ionic contrast agent) and microspheres provided herein.

C. Method of Making Microspheres

Provided herein a method for producing microspheres comprising a gelatin or gelatin substitute and a copolymer of a N-tris-hydroxymethyl methylacrylamide, a diethylaminoethylacrylamide and a N,N-methylene-bis-acrylamide. Further provided herein, for example, are microspheres produced by this method, as well as compositions and uses of the microspheres thereof.

The microspheres provided herein can be prepared by any method known to a skilled artisan, for example, by suspension polymerization (e.g., a water-in-oil suspension or emulsion), drop-by-drop polymerization, as described in E. Boschetti, Microspheres for Biochromatography and Biomedical Applications. Part I, Preparation of Microbeads In: *Microspheres, Microencapsulation and Liposomes*, John Wiley & Sons, Arshady R., Ed., vol. 2, p. 171-189 (1999), or as in U.S. Pat. Nos. 5,635,215 and 5,648,100, each of which is incorporated herein by reference. The mode of microsphere preparation selected will usually depend upon the desired characteristics, such as microsphere diameter and chemical composition, for the resulting microspheres. In some embodiments of the various methods provided herein, the monomers are polymerized by radical polymerization or radiation.

In certain embodiments, polymerization is carried out by emulsion or suspension polymerization, since it makes it possible to access directly microspheres of a desired size. It can be conducted as follows: the aqueous solution containing the different dissolved constituents (e.g., different monomers, cell adhesion agent), is mixed by stirring, with a solution comprising a liquid organic phase (e.g., vegetable, animal or mineral oils, certain petroleum distillation products, chlorinated hydrocarbons or a mixture of these different solutions) that has low (e.g., about 15% or less, about 10% or less, about 5% or less, about 4% or less, about 3% or less, about 2% or less, about 1% or less, about 0.5%, about 0.1% or less, or about 0%) miscibility in water (e.g., is immiscible) at 25° C., and optionally in the presence of an emulsifier (e.g., a sorbitan sesquioleate) to create a suspension of droplets, which are then turned into solid gel by polymerization of monomers by means of appropriate catalysts. In a specific embodiment, the liquid organic phase has a miscibility of about 1% or less in water at 25° C. In a certain embodiments, the liquid organic phase comprises or consists of an oil. In a specific embodiment, the liquid organic phase comprises or consists of a vegetable oil or a mineral oil (e.g., paraffin oil) or a combination of a vegetable oil and a mineral oil. The rate of stirring is adjusted so as to obtain an aqueous phase emulsion in the organic phase forming drops of desired diameter. Polymerization is then started off by addition of the initiator. It is accompanied by an exothermic reaction and its development can then be followed by measuring the temperature of the reaction medium.

The polymerization initiator is advantageously chosen among the redox systems, for example, using combinations of an alkali metal persulfate with N,N,N',N'-tetramethylethylenediamine or with dimethylaminopropionitrile, organic peroxides such as benzoyl peroxides or even 2,2'-azo-bis-isobutyronitrile. The quantity of initiator used is adapted to the quantity of monomers and the rate of polymerization sought. Polymerization can be carried out in mass or in emulsion. In the case of a mass polymerization, the aqueous solution containing the different dissolved constituents and the initiator undergoes polymerization in a homogeneous medium. This makes it possible to access a lump of aqueous gel which can then be separated into microspheres, by passing, for example, through the mesh of a screen. In certain embodiments, a polymerization initiator is added in the aqueous phase before emulsification when the polymerization initiator includes several components (redox system).

The microspheres thus obtained can then be recovered by cooling, decanting and filtration. They are then separated by size category and washed to eliminate any trace of secondary product.

The polymerization stage can be followed by a stage of reticulation of the cell adhesion agent and possibly by a marking agent stage in the case of microspheres rendered identifiable by grafting after synthesis. For example, in certain embodiments, radical polymerization of the N-tris-hydroxymethyl methylacrylamide, diethylaminoethylacrylamide, and N,N-methylene-bis-acrylamide monomers is followed by heating at a higher temperature, such as 37° C., such that the gelatin in the microspheres becomes water soluble. Then, a crosslinker, such as glutaraldehyde is used to crosslink the gelatin (e.g., about 300 ml of glutaraldehyde per about 1 L of microspheres). In certain embodiments, the microspheres are subjected to sonication prior to gelatin crosslinking.

Thus, in one aspect, provided herein is a method of making a microsphere, comprising: (a) preparing an aqueous solution comprising a N-tris-hydroxymethyl methylacrylamide monomer, a diethylaminoethylacrylamide monomer, a N,N-methylene-bis-acrylamide monomer, and gelatin, wherein at least one of the monomers is an ultra-pure monomer; (b) adding the aqueous solution to a liquid organic phase (e.g., an oil, such as a mineral oil, such as a paraffin oil) that has low miscibility in water, before or while stirring; thereby producing microspheres comprising a copolymer comprising N-tris-hydroxymethyl methylacrylamide, diethylaminoethylacrylamide and N,N-methylene-bis-acrylamide monomer units; (c) optionally subjecting the microspheres to sonication (e.g., ultrasonication); and (d) crosslinking the gelatin. Subsequently, microspheres can be collected by filtration or centrifugation and washed. In certain embodiments, the aqueous solution of monomers can contains adhesion agents such as collagen (gelatin is a denatured collagen).

In another aspect, provided herein are microspheres prepared by a process comprising: (a) preparing an aqueous solution comprising (i) a N-tris-hydroxymethyl methylacrylamide monomer, (ii) a diethylaminoethylacrylamide monomer, (iii) a N,N-methylene-bis-acrylamide monomer, and (iv) gelatin, wherein the N-tris-hydroxymethyl methylacrylamide monomer, the diethylaminoethylacrylamide monomer and/or the N,N-methylene-bis-acrylamide monomer is an ultra-pure monomer; (b) a adding the aqueous solution to a liquid organic phase (e.g., an oil, such as a mineral oil, such as a paraffin oil) that has low miscibility in water, before or while stirring; thereby producing microspheres comprising a copolymer comprising N-tris-hydroxymethyl methylacrylamide, diethylaminoethylacrylamide and N,N-methylene-bis-acrylamide monomer units; (c) optionally subjecting the microspheres to sonication (e.g., ultrasonication); and (d) crosslinking the gelatin. In some embodiments, the microsphere exhibits in a $^1$H NMR spectrum (e.g., as provided in Example 14), a first peak (e.g., from about 3.5 ppm to about 4 ppm), a second peak (e.g., from about 3 ppm to about 3.5 ppm), and a third peak (e.g., from about 1 ppm to about 1.5 ppm). In specific embodiments, the integration ratio of the second peak to the first peak is about 0.50 to about 0.65 and/or the integration ratio of the third peak to the first peak is about 0.55 to about 0.75 (e.g., about 0.61 to about 0.75). In certain embodiments, the microspheres are uniform in size. In other embodiments, the microspheres have a diameter from about 1 µm to 2000 µm, from 40 µm to about 120 µm, from about 100 µm to about 300 µm, from about 300 µm to about 500 µm, from about 500 µm to about 700 µm, from about 700 µm to about 900 µm, or from about 900 µm to about 1200 µm. In specific embodiments, less than 1% of the microspheres are aggregated (sticking) microspheres.

Also provided herein is a method of making ultra-pure microsphere comprising about 10% or less, 9% or less, 8% or less, 7% or less, 6% or less, 5% or less, 4% or less, 3% or less, 2% or less or 1% or less of impurities and/or comprises 90% or more, 91% or more, 92% or more, 93% or more, 94% or more, 95% or more, 96% or more, 97% or more, 98% or more or 99% or more by weight of a N-tris-hydroxymethyl methylacrylamide ultra-pure monomer, a diethylaminoethylacrylamide ultra-pure monomer, a N,N-methylene-bis-acrylamide ultra-pure monomer, and gelatin, by suspension polymerization, for example by (a) preparing an aqueous solution comprising (i) a N-tris-hydroxymethyl methylacrylamide monomer, (ii) a diethylaminoethylacrylamide monomer, (iii) a N,N-methylene-bis-acrylamide monomer, and (iv) gelatin, one, two or three of the N-tris-hydroxymethyl methylacrylamide monomer and/or the diethylaminoethylacrylamide monomer or N,N-methylene-bis-acrylamide is an ultra-pure monomer; (b) adding the aqueous solution to a liquid organic phase (e.g., an oil, such as a mineral oil, such as a paraffin oil) that has low miscibility in water, before or while stirring; thereby producing microspheres comprising a copolymer comprising N-tris-hydroxymethyl methylacrylamide, diethylaminoethylacrylamide and N,N-methylene-bis-acrylamide monomer units; (c) optionally subjecting the microspheres to ultrasonication; and (d) crosslinking the gelatin. Also provided herein are the ultra-pure microspheres comprising the respective monomer units prepared by this process.

In certain embodiments of the various methods provided herein, the aqueous solution is added through a feed ring to the liquid organic phase.

In some embodiments of the methods provided herein, the method further comprises sieving the microspheres (e.g., for size calibration and/ore to reduce the number of aggregated microspheres in a population of microspheres). In other embodiments, the method does not comprise subjecting the microspheres to one or more rounds of sieving (e.g., for size calibration and/ore to reduce the number of aggregated microspheres in a population of microspheres).

In specific embodiments, the methods provided herein comprise subjecting the microspheres to sonication (e.g., ultrasonication). In certain embodiments, the sonication is done in an ultrasonic bath, e.g., for from about 10 minutes to about 15 minutes. In specific embodiments, the N-tris-hydroxymethyl methylacrylamide monomer comprises less than 9% of impurities and/or the diethylaminoethylacrylamide monomer comprises less than 2% of impurities.

In certain embodiments of the methods provided herein, the use of one or more of N-tris-hydroxymethyl methylacrylamide, diethylaminoethylacrylamide and N,N-methylene-bis-acrylamide ultra-pure monomers provided herein results in a higher yield of microsphere product as compared to a method that does not use the one or more ultra-pure monomers.

In other embodiments of the methods provided herein, the use of one or more of N-tris-hydroxymethyl methylacrylamide, diethylaminoethylacrylamide and N,N-methylene-bis-acrylamide ultra-pure monomers provided herein results in a narrower size distribution of produced microspheres as compared to a method that does not use the one or more ultra-pure monomers.

In other embodiments of the methods provided herein, the use of one or more of N-tris-hydroxymethyl methylacrylamide, diethylaminoethylacrylamide and N,N-methylene-bis-acrylamide ultra-pure monomers provided herein results in an increase in polymerization efficiency (e.g., wherein more of the monomer is incorporated into the polymer and/or better crosslinking efficiency) as compared to the same microsphere prepared without the one or more ultra-pure monomers.

In another embodiment of the methods provided herein, the use of one or more of N-tris-hydroxymethyl methylacrylamide, diethylaminoethylacrylamide and N,N-methylene-bis-acrylamide ultra-pure monomers provided herein results in an increase in gel point as compared to the same microsphere prepared without the one or more ultra-pure monomers. Increased gel points can result in a faster polymerization reaction, which can further lead to a decrease in the number of aggregated microspheres in a population. Methods for assessing gel point in polymerization reactions are known in the art (see, e.g., Nita et al. (2007) Rheol. Acta 46, 595-600).

In yet other embodiments of the methods provided herein, the use of one or more of N-tris-hydroxymethyl methylacrylamide, diethylaminoethylacrylamide and N,N-methylene-bis-acrylamide ultra-pure monomers provided herein results in an improvement in the overall manufacturing process of the microspheres, which can lead to an improvement in the yield and/or overall quality of the microspheres (e.g., less broken and/or aggregated microspheres), a more consistent product, better uniformity in size, narrower size distribution, better uniformity in shape, or any combination thereof, as compared to the same microsphere prepared without the one or more ultra-pure monomers.

1. Feed Ring Process

Figure 6:
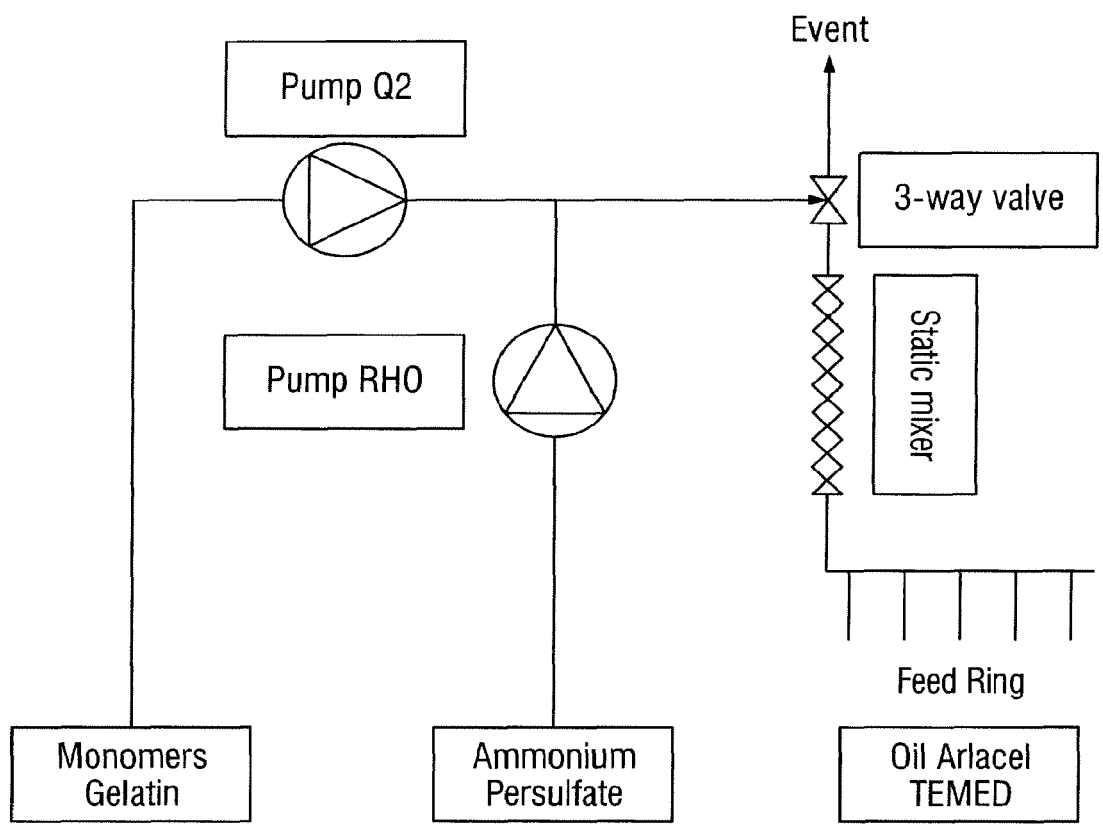
FIG. 6 illustrates a schematic diagram of an illustrative Feed Ring process.

In certain embodiments, the microspheres provided herein are produced using Feed Ring equipment (e.g., as shown in FIG. 6) during the step of adding the aqueous solution to a liquid organic phase (e.g., an oil, such as a mineral oil, such as a paraffin oil) that has low miscibility in water, before or while stirring (e.g., in step (b) in certain of the methods provided herein). The Feed Ring process can be used to further improve the quality of the microspheres produced, for example, by removing some side reaction leading to encapsulation of microspheres, encapsulation of oil and/or limiting the number of broken spheres in a population.

In an illustrative embodiment, Feed Ring equipment can comprise a static mixer. In one embodiment, the static mixer comprises a longitudinal axis and a comb having a plurality of spaced fingers extending outward from a cross-beam connected to the longitudinal axis. In some embodiments, the Feed Ring equipment is connected to one or more pumps. In one embodiment, the one or more pumps comprises a first pump (e.g., Q2 pump) and a second pump (e.g., RHO pump). In certain embodiments, the aqueous solution comprising, for example, monomers (e.g., N-tris-hydroxymethyl methylacrylamide, diethylaminoethylacrylamide, and N,N-methylene-bis-acrylamide monomers) and/or gelatin is filtered and placed under stirring. In some embodiments, the stirring is done at a temperature of about 25° C. to about 80° C., such as about 40° C. to about 70° C. In some embodiments, the stirring is done at a temperature of about 25° C., 40° C., 50° C., 55° C., 60° C., 65° C. or 70° C., or any range thereof. In a specific embodiment, the stirring is done at a temperature of about 60° C. In certain embodiments, the aqueous solution comprising microsphere monomers and gelatin is injected through the first pump into the Feed Ring equipment placed in a solution comprising an oil, such as mineral oil (e.g., paraffin oil), and an emulsifier, such as sorbitan sesquioleate (e.g., Arlacel 83; or similar product). In certain embodiments, the emulsifier (e.g., sorbitan sesquioleate) is at a concentration of from about 0.01 g/L to about 1 g/L, such as from about 0.02 g/L to about 0.5 g/L, or from about 0.03 g/L to about 0.3 g/L in oil. In one embodiment, the emulsifier (e.g., sorbitan sesquioleate) is at a concentration of about 0.031 g/L in oil (e.g., 3.1 g (or 3 ml) of Arlacel in 4 liters of oil). In certain embodiments, the solution further comprises N,N,N',N'-tetramethylethylenediamine (TEMED).

In certain embodiments, an aqueous ammonium persulfate solution is prepared and injected through the second pump into the Feed Ring equipment placed in a solution comprising an emulsifier (e.g., sorbitan sesquioleate). In one embodiment, the monomer/gelatin solution and ammonium persulfate solution are simultaneously injected through the first pump and second pump, respectively, into the Feed Ring equipment. In some embodiments, the ammonium persulfate is at a concentration of from about 0.01 g/mL to about 1 g/mL, such as from about 0.02 g/mL to about 0.5 g/mL, or from about 0.03 g/mL to about 0.3 g/mL in water. In one embodiment, the aqueous ammonium persulfate solution is at a concentration of about 0.034 g/mL in water (e.g., 3.5 g of ammonium persulfate in 101.6 g of water). In some embodiments, the use of the Feed Ring process results in reduced oil encapsulation of microspheres, decreased numbers of small particles formed within larger particles and/or reduced cracked microspheres.

2. Sonication

In certain embodiments, the microspheres provided herein are optionally subjected to sonication (particularly ultrasonication). In specific embodiments, the microspheres are subjected to sonication (e.g., ultrasonication) prior to, during or after gelatin crosslinking. In one embodiment, microspheres provided herein are subjected to sonication (e.g., ultrasonication) prior to gelatin crosslinking Sonication (e.g., ultrasonication) can be used to break the interactions between microspheres and reduce the percentage of sticking microspheres present in the microsphere population. The result of such a sonication step can result in greater efficiency in producing non-sticking microspheres (i.e., reducing the amount of aggregated microspheres) and a more cost-effective way to produce microspheres by reducing the need for (or number of) one or more rounds of sieving in an effort to eliminate sticking microspheres from a given population of microspheres.

Any ultrasound generator can be used in combination with one or more of the processes or methods of making microspheres provided herein. In certain embodiments, the sonication is performed using a sonicator, for example, an ultrasonic bath, ultrasonic probe or ultrasonic processor. In one embodiment, the sonication is performed using an ultrasonic bath. In some embodiments, the sonication is performed one time. In other embodiments, the sonication is performed more than one time. In certain embodiments, the sonication is performed at a frequency of from about 20 kHz to about 200 kHz, such as from about 30 kHz to about 100 kHz, or from about 35 kHz to about 70 kHz. In some embodiments, the sonication is performed at a frequency of about 35 kHz, 40 kHz, 45 kHz, 50 kHz, 55 kHz, 60 kHz, 65 kHz, or about 70 kHz, or any range thereof. In one embodiment, the sonication is performed at a frequency of about 35 kHz. In certain embodiments, the sonication is performed at a temperature of from about 0° C. to about 80° C., such as from about 10° C. to about 50° C., from about 15° C. to about 35° C., from about 20° C. to about 25° C. (e.g., room temperature), or from about 0° C. to about 5° C. (e.g., on ice), or any range thereof. In certain embodiments, the sonication is performed at a temperature of about 0° C., 4° C., 5° C., 10° C., 25° C. or room temperature.

In certain embodiments, the sonication is done for from about 1 minute to about 60 minutes, such as from about 5 minutes to about 40 minutes, or from about 10 minutes to about 15 minutes, or any range thereof. In some embodiments, the sonication is done for about 5, 10, 15, or 20 minutes. In one embodiment, the sonication is done for about 10 minutes or about 15 minutes. The time periods above can reflect a single, continuous sonication or multiple sonications.

In certain embodiments, the percentage of sticking (or aggregated) microspheres present after sonication is from about 0% to about 3%, from about 0% to about 2%, from about 0% to about 1.5%, from about 0% to about 1%, or from about 0% to about 0.5%, or any range thereof. In some embodiments, the percentage of sticking spheres present in the microspheres after sonication is about 0%, about 0.1%, about 0.2%, about 0.3%, about 0.4%, about 0.5%, about 0.6%, about 0.7%, about 0.8%, about 0.9% or about 1%. In certain embodiments, no broken microspheres are observed after sonication.

In some embodiments, microspheres provided herein prepared using sonication (e.g. ultrasonication) results in an improvement in the overall manufacturing process of the microspheres (e.g., higher yield and/or less expensive), which can lead to an improvement in the quality of the microspheres (e.g., less broken and/or aggregated microspheres), a more consistent product (e.g., greater uniformity in size and/or shape), or a combination thereof, as compared to the same microsphere prepared without using ultrasonication. In specific embodiments, microspheres provided herein prepared using sonication (e.g., ultrasonication) results in yields of greater than 30%, greater than 35%, greater than 40%, greater than 50%, greater than 55%, greater than 60% (or higher) of microspheres from a prepared batch (or population) of microspheres, which comprise 5% or less, 4.5% or less, 3.5% or less, 3% or less, 2.5% or less, 2% or less, 1.5% or less, 1% or less, 0.5% or less, 0.4% or less, 0.3% or less, 0.25% or less, 0.2% or less or 0.1% or less of aggregated microspheres.

In one embodiment, provided herein is a method of making microspheres comprising: (a) preparing an aqueous solution comprising: (i) a N-tris-hydroxymethyl methylacrylamide monomer, (ii) a diethylaminoethylacrylamide monomer, (iii) a N,N-methylene-bis-acrylamide monomer, and (iv) gelatin, wherein the N-tris-hydroxymethyl methylacrylamide monomer and/or the diethylaminoethylacrylamide monomer is an ultra-pure monomer; (b) adding the aqueous solution to a liquid organic phase that has low miscibility in water, before or while stirring; thereby producing microspheres comprising a copolymer comprising a N-tris-hydroxymethyl methylacrylamide monomer unit, a diethylaminoethylacrylamide monomer unit and a N,N-methylene-bis-acrylamide monomer unit; (c) optionally subjecting the microspheres to ultrasonication; and (d) crosslinking the gelatin. In some embodiments, the aqueous solution is added through a feed ring to the liquid organic phase. In an embodiment, the N-tris-hydroxymethyl methylacrylamide monomer comprises less than 9% of impurities and/or the diethylaminoethylacrylamide monomer comprises less than 2% of impurities. In one embodiment, the microspheres are ultra-pure microspheres. In another embodiments, the (i) the ultra-pure microspheres comprise about 10% or less, 9% or less, 8% or less, 7% or less, 6% or less, 5% or less, 4% or less, 3% or less, 2% or less or 1% or less of impurities, (ii) the ultra-pure microspheres comprise 90% or more, 91% or more, 92% or more, 93% or more, 94% or more, 95% or more, 96% or more, 97% or more, 98% or more or 99% or more by weight of the N-tris-hydroxymethyl methylacrylamide, the diethylaminoethylacrylamide, the N,N-methylene-bis-acrylamide and the gelatin, or (iii) a combination of (i) and (ii). In yet another embodiment, the ultrasonication is done in an ultrasonic bath. In certain embodiments, the method does not comprise sieving the microspheres.

Also provided herein are microspheres prepared by any of the various methods provided herein. In one embodiment, the microspheres prepared by these methods exhibit in a $^1$H NMR spectrum, a first peak from about 3.5 ppm to about 4 ppm, a second peak from about 3 ppm to about 3.5 ppm, and a third peak from about 1 ppm to about 1.5 ppm; and wherein (i.) the integration ratio of the second peak to the first peak is from 0.50 to about 0.65, (ii.) the integration ratio of the third peak to the first peak is from 0.61 to about 0.75, or (iii.) a combination thereof. In one embodiment, the microspheres are uniform in size. In anther embodiment, the microspheres have a diameter from about 1 μm to about 2000 μm, from 40 μm to about 120 μm, from about 100 μm to about 300 μm, from about 300 μm to about 500 μm, from about 500 μm to about 700 μm, from about 700 μm to about 900 μm, or from about 900 μm to about 1200 μm. In some embodiments, less than 1% of the microspheres are aggregated microspheres.

D. Method of Use

In certain embodiments, the microspheres are flexible, but not fragile, such that they can easily pass into and through injection devices and small catheters without being permanently altered or broken, but the microspheres are also resistant to the muscle contraction stress generated during and after the implantation process. In some embodiments, the microspheres are thermally stable which allows for easy, convenient sterilization, and frozen storage.

Thus, the microspheres provided herein have a wide variety of applications. For example, the microspheres provided herein can be used for embolization, tissue engineering, tissue guided regeneration, in vivo stem cell harvesting, culturing, or differentiation, delivery and suspension of therapeutic materials in targeted human or animal tissues and/or other applications.

Any of the various microspheres provided herein, or prepared by the various methods provided herein, can be used in any the various embolization and disease management and treatment embodiments provided herein. In one embodiment, provided is a method of embolization in a subject, comprising administering to the subject microspheres provided herein. In another embodiment, provided herein is a method of managing or treating an angiogenesis-dependent disease in a subject, comprising administering to the subject microspheres provided herein. In one embodiment, the angiogenesis-dependent disease is arteriovenous malformation, uterine fibroid, or benign prostatic hyperplasia. In an embodiment, the angiogenesis-dependent disease is a cancer or tumor, such as a liver or prostate cancer or tumor.

1. Embolization

There are a number of clinical situations (e.g., bleeding, tumor development) where it is desirable to reduce or abolish the blood supply to an organ or region. As described in greater detail below, this can be accomplished by injecting the microspheres or compositions into a desired blood vessel through a selectively positioned needle or catheter, or under the guidance of an x-ray camera (e.g., a fluoroscope). The microspheres or compositions travel via the blood stream until it becomes wedged in the vasculature, thereby physically (or chemically) occluding the blood vessel. The reduced or abolished blood flow to the selected area results in infarction (cell death due to an inadequate supply of oxygen and nutrients) or reduced blood loss from a damaged vessel.

Thus, in certain embodiments, provided herein is a method of embolization in a subject or patient, comprising administering to the subject a microsphere (microspheres) or a composition comprising the microsphere(s). In one embodiment, provided are methods for embolizing a blood vessel, comprising administering to the vessel of a subject or patient a therapeutically effective amount of the microspheres, such that the blood vessel is effectively occluded. In some embodiments, embolization can be accomplished in order to treat or prevent conditions of excessive bleeding. Embolization therapy utilizing microspheres or compositions provided herein can also be applied to a variety of other clinical situations where it is desired to occlude blood vessels, for example, for acute bleeding, vascular abnormalities, central nervous system disorders, and hypersplenism.

In the case of vascular malformations, such as AVM or arteriovenous fistulas, vascular occlusion enables the blood flow to the tissues to be normalized, aids in surgery, and limits the risk of hemorrhage. In hemorrhagic processes, vascular occlusion produces a reduction of flow, which promotes cicatrization of the arterial opening(s).

Embolization can be used in the treatment of uterine fibroids, postpartum and/or post-caesarian bleeding, post-surgical vaginal bleeding, the prevention and/or treatment of hemorrhage from ectopic pregnancy, prophilatically prior to myomectomy and in obstetrical patients at high risk for bleeding, such as those patients with placenta previa, placenta accreta, and twin fetal death. Embolization can also be used to stop uncontrolled bleeding, or to slow bleeding prior or during surgery, and for sealing endoleaks into aneurysm sacs.

Any of the various diseases or disorders provided herein, or a symptom thereof, can be managed, treated or prevented according the methods provided herein.

Furthermore, depending on the pathological conditions treated embolization can be carried out for temporary as well as permanent objectives.

Embolization can also be used in combination with other clinical procedures, such as angiography. For example, a radiopaque contrast agent can be injected to the area to be embolized through, e.g., a catheter inserted percutaneously or by surgery into an artery or vein as an x-ray is taken. The blood vessel can then be embolized by refluxing microspheres provided herein through the catheter, until flow is observed to cease. Occlusion can be confirmed by repeating the angiogram.

The microspheres provided herein can be administered to (or otherwise contacted with) a blood vessel, a tissue or organ (e.g., heart, kidney, spinal cord, uterus, liver or pancreas) by means known in the art. In certain embodiments, the microspheres are administered (e.g., by injection) to a tissue or organ that has more than one blood supply, for example the liver, lung, spine, spinal cord, uterus or pancreas. In certain embodiments, the microspheres are administered to the heart, lung, nervous system, brain, lung, liver, uterus or pancreas of the patient. In some embodiments, the microspheres are administered to one or more blood vessels, veins or arteries comprised within the tissue or organ. In certain embodiments, the microspheres provided herein are used to counter ischemia in the target area, e.g., the area of administration or injection, such as in or near a tissue or organ. In some embodiments of the methods provided herein, the microspheres are administered to a patient by intraluminal administration or injection. In other embodiments of the methods provided herein, the microspheres are administered to a patient by intravascular administration or injection.

The microspheres can be delivered systemically or locally to the desired blood vessel, tissue or organ. In some embodiments, the microspheres are administered to a blood vessel, tissue or organ before, during or after a surgery. In other embodiments, the microspheres are delivered to a blood vessel, tissue or organ using non-surgical methods, for example, either locally by direct injection into the target area, to a remote site and allowed to passively circulate to the target site, or to a remote site and actively directed to the target site. Such non-surgical delivery methods include, for example, infusion or intravascular (e.g., intravenous or intraarterial), intramuscular, intraperitoneal, intrathecal, intradermal or subcutaneous administration. In certain embodiments, angiography (e.g., selective angiography or superselective angiography) is used in conjunction with embolization to assess the blood supply to the tissue or organ. In such embodiments, an angiogram can be taken prior to, during, or after embolization.

Diseases or disorders provided herein can be treated or otherwise managed by administering to the patient (e.g., a patient in need thereof) a therapeutically effective amount of the microspheres or a composition provided herein.

In certain embodiments, administration is carried out by injection. In certain embodiments, the microspheres are administered by a catheter. In other embodiments, the microspheres are injected using a needle attached to a syringe. In some embodiments, administration is into a blood vessel. In other embodiments, administration is directly to the site of action, for example into a tumor mass, or into a cell, organ or tissue requiring such treatment or management. In some embodiments, the microspheres are administered in combination with a drug solution or other therapy, wherein the drug solution or other therapy is administered prior, simultaneously or after the administration of the microspheres.

It should be understood that the patients suitable for embolization with the microspheres provided herein include humans and animals, including male and female infants, children, and adults, including the elderly. In a specific embodiment, the patient is at risk for, or currently afflicted with, hepatocellular diseases, such as hepatitis or a liver cancer or tumor, for example Caucasian or Asian (e.g., including, but not limited to, people of Japanese heritage) human patients, 18 to 75 years of age. In some embodiments, the patients are from 25 to 75 years of age, from 25 to 50 years of age, from 50 to 75 years of age, or from 18 to 25 years of age. In one embodiment, the patient is less than 18 years of age (e.g., from 1 to 5 years of age, from 5 to 10 years of age, from 10 to 15 years of age or from 15 to 18 years of age). In another embodiment, the patient is 75 years of age or older.

In some embodiments, the microspheres provided herein are used in the treatment, management, or prevention of hepatocellular disease, or a symptom thereof, in a patient. In one embodiment, the patient is Child-Pugh class A. In another embodiment, the patient is Child-Pugh class B. In yet other embodiments, the patient is Child-Pugh class C.

The Child-Pugh classification is well known in the art, see, e.g., Child and Turcotte (1964) Surgery and portal hypertension, In: The liver and portal hypertension (Edited by: Child CG). Philadelphia, Saunders 1964, 50-64; which was later modified by Pugh et al. Transection of the esophagus in bleeding oesophageal varices (1973) *Br. J. Surg.* 60:648-652. In some embodiments, the patient is infected with a hepatitis C virus (HCV).

Microspheres and compositions provided herein can also be in combination with drugs or other therapies. For example, the microspheres and compositions can be used to treat or otherwise manage tumors or cancers (e.g., prostate or liver cancer), inflammatory diseases or other diseases associated with inflammation, or a symptom thereof. In other embodiments, the microspheres and compositions provided herein can be used to treat or otherwise manage uterine fibroids, or a symptom thereof. In other embodiments, the microspheres and compositions provided herein can be used to treat or otherwise manage a vascular malformation, such as an AVM, or a symptom thereof. In yet other embodiments, the microspheres and compositions provided herein can be used to treat or otherwise manage a prostate disease, such as a benign prostate hyperplasia, or a symptom thereof.

In certain embodiments, a drug or other therapy is administered concurrently to the subject in combination with the microspheres provided herein. In some embodiments, a drug or other therapy is administered to the subject prior to administration of microspheres. In certain embodiments, a drug or other therapy is administered from about 1 minute to about 60 minutes prior to administration of microspheres. In some embodiments, a drug or other therapy is administered to the subject within about 1 minute, about 5 minutes, about 10 minutes, about 15 minutes, about 20 minutes, about 30 minutes, about 45 minutes or about 1 hour, about 2 hours, about 4 hours, about 6 hours, about 10 hours, about 12 hours, about 18 hours, about 20 hours or about 24 hours of administration of microspheres. In yet other embodiments, a drug or other therapy is administered concurrently with microspheres. In certain embodiments, microspheres are administered to the subject prior to administration of a drug or other therapy. In certain embodiments, microspheres are administered between about 1 minute and about 60 minutes prior to administration of a drug or other therapy. In some embodiments, microspheres are administered to the subject within about 1 minute, about 5 minutes, about 10 minutes, about 15 minutes, about 20 minutes, about 30 minutes, about 45 minutes or about 1 hour, about 2 hours, about 4 hours, about 6 hours, about 10 hours, about 12 hours, about 18 hours, about 20 hours or about 24 hours of administration of a drug or other therapy.

2. Angiogenesis-Dependent Diseases

Angiogenesis-dependent diseases (i.e., those diseases which require or induce vascular growth) represent a significant portion of all diseases for which medical treatment is sought. Such diseases include, for example, cancers or tumors (e.g., liver cancers or tumors, or prostate cancer or tumors) and non-tumorigenic angiogenesis-dependent diseases.

In certain embodiments, provided herein are microspheres, compositions and methods suitable for treating or otherwise managing angiogenesis-dependent diseases, including tumors or other cancers, non-tumorigenic angiogenesis-dependent diseases, or pain, such as pain related to the presence of a tumor or other cancer, or a symptom thereof. In one embodiment, methods are provided for managing or treating an angiogenesis-dependent disease in a subject, comprising administering to the subject a microsphere (microspheres) or a composition comprising the microsphere(s). In specific embodiments, methods are provided for managing or treating an angiogenesis-dependent diseases in a subject comprising, for example, administering to the subject a microsphere (microspheres) or a composition comprising the microsphere(s).

In addition to cancer, numerous other non-tumorigenic angiogenesis-dependent diseases which are characterized by the abnormal growth of blood vessels can also be treated, either via down-regulation or up-regulation, or otherwise managed with the microspheres or compositions provided herein. Representative examples of such nontumorigenic angiogenesis-dependent diseases include, without limitation, hypertrophic scars and keloids, proliferative diabetic retinopathy, rheumatoid arthritis, arteriovenous malformation (AVM), lymphangitic malformations, venous malformations, atherosclerotic plaques, delayed wound healing, hemophilic joints, nonunion fractures Klippel Trenaunay Syndrome, Parkes Weber Syndrome, Osler-Weber-Rendu Syndrome, Blue Rubber Bleb Syndrome, cutnaoues and subcutaneous nevi, hemangiomas, leiomyomata, adenomas, hamartomas, psoriasis, pyogenic granuloma, scleroderma, tracoma, menorrhagia, vascular adhesions, benign prostatic hyperplasia (BPH) and uterine fibroids.

a. Cancers or Tumors

In specific embodiments, methods are provided for managing or treating a cancer or tumor (e.g., a hypervascularized cancer or tumor) in a subject comprising, for example, administering to the subject a microsphere (microspheres) or a composition comprising the microsphere(s). Such cancers include, without limitation (both anatomically and by primary neoplastic site), liver, ovarian, breast, kidney, lung, pancreatic, thyroid, prostate, uterine, skin cancer, head and neck tumors, breast tumors, brain, bone, soft tissues (such as sarcoma, lipoma, malignany fibrous histiocytoma), blood (such as lymphoma), Kaposi's sarcoma, and superficial forms of bladder cancer. In certain embodiments, the method of treatment or management can be the result of localized (or systemic) drug delivery in combination with embolic effects of the microspheres (e.g., TACE).

Other diseases, and symptoms thereof, contemplated for management and treatment with the compositions and methods provided herein include, for example, without limitation, tumors associated with the liver, kidney, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, testicular carcinoma, or combinations thereof.

Embolization therapy using the microspheres or compositions provided herein can be utilized in at least three principal ways to assist in the management of neoplasms: (1)

definitive treatment of tumors (usually benign); (2) for preoperative embolization; and (3) for palliative embolization. Briefly, benign tumors can sometimes be successfully treated by embolization therapy alone. Examples of such tumors include simple tumors of vascular origin (e.g., haemangiomas), endocrine tumors such as parathyroid adenomas, and benign bone tumors.

For other tumors, (e.g., renal adenocarcinoma), preoperative embolization can be employed hours or days before surgical resection in order to reduce operative blood loss, shorten the duration of the operation, and reduce the risk of dissemination of viable malignant cells by surgical manipulation of the tumor. Many tumors can be successfully embolized preoperatively, including for example nasopharyngeal tumors, glomus jugular tumors, meningiomas, chemodectomas, and vagal neuromas.

Embolization using the microspheres or compositions can also be utilized as a primary mode of treatment for inoperable malignancies, in order to extend the survival time of patients with advanced disease. Embolization can produce a marked improvement in the quality of life of patients with malignant tumors by alleviating unpleasant symptoms such as bleeding, venous obstruction and tracheal compression. The benefits from palliative tumor embolization, in certain embodiments, can be seen in patients suffering from the humoral effects of malignant endocrine tumors, wherein metastases from carcinoid tumors and other endocrine neoplasms such as insulinomas and glucagonomas can be slow growing, and yet still cause great distress by virtue of the endocrine syndromes which they produce. In certain embodiments, embolization therapy can also be used during surgery to remove a tumor or vascular mass or cancerous organ, or to prevent or ameliorate metastasis.

Chemoembolization is a combination of chemotherapy and embolization or embolotherapy, used typically to treat cancer. Similarly, radioembolization is a combination of radiation therapy and embolization or embolotherapy. In certain embodiments, the microspheres provided herein can be injected to a target area as a standalone therapy or for the purposes of interspersion between terminal therapeutic microspheres to allow for gradual migration of the microspheres into tumor blood supply, while providing continued perfusion/blood flow into targeted tumor. The addition of chemotherapeutics to the microsphere matrix can increase the efficacy of the therapy by improving the timing of exposure of therapy with the terminal embolic effect of microspheres.

A wide variety of cancers or tumors may be embolized utilizing a microsphere composition provided herein. Briefly, tumors are typically divided into two classes: benign and malignant. In a benign tumor, the cells can retain their differentiated features and do not divide in a completely uncontrolled manner. In addition, the tumor is localized and non-metastatic. In a malignant tumor, the cells can become undifferentiated, do not respond to the body's growth and hormonal signals, and multiply in an uncontrolled manner; the tumor is invasive and capable of spreading to distant sites (metastasizing). Bother benign and malignant tumors can be embolized, treated, managed, prevented or ameliorated using the microspheres provided herein.

In certain embodiments, also provided herein are methods of managing or treating secondary tumors (e.g., secondary hepatic tumors) using the microspheres or compositions provided herein. A secondary tumor, or metastasis, is a tumor which originated elsewhere in the body but has subsequently spread to a distant organ. The common routes for metastasis are direct growth into adjacent structures, spread through the vascular or lymphatic systems, and tracking along tissue planes and body spaces (peritoneal fluid, cerebrospinal fluid, etc.).

In other embodiments of the methods provided herein, embolization therapy may be used during surgery to remove a tumor or vascular mass or cancerous organ. Additionally, therapeutic embolization therapy can be used to treat, manage, prevent or ameliorate metastasis.

In certain embodiments, blood vessels which nourish a tumor are deliberately blocked by injection of an embolic material into the vessel. Notably, in the case of tumors, vascular occlusion methods provided herein can be used to suppress pain, limit blood loss on the surgical intervention to follow embolization, or even bring on a tumoral necrosis and avoid an operation.

i. Liver Cancers or Tumors

In certain embodiments, liver cancers or tumors can be treated or managed utilizing the methods comprising administering the microspheres or compositions to the subject. Representative examples of benign hepatic tumors include hepatocellular adenoma, cavernous haemangioma, and focal nodular hyperplasia. Other benign tumors, which are more rare and often do not have clinical manifestations, can also be treated. These include bile duct adenomas, bile duct cystadenomas, fibromas, lipomas, leiomyomas, mesotheliomas, teratomas, myxomas, and nodular regenerative hyperplasia.

Malignant hepatic tumors can be subdivided into two categories: primary and secondary. Primary tumors arise directly from the tissue in which they are found. Thus, a primary liver tumor is derived originally from the cells which make up the liver tissue (such as hepatocytes and biliary cells). Representative examples of primary hepatic malignancies include hepatocellularcarcinoma, cholangiocarcinoma, angiosarcoma, cystadenocarcinoma, squamous cell carcinoma, and hepatoblastoma. Hepatic malignancies, or symptoms thereof, can be treated or otherwise managed, for example, using the compositions and methods provided herein.

Arterial embolization can be done, for example, by injecting microspheres through a small tube, or catheter, threaded into the hepatic artery. For example, a catheter can be inserted via the femoral or brachial artery and advanced into the hepatic artery by steering it through the arterial system under fluoroscopic guidance. The catheter can be advanced into the hepatic arterial tree as far as necessary to allow complete blockage of the blood vessels supplying the tumor(s), while sparing as many of the arterial branches supplying normal structures as possible. This can be, for example, a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery can be embolized by injecting anti-angiogenic therapeutic compositions (e.g., microspheres provided herein and optionally one or more additional therapies) through the arterial catheter until flow in the artery to be blocked ceases, such as after observation for 5 minutes. Occlusion of the artery can be confirmed by injecting radiopaque contrast through the catheter and demonstrating by fluoroscopy or x-ray film that the vessel which previously filled with contrast no longer does so. The same procedure can be repeated with each feeding artery to be occluded.

The hepatic artery is the main source of blood for most liver tumors, and thus, microspheres can block the flow of blood to the tumor, depriving it of the nutrients and oxygen it needs to survive. In a similar manner, arterial embolization can be accomplished in a variety of other conditions, including for example, without limitation, for acute bleeding, vascular abnormalities, central nervous system disorders, and hypersplenism. In certain embodiments, transarterial chemoembolization (TACE) and transarterial embolization (TAE) can be performed to treat liver cancers or tumors. TACE is a combination therapy of TAE and regional chemotherapy, which refers to an interventional radiology procedure involving gaining percutaneous access to the hepatic artery, usually by puncturing the common femoral artery in the right groin and passing a catheter through the abdominal aorta, through the celiac axis and common hepatic artery, into the proper hepatic artery (which supplies the liver).

Selective arterial obstruction can induce ischemic tumor necrosis while minimizing damage to the liver tissue. The blood supply to the liver tissue is still maintained by dominant blood flow from the portal vein minimizing damage to the liver. In addition, chemotherapeutic agents concomitantly administered remain in a tumor for a longer period at a higher concentration. The embolotherapy interrupts the arterial blood flow to a tumor and prevents washout of the injected chemotherapeutic agents from a tumor.

TACE can derive its beneficial effect in two ways. Since most tumors are supplied by the hepatic artery, arterial embolization interrupts their blood supply and postpones growth until replaced by neovascularity. Further, focused administration of chemotherapy allows a higher dose to the tissue while simultaneously reducing systemic exposure, which is typically the dose limiting factor. This effect is potentiated by the fact that the chemotherapeutic drug is not washed out from the tumor bed after embolization. Thus, the combination of embolotherapy and regional chemotherapy has synergistic, anti-tumor effects with a high objective response rate. Another added benefit is that the use of combination therapy results in lower systemic drug levels and therefore less toxicity.

In certain embodiments, also provided herein are methods of managing or treating secondary hepatic tumors) using the microspheres or compositions provided herein. Secondary hepatic tumors are one of the most common causes of death in the cancer patient and are by far and away the most common form of liver tumor. Although virtually any malignancy can metastasize to the liver, tumors which are most likely to spread to the liver include: cancer of the stomach, colon, and pancreas; melanoma; tumors of the lung, oropharynx, and bladder; Hodgkin's and non-Hodgkin's lymphoma; tumors of the breast, ovary, and prostate. Each one of the above-named primary tumors has numerous different tumor types which can be treated by arterial embolization (for example, without limitation, there are reportedly over 32 different types of ovarian cancer).

ii. Prostate Cancers or Tumors

In certain embodiments, methods are provided for managing or treating prostate cancers or tumors, or a symptom thereof, using microspheres or compositions provided herein.

In some embodiments, the microspheres or compositions are administered to an area surrounding the prostate, such as, the prostatic artery. For example without limitation, the microspheres or compositions can be delivered to a blood vessel that nourishes the prostate cancer.

The administration of microspheres or compositions can be conducted via a syringe, a catheter, a needle and other means for injecting or infusing. The syringe, the catheter, the needle or the like can be inserted into a vein or an artery, for example, the femoral artery or the inferior vesicle artery.

In certain embodiments, a syringe, a catheter, or a needle is advanced into, for example, the ostium of the prostate arteries and, in one embodiment, advanced as far as necessary to allow complete blockage of the blood vessels supplying a prostate cancer, while sparing as many of the arterial branches supplying normal structures as possible.

In some embodiments of the methods provided herein, aniography of the area to be embolized is performed prior to embolization. The blood vessel is then embolized by refluxing an embolic material provided herein through a previously placed catheter, until flow is observed to cease. The catheter can be inserted either percutaneously or by surgery. Occlusion can be confirmed by repeating the angiogram.

b. Arteriovenous Malformation

In further specific embodiments, methods are provided for managing or treating arteriovenous malformation or a symptom thereof in a subject comprising, for example, administering to the subject a microsphere (microspheres) or a composition comprising the microsphere(s) to occlude arteries or veins to correct the arteriovenous malformation. In one embodiment, the arteriovenous malformation can be treated by inserting a catheter via the femoral or brachial artery, and advancing it into the feeding artery under fluoroscopic guidance. The catheter can be advanced as far as necessary to allow complete blockage of the blood vessels supplying the vascular malformation, while sparing as many of the arterial branches supplying normal structures as possible (ideally this will be a single artery, but most often multiple separate arteries may need to be occluded, depending on the extent of the vascular malformation and its individual blood supply). Once the desired catheter position is achieved, each artery can be embolized utilizing the microspheres or compositions provided herein.

c. Uterine Fibroids

In further specific embodiments, methods are provided for managing or treating uterine fibroids or a symptom thereof, for example, by using uterine fibroid embolization (UFE) or uterine artery embolization (UAE). The cause of uterine fibroids is unknown. However, they commonly cause heavy menstrual bleeding, pain in the pelvic region, and pressure on the bladder or bowel.

In certain embodiments, embolization (such as UFE) using the microspheres and compositions provided herein can be accomplished in order to treat conditions of excessive bleeding, including excessive bleeding associated with uterine fibroids. For example, menorrhagia (excessive bleeding with menstruation) can be readily treated by embolization of uterine arteries (e.g., branches of the internal iliac arteries bilaterally). In certain embodiments, the compositions and methods provided herein are used to manage or treat symptoms of uterine fibroids, such as heavy menstrual bleeding, pelvic pain or pressure and/or urinary dysfunction.

In some embodiments, a catheter may be inserted via the femoral or brachial artery, and advanced into each uterine artery by steering it through the arterial system under the guidance of an x-ray camera (e.g., a fluoroscope). In certain embodiments, the catheter can be advanced as far as necessary to allow complete blockage of the blood vessels to the uterus, while sparing as many arterial branches that arise from the uterine artery and supply normal structures as possible. In certain embodiments, a single uterine artery on each side may be embolized, but occasionally multiple separate arteries may need to be blocked depending on the individual blood supply. Once the desired catheter position is achieved, each artery can be embolized by administration of the microspheres and compositions as described above. The administered microspheres block the arteries that provide blood flow, causing the fibroids to shrink, and relieving the symptoms of women with fibroids. In certain embodiments, UAE can also be used to stop severe pelvic bleeding caused, for example, by trauma, malignant gynecological tumors or hemorrhage after childbirth.

d. Benign Prostatic Hyperplasia

In further specific embodiments, methods are provided for managing or treating benign prostatic hyperplasia (BPH) or a symptom thereof. The most frequent obstructive urinary symptoms are hesitancy, decreased urinary stream, intermittency, sensation of incomplete emptying, nocturia, frequency and urgency.

In certain embodiments, the management or treatment of BPH can be accomplished by embolization such as prostatic artery embolization (PAE) or transcatheter arterial embolization (TAE) using the microspheres and compositions provided herein.

In some embodiments, a catheter (e.g., a microcatheter) can be inserted into the right and/or left inferior vesicle arteries under the guidance of an x-ray camera (e.g., a fluoroscope). In certain embodiments, the catheter can be advanced as far as necessary to allow complete blockage of the blood vessels to the prostate, while sparing as many arterial branches that arise from the prostate artery and supply normal structures as possible.

In certain embodiments, angiography (e.g., initial pelvic angiography or selective digital subtraction angiography) can be used in conjunction with embolization to evaluate the iliac vessels and prostate arteries during the arterial and late phases, or to assess the blood supply to the prostate. Once the desired catheter position is achieved, each artery can be embolized by administration of the microspheres and compositions as described above. The administered microspheres can block the arteries that provide blood flow, reducing the prostate size, and relieving the symptoms of BPH. In certain embodiments, embolization can also be used to control massive hemorrhage after prostatectomy or prostate biopsy.

3. Diagnostic Imaging

As discussed above, the microspheres provide herein may be used in connection with diagnostic imaging, therapeutic imaging and therapeutic drug delivery, including, for example, ultrasound (US), magnetic resonance imaging (I), nuclear magnetic resonance (NMR), computed tomography (CT), electron spin resonance (ESR), nuclear medical imaging, optical imaging, elastography, drug delivery with ultrasound, radiofrequency (RF) and microwave laser.

In certain embodiments, the microspheres provided herein are fluoroscopically visible. That is, in some embodiments, the microspheres are loaded with, associated with, or otherwise contain one or more suitable contrast agents, such as an ionic or non-ionic contrast agent.

In some embodiments, the microspheres provided herein comprise a non-ionic contrast agent. The contrast agent can be loaded on the microsphere, associated with the microsphere, absorbed by, adsorbed by or otherwise contained in or on the microsphere. Alternatively, the contrast agent is a carrier solution for the microsphere. In specific embodiments, the contrast agent, such as a non-ionic contrast agent, is loaded within the microsphere (e.g., by mixing of otherwise contacting the contrast agent with the microspheres). In other embodiments, the microspheres do not comprise a contrast agent, such as a non-ionic contrast agent.

The non-ionic contrast agents can be an X-ray, CT, MRI contrast agent, or a combination thereof. The contrast agent can be paramagnetic or superparamagnetic. In some embodiments, the contrast agent is an X-ray contrast agent (also referred to as fluoroscopic agent or radio-opaque) or a CT contrast agent. In certain embodiments, the agent contains iodine. The non-ionic contrast agents can be monomeric, dimeric, or polymeric.

Examples of non-ionic contrast agents include, without limitation, metrizamide, iopamidol (Isovue™ or Iopamiron™), iodixanol (Visipaque™), iohexyl (Omnipaque™), iopromide (Ultravist™), iobtiridol, iomeprol, iopentol, iopamiron, ioxilan, iotrolan, gadodiamide, gadoteridol, iotrol, ioversol (Optiray™) or combinations thereof. In certain embodiments, the contrast agent is iopamidol. In specific embodiments, non-ionic contrast agent isiodixanol, iohexyl, iopromide, or ioversol. In another embodiment, the non-ionic contrast agent is gadodiamide or gadoteridol.

Further examples of suitable contrast agents for use in combination with the present stabilizing materials include stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. The transition, lanthanide and actinide elements can include, for example, Gd(III), Mn(II), Cu(II), Cr(III), Fe(II), Fe(III), Co(II), Er(II), Ni(II), Eu(III) and Dy(III). In some embodiments, the elements are Gd(III), Mn(II), Cu(II), Fe(II), Fe(III), Eu(III) and Dy(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Complexing agents can include, for example, diethylenetriaminepentaacetic acid (DTPA), ethylenediaminetetraacetic acid (EDTA), 1,4,7,10-tetraazacyclododecane-N,N',N',N'''-tetraacetic acid (DOTA), 1,4,7,10-tetraazacyclododecane-N,N',N'''-triacetic acid (DOTA), 3,6,9-triaza-12-oxa-3,6,9-tricarboxymethylene-10-carboxy-13-phenyltridecanoicacid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N'''-triacetic acid (NOTA), 1,4,8,11-tetraazacyclotetradecane-N,N',N'', N'''-tetraacetic acid (TETA), kryptands (macrocyclic complexes), and desferrioxamine. In some embodiments, the complexing agents are EDTA, DTPA, DOTA, DOTA and kryptands, such as DTPA. Lipophilic complexes can include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxyoctadecylamidomethyl-N-2,3-dihydroxypropyl)ethylenediamine-N,N'-diacetate (EDTA-ODP); and N,N'-Bis(carboxy-laurylamidomethyl-N-2,3-dihydroxypropyl)ethylenediamine-N,N'-diacetate (EDTA-LDP); including those described in U.S. Pat. No. 5,312,617, the disclosure of which is hereby incorporated herein by reference in its entirety. Proteinaceous macromolecules can include, for example, albumin, collagen, polyarginine, polylysine, polyhistidine, γ-globulin and β-globulin. In certain embodiments, the proteinaceous macromolecule is an albumin, polyarginine, polylysine or polyhistidine. Suitable complexes therefore include Mn(II)-DTPA, Mn(II)-EDTA, Mn(II)-DOTA, Mn(II)-DOTA, Mn(II)-kryptands, Gd(III)-DTPA, Gd(III)-DOTA, Gd(III)-DOTA, Gd(III)-kryptands, Cr(III)-EDTA, Cu(II)-EDTA, or iron-desferrioxamine. In specific embodiments, the complexes are Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. Nitroxides can be designed to coat the perimeters of the microspheres, for example, by making alkyl derivatives thereof, the resulting correlation times can be optimized. Moreover, the resulting contrast medium may be viewed as a magnetic sphere, a geometric configuration which maximizes relaxivity.

Exemplary superparamagnetic contrast agents suitable for use in the compositions herein include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the microspheres and/or stabilizing materials. With respect to vesicles, the contrast agents may be entrapped within the internal void thereof, administered as a solution with the microspheres, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the microspheres. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage.

The microspheres provided herein may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microspheres and have very high bulk susceptibilities and transverse relaxation rates. The larger particles, for example, particles having diameters of about 100 nm, have much higher $R_2$ relaxivities as compared to $R_1$ relaxivities. The smaller particles, for example, particles having diameters of about 10 to about 15 nm, have somewhat lower $R_2$ relaxivities, but much more balanced $R_1$ and $R_2$ values. Much smaller particles, for example, monocrystalline iron oxide particles having diameters of about 3 to about 5 nm, have lower $R_2$ relaxivities, but probably the most balanced $R_1$ and $R_2$ relaxation rates. Ferritin can also be formulated to encapsulate a core of very high relaxation rate superparamagnetic iron.

The iron oxides may simply be incorporated into the stabilizing materials and/or microspheres. In specific embodiments, the iron oxides may be incorporated into the walls of the microspheres, for example, by being adsorbed onto the surfaces of the microspheres, or entrapped within the interior of the microspheres.

E. Kits

Also provided herein are pharmaceutical packs and kits comprising one or more containers filled with one or more of the ingredients of the compositions provided herein. The kits can comprise, for example, microspheres and one or more additional components, wherein one, two, three or more of the components can be in one, two, three or more vials. In certain embodiments the microspheres are provided in the form of a dry powder. In other embodiments, the microspheres are provided in a biocompatible carrier, for example as an emulsion or suspension.

In certain embodiments, the container is a syringe (e.g., a polycarbonate, polypropylene, or cyclic olefin polymer (COP) syringe). In specific embodiments, the syringe has low moisture loss, which can result in an increased shelf-life (e.g., 2 to 3 years or longer) for pre-filled syringe embodiments of the kits provided herein. In a specific embodiment, microspheres provided herein are contained within a sterile syringe, such as a sterile pre-filled syringe (e.g., a 20 cc syringe), that is optionally provided in a peel-away pouch. In certain embodiments, the syringe comprises about 1 ml, 2 ml, 3 ml or 4 ml of the microspheres in a pharmaceutically acceptable carrier, such as saline (e.g., a non-pyrogenic or pyrogen-free, sterile physiological saline).

In other embodiments, the microspheres provided herein are contained within a vial. In specific embodiments, the vial is a glass vial with a screw-off cap (e.g., a 5 ml glass vial), that is optionally packaged in a peel-away pack comprising one or more additional vials. In specific embodiments, the vial comprises 1 ml or 2 ml of the microspheres in a pharmaceutically acceptable carrier, such as saline (e.g., a non-pyrogenic or pyrogen-free, sterile physiological saline).

Associated with such container(s) can be a notice in the form prescribed by a governmental agency regulating the manufacture, use or sale of pharmaceuticals or biological products, reflecting approval by the agency of the manufacture, use or sale of the product for patient (e.g., human or other mammal) administration. Also associated with such container(s) can be instructions for use. The reagents of any of the methods described herein can also be included as components of a kit.

In one kit format, the microspheres provided herein are present in a liquid, physiologically compatible solution in one vial. In another kit format, the microspheres of the provided herein are present in dry form in one vial. In certain kit formats comprising multiple components in multiple vials, the contents of the vials can be mixed together prior to or concurrently with administration. In some embodiments, the microspheres are suspended in a suitable liquid prior to administration, or optionally a second vial is provided, which contains the injectable solution and the contents of both vials are combined prior to administration or concurrently with administration.

Finally, in another kit format the microspheres provided herein are present in one vial and a second vial contains a pharmaceutically acceptable solution comprising the contrast agent. The microspheres can then be mixed together with the contrast agent, for example, prior to or concurrently with administration.

The following examples are offered by way of illustration, and not by way of limitation.

EXAMPLES

The practice of the invention employs, unless otherwise indicated, conventional techniques in molecular biology, organic chemistry, biochemistry and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates).

Example 1

Synthesis of an Ultra-Pure Diethylaminoethylacrylamide Monomer

An ultra-pure diethylaminoethylacrylamide monomer was synthesized according to the following scheme:

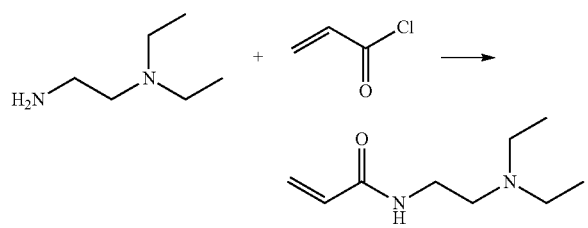

Briefly, acryloyl chloride was dissolved in $CH_2Cl_2$ and cooled to 0° C. N,N-Diethylethylenediamine dissolved in $CH_2Cl_2$ was added drop wise at $T_i$=0-5° C. followed by NaOH (~15% aq. solution). The reaction mixture was stirred for 15 min and the layers were separated. The organic layer was washed with water and $NaHCO_3$ solution and dried over $MgSO_4$. The suspension was filtered and concentrated under reduced pressure and stabilized by BHT.

Example 2

HPLC Analysis of a Diethylaminoethylacrylamide Monomer

First, the standard solutions were prepared as follows, with MBA chosen as an internal reference control:

Stock Solutions

DEAE stock solution: approximately 200 mg (or 250 mg) of DEAE was weighed in a 200 mL (or 250 mL) reference flask and dissolved in pure water (Purelab). The pH of the solution was adjusted to 2 by 1N HCl. The solution was adjusted with water to a concentration of 1000 ppm (mg/L).

MBA stock solution: approximately 200 mg (or 250 mg) of MBA was weighed in a 200 mL (or 250 mL) reference flask and dissolved in pure water. The solution was then subjected to ultrasonication for 15 min and let return to room temperature. The solution was adjusted to a concentration of 1000 ppm (mg/L).

Intermediate solution: an intermediate solution was prepared by diluting 5 mL of the 1000 ppm solution with water to a final volume of 50 mL. Also prepared were 20, 40, 60, 80, 100 ppm.

The injected solutions are listed in Table 1. The exact concentrations of the solutions were noted.

TABLE 1

| | Injected solutions | | | |
|---|---|---|---|---|
| Solution | DEAE solution concentration | DEAE solution volume | MBA solution volume | Total volume |
| Standard 1 | 20 | 4 | 1 | 5 |
| Standard 2 | 40 | 4 | 1 | 5 |
| Standard 3 | 60 | 4 | 1 | 5 |
| Standard 4 | 80 | 4 | 1 | 5 |
| Standard 5 | 100 | 4 | 1 | 5 |

The samples to be analyzed were prepared as follows:

Stock solutions: approximately 200 mg (or 250 mg) of DEAE was weighed in a 200 mL (or 250 mL) reference flask and dissolved in pure water (Purelab). The pH of the solution was adjusted to 2 by 1N HCl. The solution was adjusted with water to a concentration of 1000 ppm (mg/L). Three stock solutions were prepared and tested.

Intermediate solution: an intermediate solution was prepared by diluting 5 ml of the 1000 ppm solution with water to a final volume of 50 mL.

Sample solutions: sample solutions were prepared by diluting the intermediate solutions to approximately 60 ppm (at least 5 mL for sample injection). The intermediate solution (100 ppm) was also tested. The exact concentrations were recorded.

The solutions (standards and samples) were then transferred to the HPLC vials on the support of the injector for analysis. The settings of the HPLC are listed in Table 2.

TABLE 2

| HPLC settings | |
|---|---|
| Parameters | Settings |
| Injection Volume | 20 µL |
| Oven Temperature | 30° C. |

TABLE 2-continued

| HPLC settings | |
|---|---|
| Parameters | Settings |
| Mobile phase | Methanol/water (0.1% TFA) 10/90 |
| Analysis time | 6 min |
| Wavelength | 230 nm |
| Column | C18; 100 × 4.6 mm, 5 μm. |
| Flow | 1 mL/min |

The results of HPLC analysis are shown m FIG. 1A, which depicts the sensitivities of purity observed using a bromination reaction (right bars, as provided by manufacturer BioSepra) and HPLC (left bars) for given lots of DEAE monomer (T209, U088 and U089) obtained from BioSepra.

Example 3

Bromine Test of a Diethylaminoethylacrylamide Monomer

A test sample (0.1 g) containing diethylaminoethylacrylamide is added to carbon tetrachloride (2 mL). A 5% solution of bromine in carbon tetrachloride is added drop by drop, with shaking, until the bromine color persists. The bromine test is sensitive to the presence of C=C bond, which can indicate the approximate content of diethylaminoethylacrylamide present in the test sample.

Example 4

Synthesis of an Ultra-Pure N-Tris-Hydroxymethyl Methylacrylamide Monomer

An ultra-pure N-tris-hydroxymethyl methylacrylamide monomer was synthesized according to the following scheme:

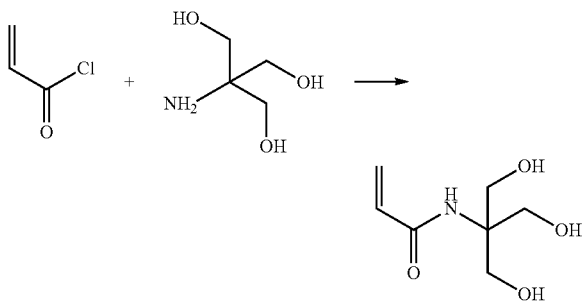

Briefly, acryloyl chloride was dissolved in $CH_2Cl_2$ and cooled to 0° C. N-(TrisHydroxy)methyl amine dissolved in $CH_2Cl_2$ was added drop wise at $T_i$=0-5° C. followed by NaOH (~15% aq. solution). The reaction mixture was stirred for 2 hours. The N-tris-hydroxymethyl methylacrylamide was removed after re-crystallization in water.

Example 5

HPLC Analysis of N-Tris-Hydroxymethyl Methylacrylamide Monomer

First, a standard curve was prepared using N-[Tris (hydroxymethyl)methyl]acrylamide(trisacryl) with at least 98% purity (provided by SAFC; information from manufacturer's purity certificate).

Stock solution: approximately 200 mg (or 250 mg) of trisacryl was weighed in a 200 mL (or 250 mL) reference flask and dissolved in pure water. The solution was then subjected to ultrasonication for 15 min and let return to room temperature. The solution was adjusted to a concentration of 1000 ppm (mg/L).

Intermediate solution: an intermediate solution was prepared by diluting 5 ml of the 1000 ppm solution with water to a final volume of 50 mL.

The injected solutions are listed in Table 3. The exact concentrations of the solutions were noted.

TABLE 3

| | Injected solutions | | | |
|---|---|---|---|---|
| Solution | Concentration (ppm) | Intermediate solution volume | Water volume | Total volume |
| Standard 1 | 20 | 1 | 4 | 5 |
| Standard 2 | 40 | 2 | 3 | 5 |
| Standard 3 | 60 | 3 | 2 | 5 |
| Standard 4 | 80 | 4 | 1 | 5 |
| Standard 5 | 100 | 5 | 0 | 5 |

The samples to be analyzed were prepared as follows:

Stock solution: approximately 200 mg (or 250 mg) of trisacryl was weighed in a 200 mL (or 250 mL) reference flask and dissolved in pure water. The solution was then subject to ultrasonication for 15 min and let return to room temperature. The solution was adjusted to a concentration of 1000 ppm (mg/L). Three solutions are prepared and tested.

Intermediate solution: an intermediate solution was prepared by diluting 5 ml of the 1000 ppm solution with water to a final volume of 50 mL.

Sample solutions (each solution): sample solutions were prepared by diluting the intermediate solutions to approximately 60 ppm (at least 5 mL for sample injection). The intermediate solution (100 ppm) was also tested. The exact concentrations were recorded.

The solutions (standards and samples) were then transferred to the HPLC vials on the support of the injector for analysis. The settings of the HPLC are listed in Table 4.

TABLE 4

| HPLC settings | |
|---|---|
| Parameters | Settings |
| Injection Volume | 20 μL |
| Oven Temperature | 30° C. |
| Mobile phase | Methanol/water 20/80 (0.2% TFA) |
| Analysis time | 6 min |
| Wavelength | 230 nm |
| Column | C18; 250 × 4.6 mm, 5 μm. |
| Flow | 1 mL/min |

Figure 1B:
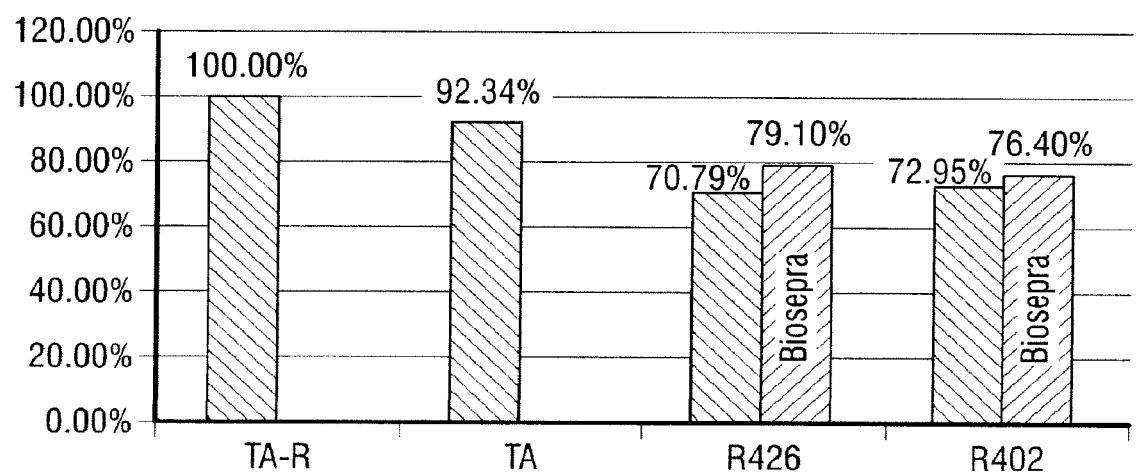

The results of HPLC analysis showing the purity of trisacryl from different sources are shown in FIG. 1B. FIG. 1B depicts the sensitivities of purity for two different lots of trisacryl (R426 and R402 obtained from BioSepra) observed using a bromination reaction (right bars, as provided by manufacturer) or HPLC (left bars). The data are shown with an assumption of 100% purity of a recrystallized trisacryl (TA-R) obtained and compared with trisacryl monomer from SAFC prior to recrystallization (TA) (see below). The TA-R was prepared by recrystallizing TA (trisacryl from SAFC) in water and then dried. NMR $^1H$ analysis was performed on the recrystallized TA-R sample, and no organic impurities were detected on the NMR $^1$H spectrum (data not shown). Additionally, an elemental analysis was performed on the TA-R sample to check if there was inorganic salts present. The theoretical result for 100% pure trisacryl is C 47.99%, H 7.48%, N 8.00% and O 36.53%. It was found for the TA sample obtained from SAFC: C 46.76% H 7.39% and N 7.86% and TA-R 48.14%, H 7.63% and N 8.07%, so the assumption was made that the TA-R sample was close to 100% pure. Each of the R426, R402 TA and TA-R samples were then tested by HPLC analysis, and the spectra were recorded at 232 nm. For all the samples analyzed, there was good linearity between the pic area and the concentration (data not shown). With the assumption that TA-R was about 100% pure, the gradient of each line was taken to define the HPLC purity of each trisacryl sample. The results of the HPLC analyses of the TA and TA-R samples are shown in FIG. 1B as discussed above.

Example 6

Bromine Test of N-Tris-Hydroxymethyl Methylacrylamide Monomer

A test sample (0.1 g) containing N-tris-hydroxymethyl methylacrylamide is added to carbon tetrachloride (2 mL). A 5% solution of bromine in carbon tetrachloride is added drop by drop, with shaking, until the bromine color persists. The bromine test is sensitive to the presence of C=C bond, which can indicate the approximate content of N-tris-hydroxymethyl methylacrylamide present in the test sample.

Example 7

Microsphere Preparation Using an Ultra-Pure N-Tris-Hydroxymethyl Methylacrylamide Monomer NaCl (58 g) and sodium acetate (27.2 g) were solubilized in water (300 mL) under stirring in a one liter beaker. Glycerol (400 mL) was added and the pH of the solution was adjusted to 6 with acetic acid. This solution was then heated at 60° C. under stirring and three monomers were added to the solution. The monomer materials were not 100% pure and the amount of each monomer used in the following steps was weighed with an adjustment of the amount of impurities present in the materials. Assuming that the monomers were 100% pure, the quantities of each monomer were as follows:

N,N-methylene-bis-acrylamide: 10 g.

Diethylaminoethylacrylamide: 35 g

N-tris-hydroxymethyl methylacrylamide: 90 g

Porcine gelatin (PB Leiner; Vilvoorde, Belgium): 20 g.

Diethylaminoethylacrylamide was supplied by Pall BioSepra, France. The purity of diethylaminoethylacrylamide was greater than 80% according to Pall BioSepra's specification.

N-tris-hydroxymethyl methylacrylamide was supplied by Pall BioSepra and Sigma Aldrich Fine Chemicals (SAFC)). According to suppliers' product specification, the purity of N-tris-hydroxymethyl methylacrylamide supplied by Pall BioSepra and SAFC is greater than 76% and 93%, respectively (see Table 5). Other comparative data of N-tris-hydroxymethyl methylacrylamide supplied by PALL Biosepra and SAFC are provided in Table 5.

TABLE 5

Comparative data of N-tris-hydroxymethyl methylacrylamide supplied by PALL Biosepra and SAFC

| Trisacryl Specification | PALL Biosepra | SAFC |
| --- | --- | --- |
| IR spectroscopy | Conform to structure | Conform to structure |
| Moisture | <5% | No |
| Purity | >76% | >93% |
| Nitrogen content | No | C, H, N analysis; carbon 44.6-51.4%, nitrogen 7.4-8.6% |
| NMR Analysis | No | Conform to structure |
| HPLC | No | Yes |
| Cl dosage | No | KCl <5% |

When the solution was clear, a solution of gelatin (25 g) in water (250 ml) was added to the monomer solution. This solution was filtered and placed under stirring at 60° C. (Solution A). A solution of ammonium persulfate (3.5 g) in water (101.6 g) was also prepared (Solution B). In a 10 liters beaker, oil (4 L) and Arlacel (3.1 g) were stirred at 60° C. (Solution C). Solution A and solution B were injected through pump Q2 and pump RHO, respectively, in the Feed Ring equipment placed in solution C. After the injection was completed, the solution was stirred at 125 rpm for 30 minutes at 60° C. The reaction was stopped by adding a cold solution of water, ice and surfactant. The microspheres obtained were washed several times with water until the oil was completely removed. The beaker was placed in an ultrasound bath for 10 minutes to reduce the number of sticking microspheres. The microspheres were then heated at 37° C. and 300 ml of glutaraldehyde was added per 1 L of microspheres for gelatin crosslinking. The microspheres were washed again twice with water. The microspheres were then recovered by decanting, washed carefully, screened and sterilized in an autoclave in a buffered medium.

Example 8

Microsphere Preparation Using an Ultra-Pure N-Tris-Hydroxymethyl Methylacrylamide Monomer and an Ultrapure Diethylaminoethylacrylamide Monomer NaCl (58 g) and sodium acetate (27.2 g) were solubilized in water (300 mL) under stirring in a 1 liter beaker. Subsequently, glycerol (400 mL) was added and the pH of the solution was adjusted to 6 with acetic acid.

This solution was heated at 60° C. under stirring and two of the three monomers were added to the solution. The monomer materials were not 100% pure and the amount of each monomer used in the following steps was weighed with an adjustment of the amount of impurities present in the materials. Assuming that the monomers were 100% pure, the quantities of each monomer were as follows:

N,N-methylene-bis-acrylamide: 10 g.

N-tris-hydroxymethyl methylacrylamide: 90 g

Diethylaminoethylacrylamide: 35 g

Porcine gelatin (PB Leiner; Vilvoorde, Belgium): 20 g.

N-tris-hydroxymethyl methylacrylamide was supplied by Pall BioSepra and SAFC. According to suppliers' product specification, the purity of N-tris-hydroxymethyl methylacrylamide supplied by Pall BioSepra and SAFC is greater than 76% and 93%, respectively (see Table 5). Other comparative data of N-tris-hydroxymethyl methylacrylamide supplied by PALL Biosepra and SAFC are provided in Table 5.

Diethylaminoethylacrylamide was supplied by PALL Biosepra and SAFC. According to suppliers' product specification, the purity of diethylaminoethylacrylamide supplied by Pall BioSepra and SAFC is greater than 80% and 95%, respectively. Other comparative data of diethylaminoethylacrylamide supplied by PALL Biosepra and SAFC are provided in Table 6:

TABLE 6

Comparative data of diethylaminoethylacrylamide supplied by PALL Biosepra and SAFC

| DEAE Acrylamide Specification | PALL Biosepra | SAFC |
|---|---|---|
| IR spectroscopy | Conform to structure | Conform to structure |
| Moisture | <5% | No |
| Purity | >80% | >95% |
| Nitrogen content | 11-14% | No |
| NMR Analysis | No | Conform to structure |
| HPLC | No | Yes |
| Gas Chromatography | No | Yes |

The third monomer, diethylaminoethylacrylamide, was added after its preparation. Diethylaminoethylacrylamide (35 g) was diluted with water (17 g). This solution was placed in an ice cold bath and the pH of the solution was adjusted to 2 with HCl. This solution was added to the solution containing the other two monomers.

When the solution was clear, gelatin (25 g) in water solution (250 mL) was added to the above monomer solution. This solution was filtered and placed under stirring at 60° C. (solution A). Ammonium persulfate (3.5 g) in water (101.6 g) was also prepared (Solution B). In a 10 liters beaker, oil (4 L) and Arlacel (3.1 g) were stirred at 60° C. (Solution C). Solution A and solution B were injected through pump Q2 and pump RHO, respectively, in the Feed Ring equipment placed in solution C. After the injection was completed, the solution was stirred at 125 rpm for 30 minutes at 60° C. The reaction was stopped by adding a cold solution of water, ice and surfactant. The microspheres obtained were washed several times with water until the oil was completely removed and the beaker was placed in an ultrasound bath for 10 minutes to reduce the number of sticking microspheres. The microspheres were then heated at 37° C. and 300 ml of glutaraldehyde was added per 1 L of microspheres for gelatin crosslinking. The microspheres were washed again twice with water. The microspheres were then recovered by decanting, washed carefully, screened and sterilized in an autoclave in a buffered medium.

Example 9

Preparation of Colored Microsphere Using Ultra-Pure Monomers

Microspheres (100 mL) obtained according to Examples 7 or 8 above were washed with a borate buffer (0.1M, pH 8) and then suspended in an erythrosine isothiocyanate solution (50 mL, 5 mg/mL). The suspension was then stirred for at least 15 hours, after which it was washed with a neutral buffer to a colorless supernatant. The red-colored microspheres were then calibrated and sterilized, and can be used in percutaneous embolization.

Example 10

Preparation of Opaque Preparation Using Ultra-Pure Monomers

The procedure of Examples 7 or 8 is followed, adding barium sulfate power (200 g) to the initial monomer. The microspheres obtained are opaque to both visible light and x-rays.

Example 11

Preparation of Magnetic Microsphere Using Ultra-Pure Monomers

The procedure of Examples 7 or 8 is followed, adding 50 mg of magnetite (e.g., $Fe_3O_4$) to the initial monomer solution. Alternatively, microspheres obtained according to Examples 7 and 8 can each be packed into a 16 mm diameter chromatographic column and washed with a physiological buffer. The column is then loaded with a colloidal suspension of ferrofluid (very small particles of magnetite) at a flow rate of 10 mL/hour. Particles of magnetite are adsorbed by the microspheres and permanently trapped. Resulting microspheres can be used for regular embolization procedure and have magnetic properties, for example, can be detected in Magnetic Resonance Imaging (MRI) imagery.

Example 12

Separation of Non-Sticking Microspheres by Ultrasonication

Microspheres made from N-tris-hydroxymethyl methylacrylamide, diethylaminoethylacrylamide, N,N-methylene-bis-acrylamide and TEMED were processed following different methods. Ultrasonication was done one or two times in a 35 KHz ultrasonic bath for approximately 10-15 minutes.

Figure 2A:
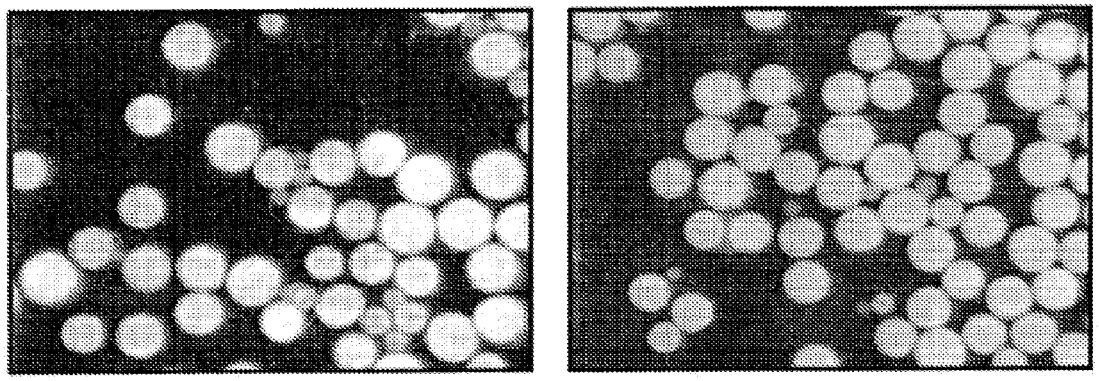
FIGS. 2A-2C illustrate the reduction of sticking microspheres by ultrasonication. The image analyses shows a significant decrease of sticking microspheres by ultrasonication. No broken microspheres were observed by this method.
Figure 2B:
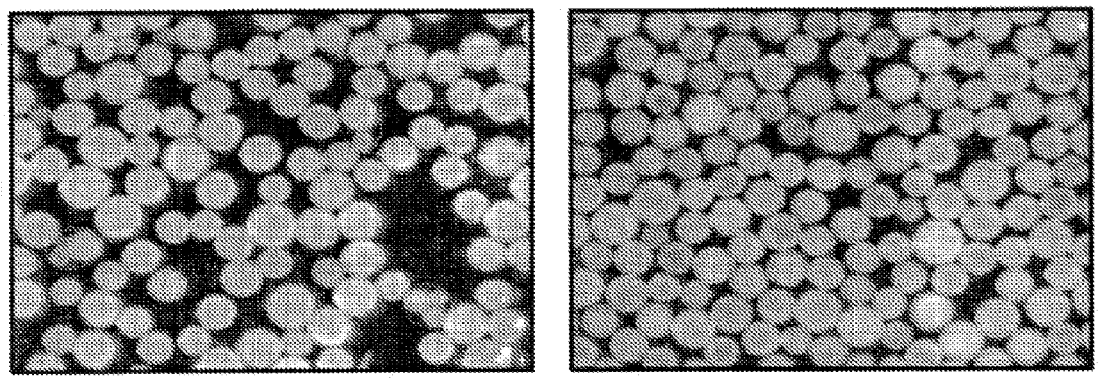
Figure 2C:
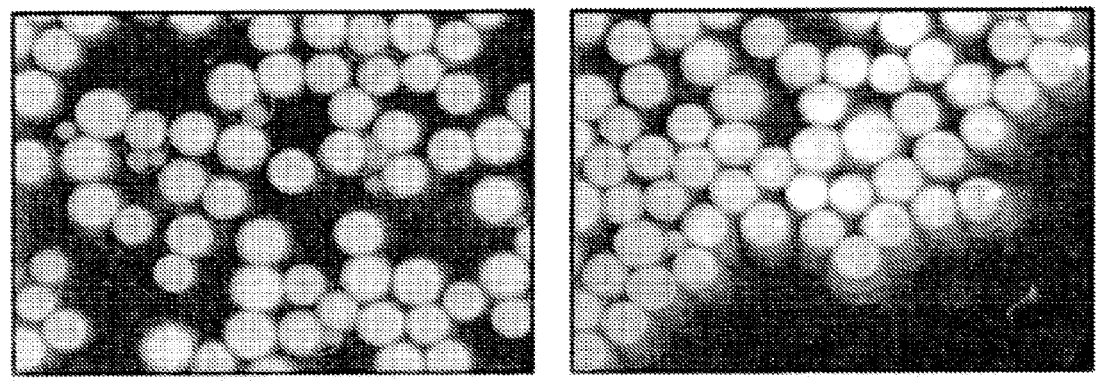

FIGS. 2A-2C illustrate the reduction of sticking microspheres by ultrasonication. FIG. 2A shows microspheres before crosslinking, initially (left panel) and after 15 min of ultrasonication (right panel). The percentage of sticking microspheres decreases from about 7% to about 0.2% with ultrasonication. FIG. 2B demonstrates a second batch of microspheres (divided into two fractions) after crosslinking without (left panel) or with (right panel) ultrasonication prior to crosslinking Sieving was done after the ultrasonication step. The percentage of sticking microspheres decreases from about 3% to nearly about 0% with ultrasonication. FIG. 2C shows microspheres before crosslinking, initially (left panel) and after 2×15 min. of ultrasonication (right panel). The percentage of sticking microspheres decreases from about 9.2% to about 1.6% with ultrasonication.

Taken together, in all cases, the microspheres showed less sticking spheres when ultrasonication is applied (FIGS. 2A-2C, right panels) as compared to no ultrasonication (FIGS. 2A-2C, left panels). No broken microspheres were observed by this method.

Figure 3A:
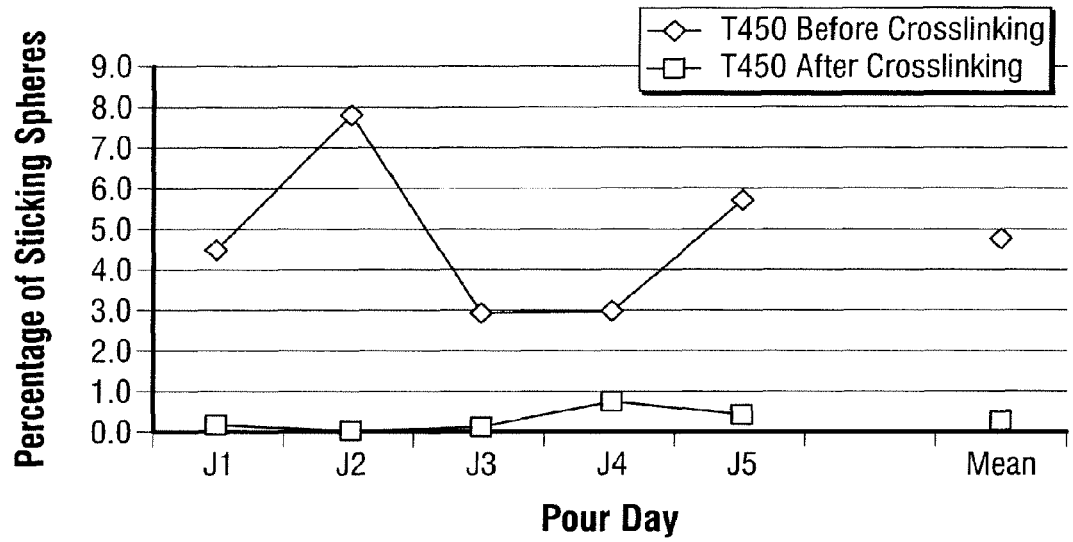
FIGS. 3A-3C illustrate the percentages of sticking microspheres subject to ultrasonication before (FIG. 3A) and after gelatin crosslinking (FIG. 3B). Sieving was made after the ultrasonication step, and the percentage of volume on sieve is shown in FIG. 3C.
Figure 3B:
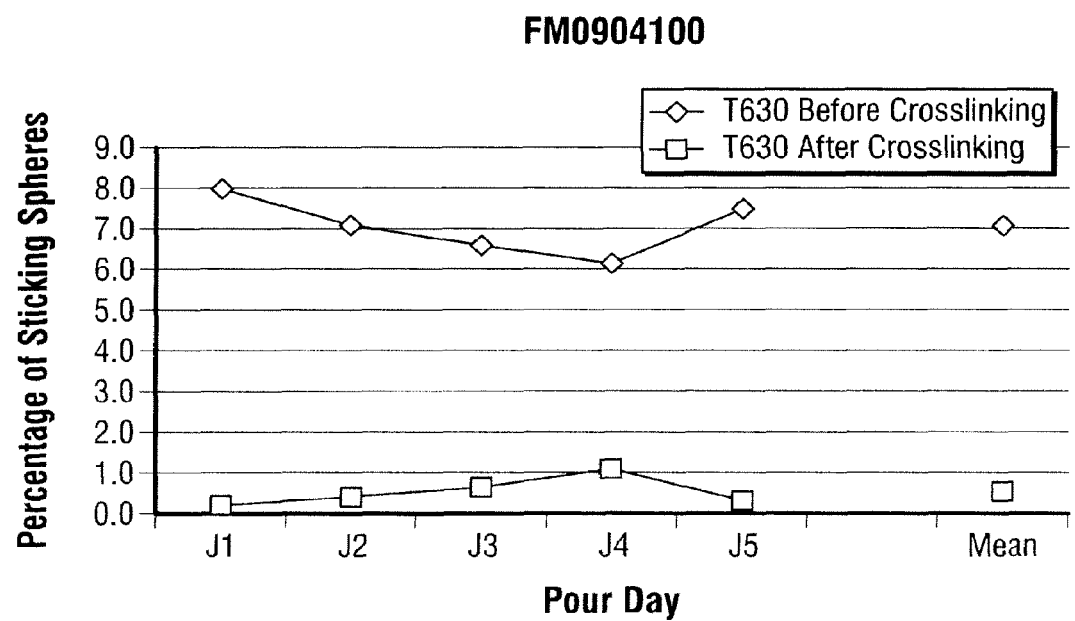

Table 7 and FIG. 3 depict results from a separate experiment and also further illustrates reduced percentages of sticking microspheres (lot FM0904100) subject to ultrasonication before (FIG. 3A) and after gelatin crosslinking (FIG. 3B).

TABLE 7

| | Pour Day 1 | Pour Day 2 | Pour Day 3 | Pour Day 4 | Pour Day 5 | Mean |
|---|---|---|---|---|---|---|
| Ultrasonic step | Yes | Yes | Yes | Yes | Yes | |
| % of sticking spheres; T450 before crosslinking | 4.5 | 7.8 | 2.9 | 3.0 | 5.7 | 4.8 |
| % of sticking spheres; T450 after crosslinking | 0.2 | 0.4 | 0.7 | 1.1 | 0.3 | 0.3 |

TABLE 7-continued

|  | Pour Day 1 | Pour Day 2 | Pour Day 3 | Pour Day 4 | Pour Day 5 | Mean |
|---|---|---|---|---|---|---|
| % of sticking spheres; T630 before crosslinking | 8.0 | 7.1 | 6.6 | 6.1 | 7.5 | 7.1 |
| % of sticking spheres; T630 after crosslinking | 0.2 | 0.4 | 0.7 | 1.1 | 0.3 | 0.6 |

Figure 3C:
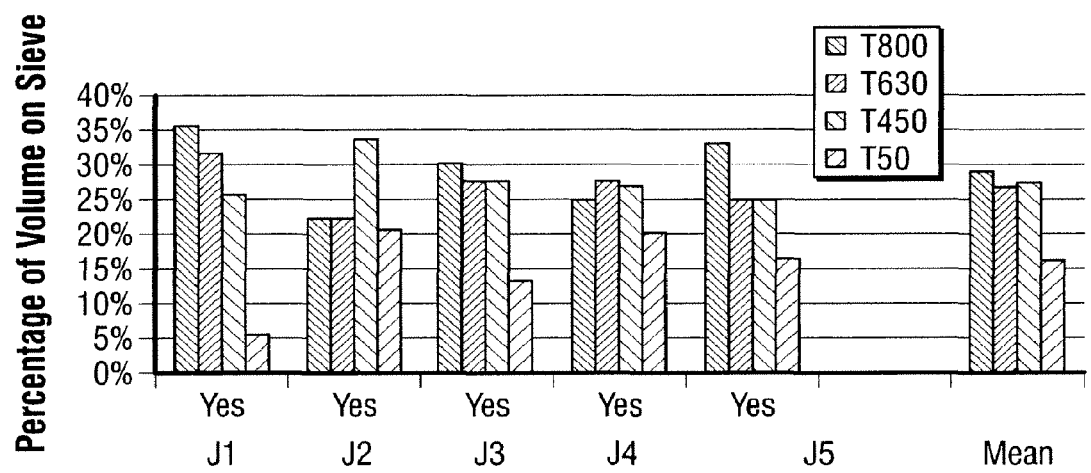

Sieving was done after the ultrasonication step, and the percentage of volume on an 800 µm, 630 µm, 450 µm or 50 µm sieve is shown in Table 8 and FIG. 3C.

TABLE 8

|  | Pour Day 1 | Pour Day 2 | Pour Day 3 | Pour Day 4 | Pour Day 5 | Total |
|---|---|---|---|---|---|---|
| T800 | 18 | 14 | 38 | 33 | 40 | 143 |
| T630 | 16 | 14 | 35 | 37 | 30 | 132 |
| T450 | 13 | 21 | 35 | 37 | 30 | 135 |
| T50 | 3 | 13 | 35 | 36 | 30 | 80 |
|  |  |  |  |  |  |  |
| Total Volume | 50 | 62 | 125 | 133 | 120 | 490 |
| T800 | 36% | 23% | 30% | 25% | 33% | 29% |
| T630 | 32% | 23% | 28% | 28% | 25% | 27% |
| T450 | 26% | 34% | 28% | 27% | 25% | 28% |
| T50 | 6% | 21% | 14% | 20% | 17% | 16% |

Example 13

HR-MAS NMR Analysis of Monomers

The high resolution magic angle spinning ("HR-MAS") technique was employed to analyze the starting materials used herein for microsphere synthesis.

Preparation of Samples

Figure 7:
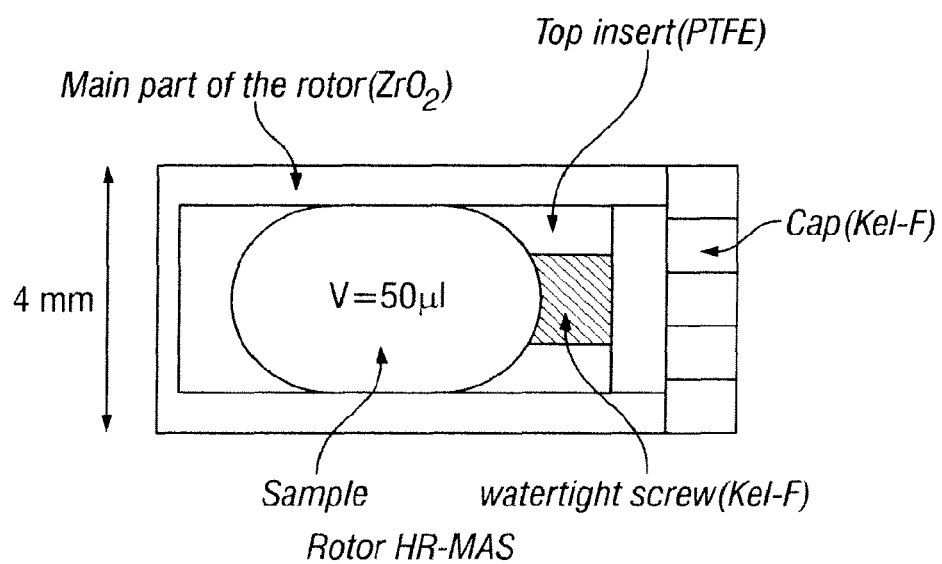
FIG. 7 illustrates a HR-MAS rotor used for the NMR analysis.

Trisacryl, porcine gelatin, DEAE-acrylamide and MBA samples (~15 mg each) were loaded in a HR-MAS rotor (see FIG. 7). Deuterated solvent was then added to obtain a total volume of 50 µL.

The rotors are referenced in Table 9.

TABLE 9

| Rotor | Sample | Mass | Solvent | Total Volume (µL) |
|---|---|---|---|---|
| 1.280 | Trisacryl | 15 | $D_2O$ | 50 |
| 1.281 | Gelatin | 12 | $D_2O$ | 50 |
| 1.282 | MBA | 15 | $D_2O$ | 50 |
| 1.274 | DEAE-acrylamide | 15 | $D_2O$ | 50 |

Analysis of sample by NMR spectroscopy

NMR spectra recorded on a Bruker Avance I spectrometer at 400 MHz ($^1H$) with a 4 mm HR-MAS probehead ($^1H$, $^{13}C$, $^2H$ lock).

Tuning

After adjustment of the magic angle of the probehead, the following adjustments were carried out for each sample:

Probehead tuning and matching ($^1H$)

90° pulse measurement $B_0$ homogeneity adjustment (shims)

Acquisition

All experiments were performed at room temperature (298 K). For each sample, a 1D $^1H$ NMR spectrum was recorded.

Processing

Acquisition and processing parameters are summarized in Table 10.

TABLE 10

| Acquisition Parameters | |
|---|---|
| Spectrometer/Probehead | Bruker Avance I, 400 MHz ($^1H$)/HRMAS |
| Temperature | 25° C. |
| Sample rotation | 4000 Hz |
| Lock substance | $D_2O$ |
| Pulse program | zgcppr |
| 90° $^1H$ pulse/(p1p11) | 6.35 µs/0 dB |
| Number of points (TD) | 32k |
| Acquisition time (AQ) | 1.98 s |
| Receiver gain (RG) | 90.5 |
| Relaxation delay ($d_1$) | 1.5 sec |
| Number of scans (NS) | 4096 |
| Spectral width (SW/SWh) | 20.69 ppm/1875.55 Hz |
| Carrier frequency (O1p/O1) | 4.7 ppm/1878.55 Hz |
| Processing parameters | |
| Number of points (SI) | 32k |
| Apodization | aucune |
| Baseline correction | Spline |

Results

Figure 4B:
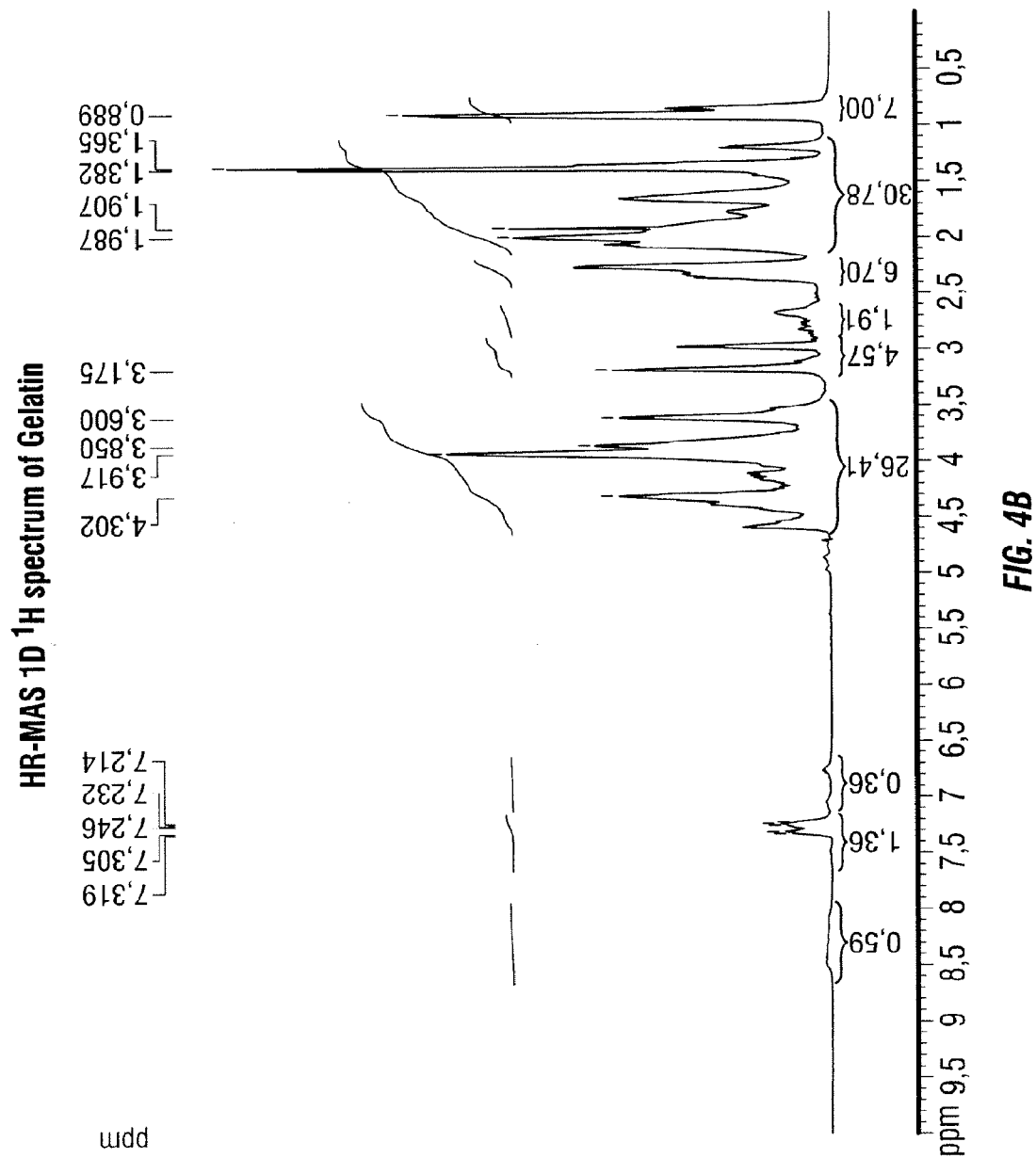
Figure 4C:
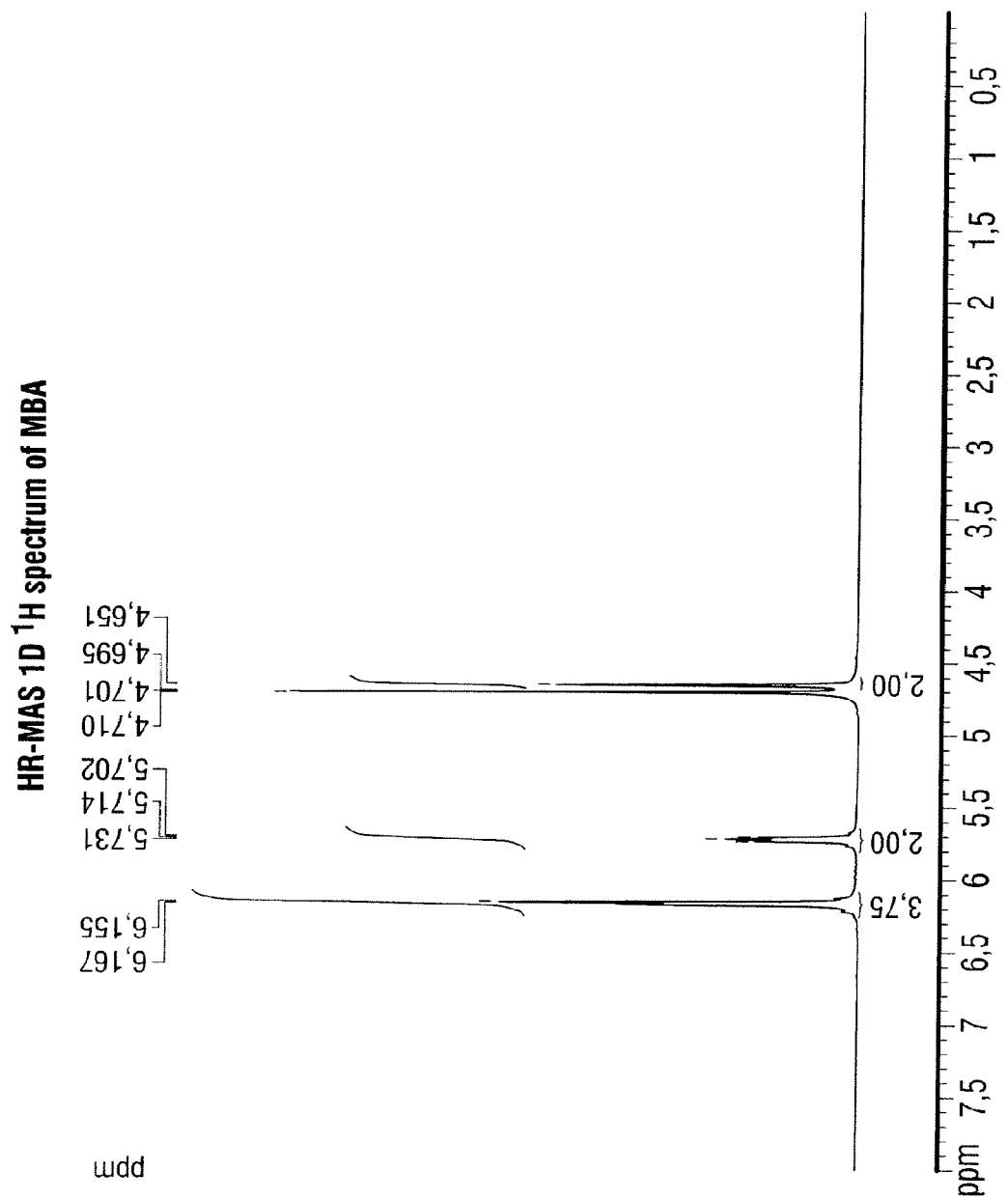
Figure 4E:
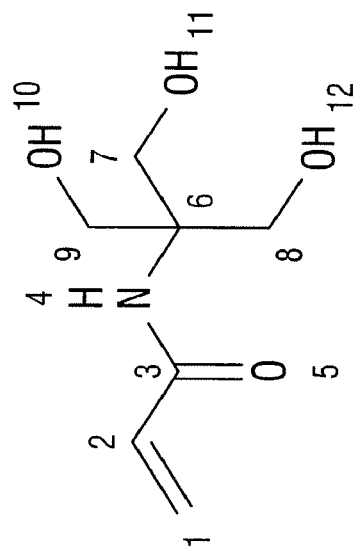
Figure 4F:
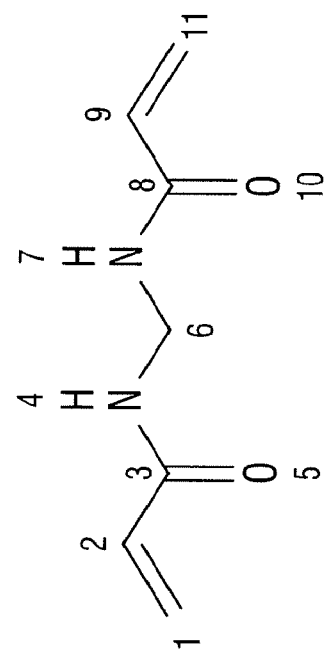
Figure 4G:
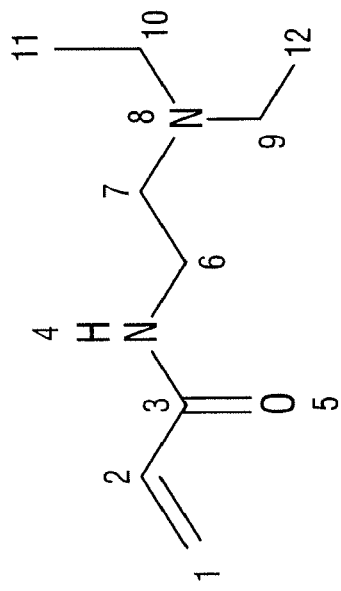

Typical signals for vinylic residues and aromatic moieties were identified in the spectra. The one dimensional $^1H$ NMR spectrum of trisacryl, gelatin, MBA and DEAE acrylamide are shown in FIGS. 4A-4D. The attribution of $^1H$ nuclei for trisacryl, MBA and DEAE acrylamide are shown in FIGS. 4E-4G. The 1D $^1H$ NMR spectrum for gelatin consists of peaks from 7.20 to 7.30 ppm, which can be attributed, for example, to the aromatic protons present in the amino acids.

Example 14

HR-MAS NMR Analysis of Microspheres

Microspheres prepared according to Example 8 using trisacryl and DEAE acrylamide from different sources (SAFC, PALL Biosepra) were analyzed by NMR spectroscopy.

Analysis of Sample by NMR Spectroscopy

Microsphere samples (~3 mg each) made of trisacryl and DEAE acrylamide from different sources. The SAFC FMP 128 microsphere sample was lab bench-prepared using trisacryl and DEAE obtained from SAFC (trisacryl lot 1443257, 96% purity; DEAE lot 585803-199, 98% purity). The PALL FMP 130 microsphere sample was lab-bench prepared using trisacryl and DEAE obtained from PALL Biosepra (trisacryl lot Y175; 90.9% purity; DEAE lot U089; 85% purity). The FM0903031-M1675 microsphere sample was manufactured using trisacryl obtained from SAFC (lot 03211DJ; 95.2% purity) and DEAE from PALL Biosepra (lot U089; 85.0% purity). The FM0903021-M1654 microsphere sample was manufactured using trisacryl and DEAE obtained from PALL Biosepra (trisacryl lot W299, 88.2% purity; DEAE lot U089; 85.0% purity). Purity levels were as provided by manufacturers' specifications. Each of the four samples were loaded into a rotor HR-MAS (see FIG. 7).

Deuterated ($D_2O$) solvent was then added to obtain a total volume of 50 µL.

The rotors are referenced in Table 11.

TABLE 11

| Rotor | Sample | Mass | Solvent | Total Volume (µL) |
|---|---|---|---|---|
| 1.270 | SAFC FMP 128 | 3 | $D_2O$ | 50 |
| 1.271 | PALL FMP 130 | 3 | $D_2O$ | 50 |

Tuning

After adjustment of the magic angle of the probehead, the following adjustments were carried out for each sample:
Probehead tuning and matching ($^1H$)
90° pulse measurement
$B_0$ homogeneity adjustment (shims)
Acquisition All experiments were performed at room temperature (25° C.). For each sample, a one-dimensional $^1H$ NMR spectrum was recorded.

Processing

Acquisition and processing parameters are summarized in Table 12.

TABLE 12

| Acquisition Parameters | |
|---|---|
| Spectrometer/Probehead | Bruker Avance I, 400 MHz ($^1H$)/HRMAS |
| Temperature | 25° C. |
| Sample rotation | 4000 Hz |
| Lock substance | $D_2O$ |
| Pulse program | zgcppr |
| 90° $^1H$ pulse/(p1p11) | 6.35 µs/0 dB |
| Number of points (TD) | 32k |
| Acquisition time (AQ) | 1.98 s |
| Receiver gain (RG) | 90.5 |
| Relaxation delay ($d_1$) | 1.5 sec |
| Number of scans (NS) | 4096 |
| Spectral width (SW/SWh) | 20.69 ppm/1875.55 Hz |
| Carrier frequency (O1p/O1) | 4.7 ppm/1878.55 Hz |
| Processing parameters | |
| Number of points (SI) | 32k |
| Apodization | aucune |
| Baseline correction | Spline |

Results

The results are shown in FIGS. 5A-5J. FIGS. 5A-5D illustrate the NMR spectra of samples SAFC FMP 128 and PALL FMP 130. FIGS. 5E-5J illustrate the NMR spectra of samples SAFC FMP 128, PALL FMP 130, FM0903031-M1675 and FM0903021-M1654.

Figure 5A:
Figure 5A:
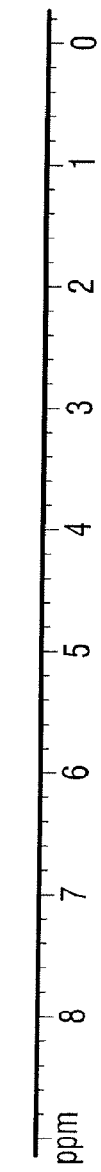

FIG. 5A is the superposition of the NMR spectra of two samples, which shows a similarity between the corresponding main peaks (marked as A, B and C) identified in the spectra. The assignment of peaks A, B and C and other minor peaks were based on the analysis of HR-MAS NMR spectra of starting materials from Example 13.

Peak A: identified at 3.77 ppm, which may be attributed, for example, to the tris-hydroxymethyl groups ($C(CH_2OH)_3$) in the copolymer.

Peak B: identified at 3.2 ppm, which may be attributed, for example, to the CH2 groups linked to the basic nitrogen atom ($CH_2N(CH_2CH_3)_2$). Without wishing to be bound by any theory, the difference in the chemical shift between the pure monomers in $D_2O$ and microspheres suggests that the amine is protonated (ammonium) in the crosslinked structure.

Peak C: identified at 1.3 ppm, which may be attributed, for example, to the groups in the beta position of the carboxamide group of the polymerized structure ($CH_2$—CHCONH). The relative integration ratios of peak B to peak A and peak C to peak A were carried out using a semi-quantitative approach by integration of the surface of the peaks and summarized in Table 13.

TABLE 13

| Sample | A | B | C |
|---|---|---|---|
| PALL FMP 130 | 100 | 47.7 | 52.1 |
| SAFC FMP 128 | 100 | 57.4 | 62.5 |

Without wishing to be bound by any theory, the higher integration ratios of microspheres synthesized with purer trisacryl and DEAE acrylamide may indicate that a better polymerization efficiency was achieved in the synthesis compared to microspheres with less pure materials.

Figure 5B:
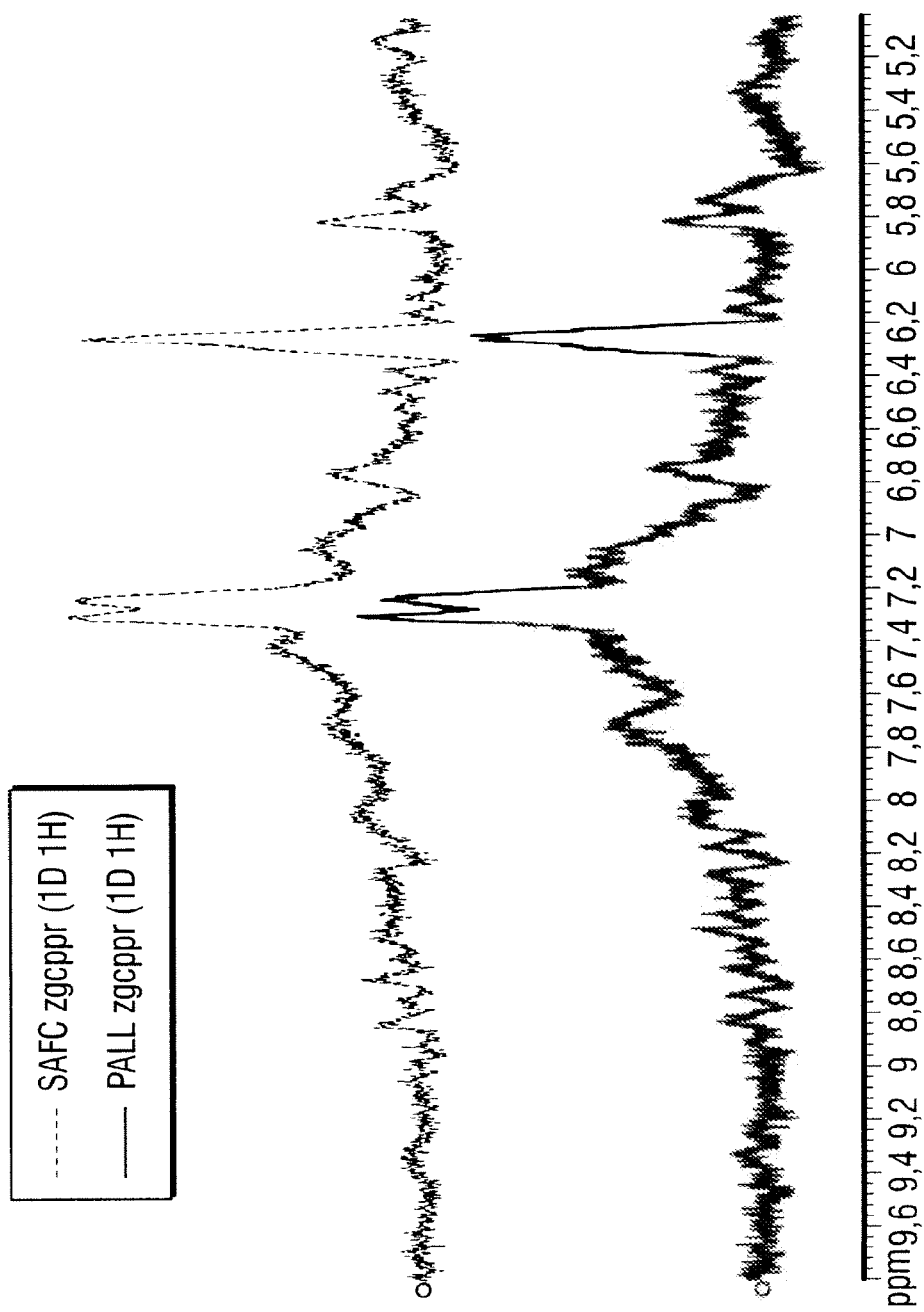
Figure 5D:
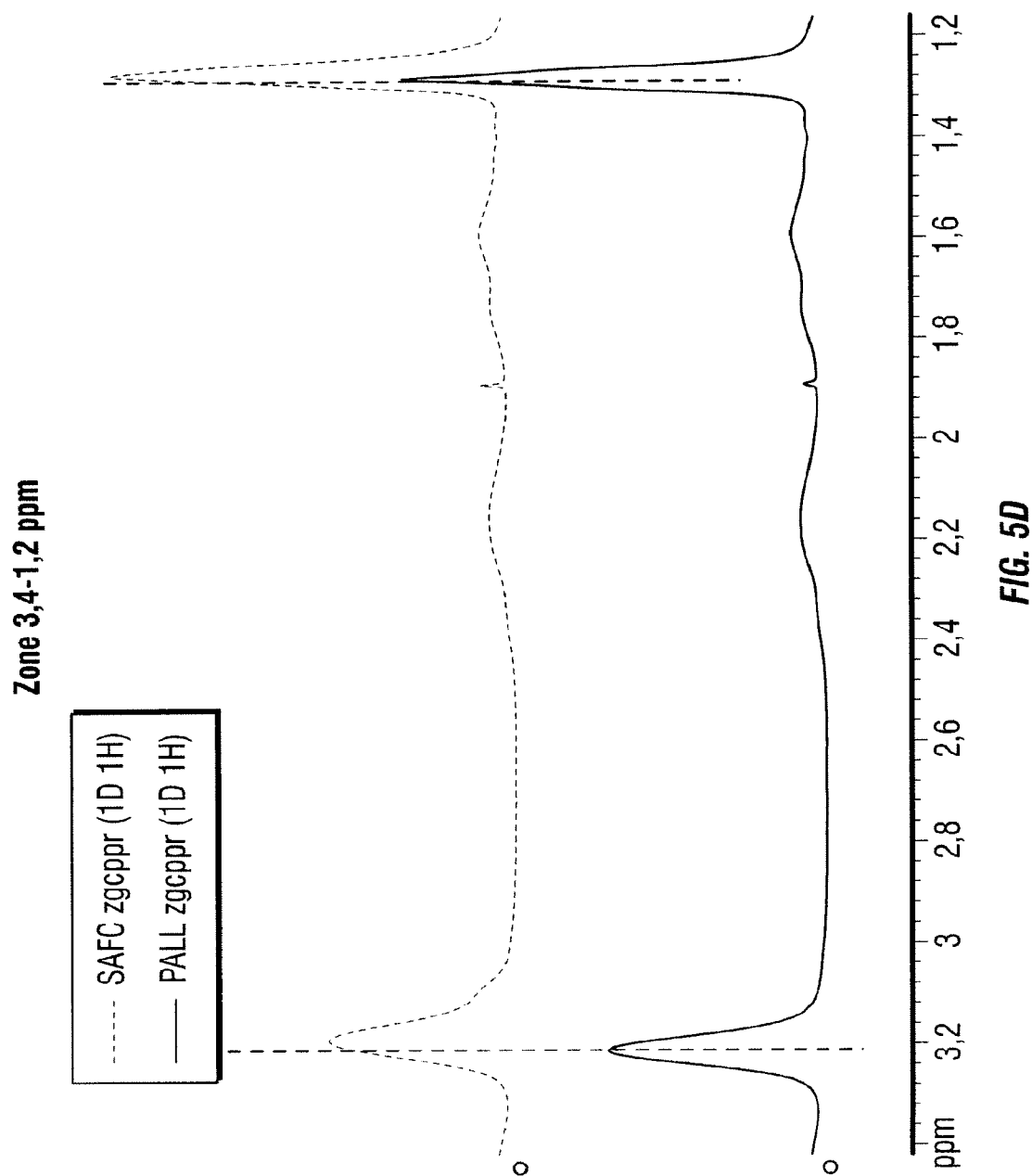
Figure 5F:
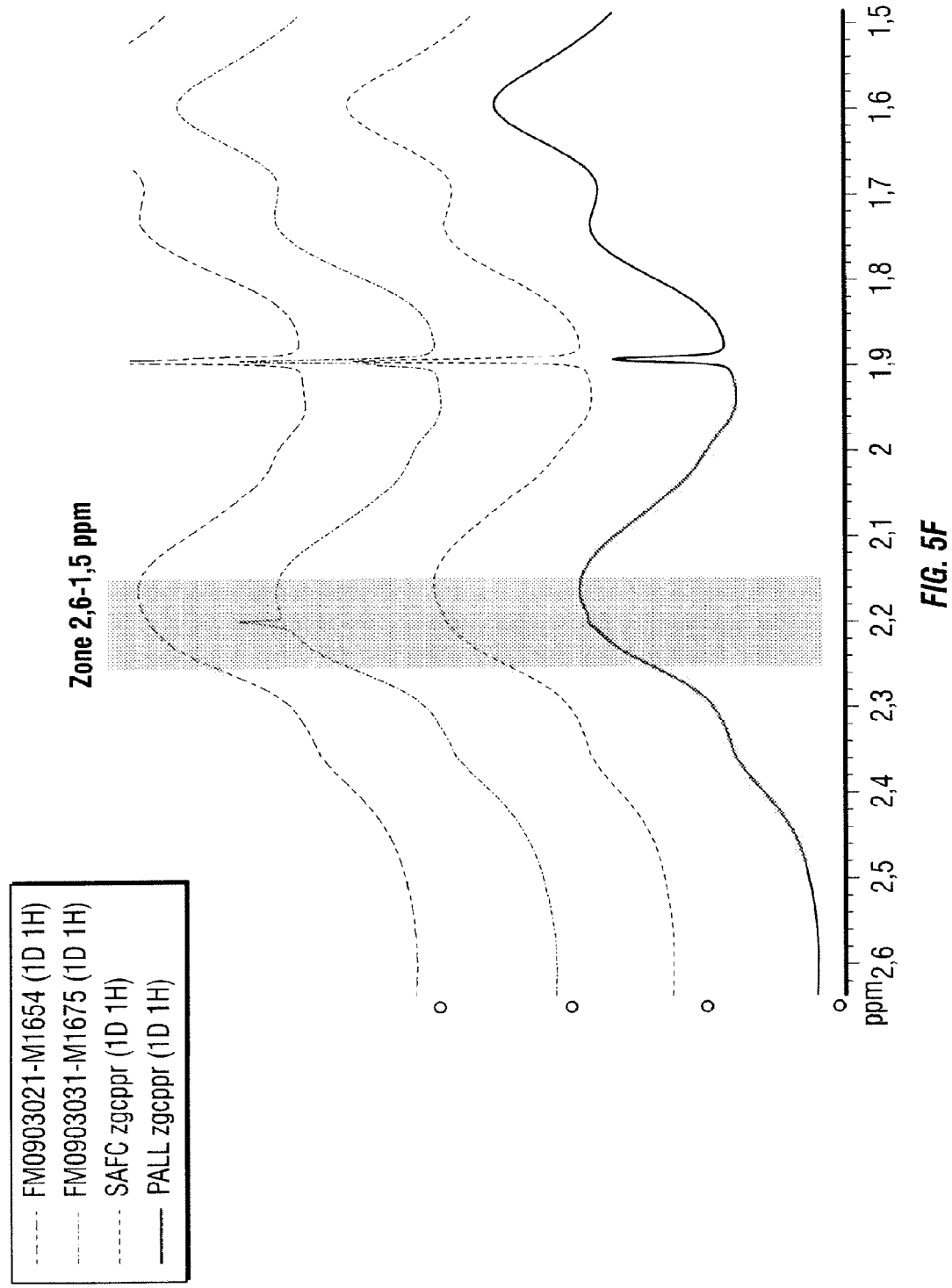

FIGS. 5B and 5C show the spectra in the regions of 9-5 ppm (5B) and 5-0 ppm (5C). Residual peaks were identified between 5 and 9 ppm, centered at 7.3 ppm, which may be attributed, for example, to the aromatic protons present in gelatin. Peaks between 6.4 and 5.8 ppm may be attributed, for example, to traces of excess acrylamide during the polymerization. FIG. 5O and Table 13 show the slight difference in the chemical shift (δ) for peaks B and C.

FIG. 5E shows a comparison of the $^1H$ NMR spectra of four different samples. A triplet at 1.15 ppm and a quadruplet at 3.62 ppm were identified from the FM0903031-M1675 and FM0903021-M1654 spectra. A singlet at 2.2 ppm was identified from the FM0903031-M1675 spectrum, which is also present in the SAFC 128 and PALL FMP 130 spectra but with much less intensity (See FIG. 5F).

Figure 5G:
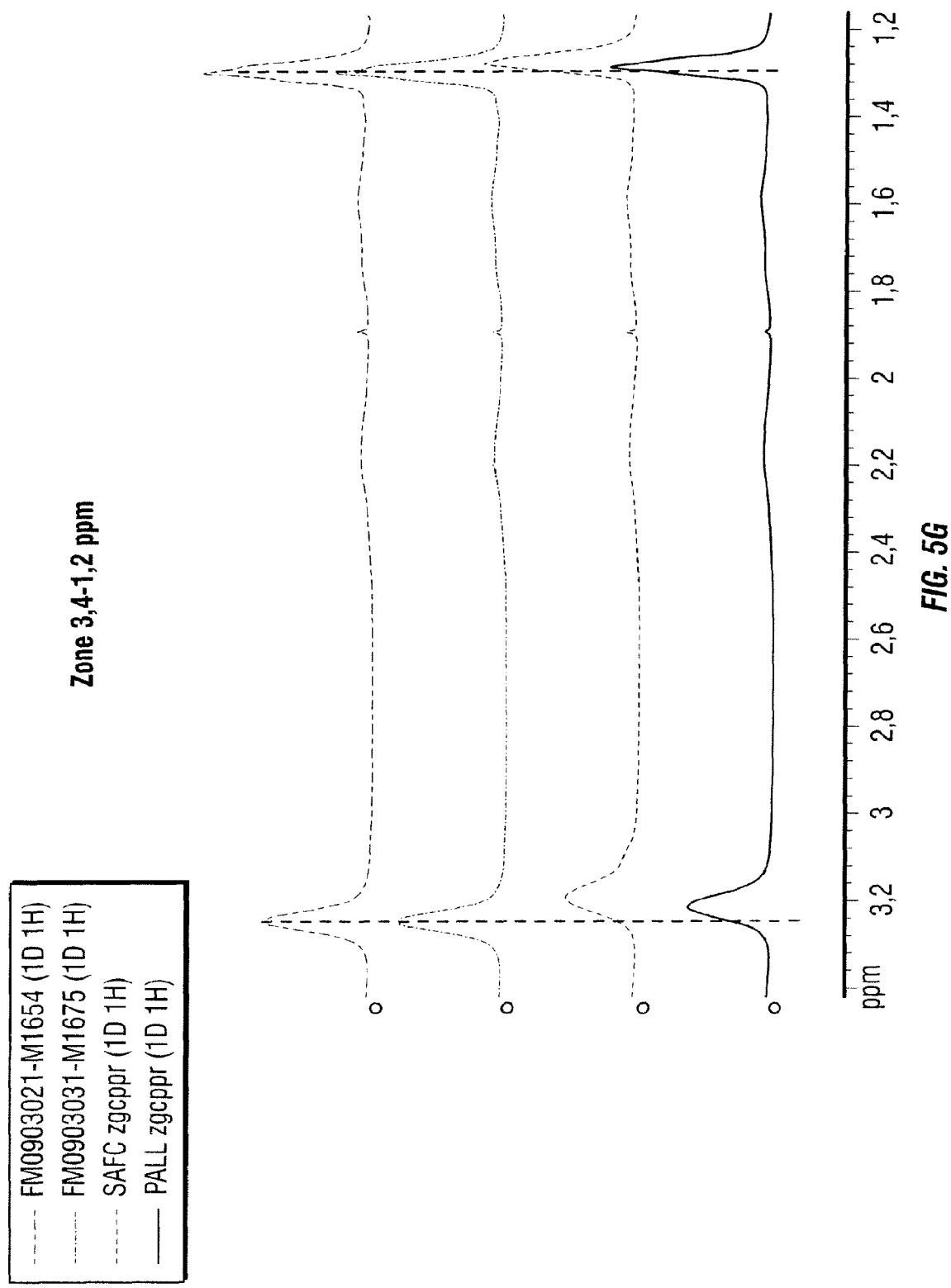

These resonance lines are relatively thin compared to the main peak, which may be due to the presence of small organic molecules. The triplet at 1.15 ppm and quadruplet at 3.62 ppm may be attributed, for example, to the presence of ethanol or ether diethyl. The chemical shifts of peaks B and C are identical for FM0903031-M1675 and FM0903021-M1654, which are different from PALL FMP 130 and SAFC FMP 128 (FIG. 5G). Table 14 summarizes the differences in the observed chemical shifts.

TABLE 14

| Sample | $δ_B$ (ppm) | $δ_C$ (ppm) | $Δ(δ_B)$ (Hz)* | $Δ(δ_C)$ (Hz)* |
|---|---|---|---|---|
| PALL FMP 130 | 3.212 | 1.284 | 0 | 0 |
| SAFC FMP 128 | 3.192 | 1.276 | 8.00 | 3.20 |
| FM0903031-M1675 | 3.246 | 1.298 | −13.60 | −5.60 |
| FM0903021-M1654 | 3.246 | 1.298 | −13.60 | −5.60 |

*Difference in Hz measured relative to the resonances of peaks B and C of the sample PALL FMP 130

Figure 5H:
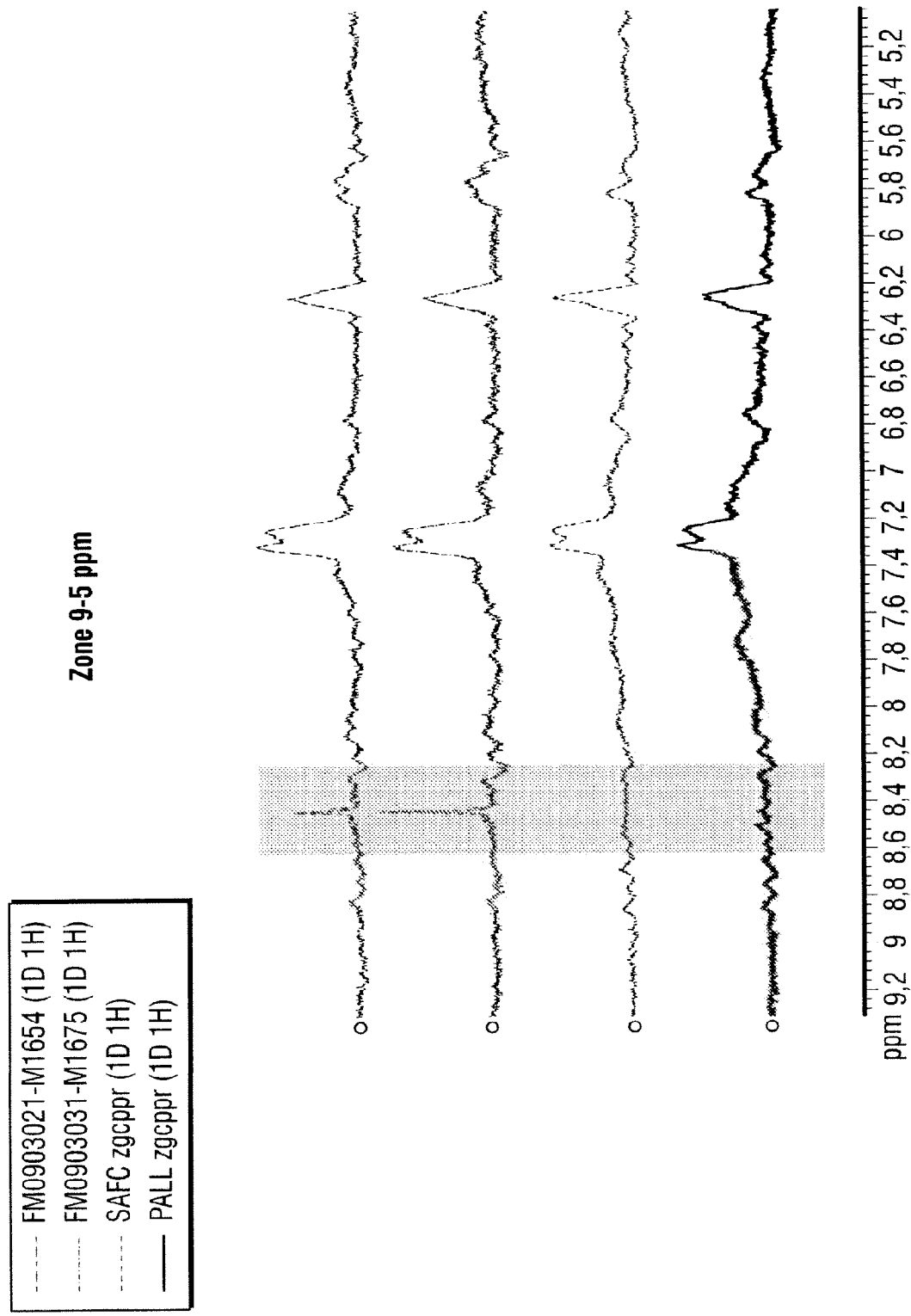
Figure 5I:
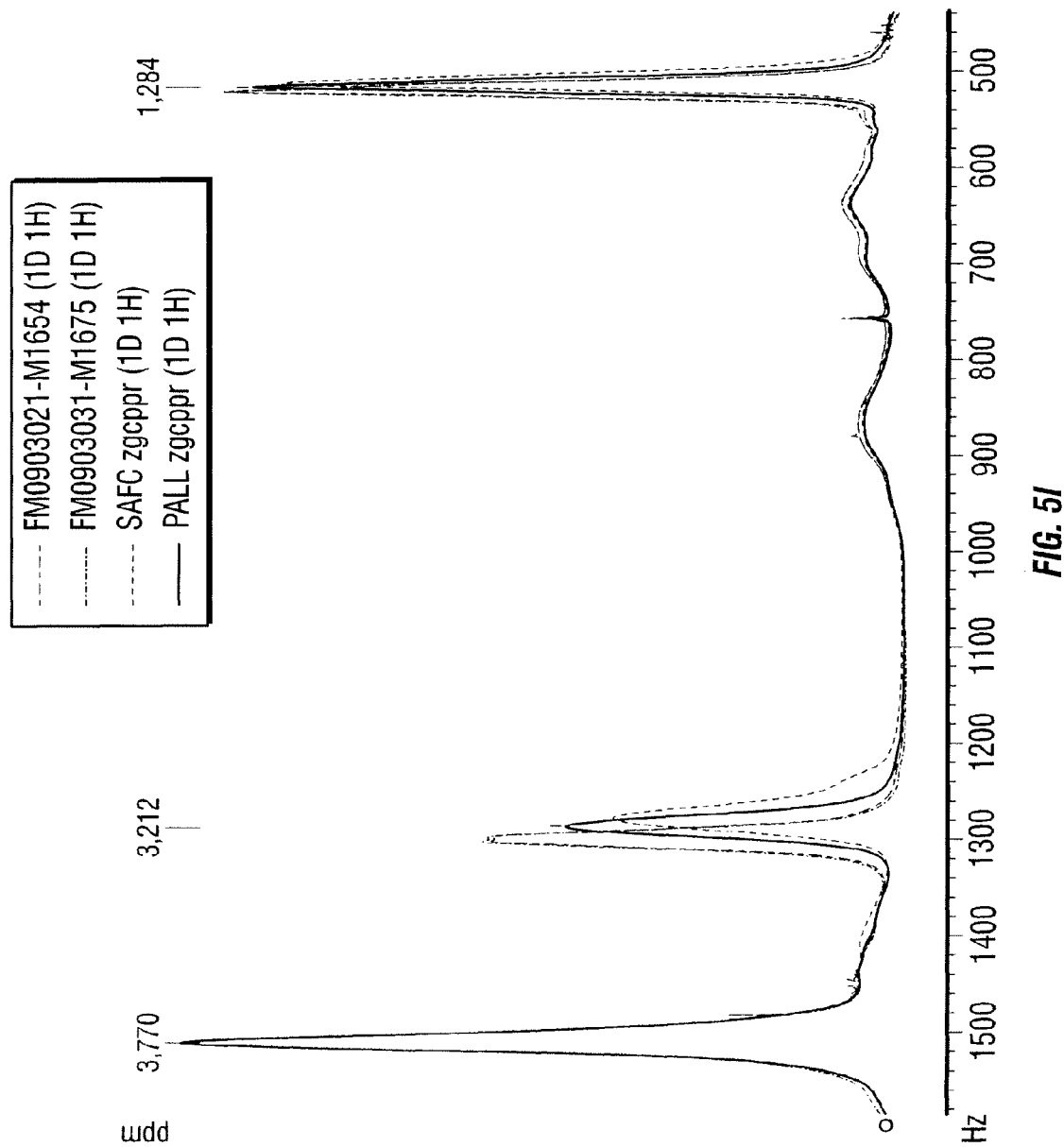
Figure 5J:
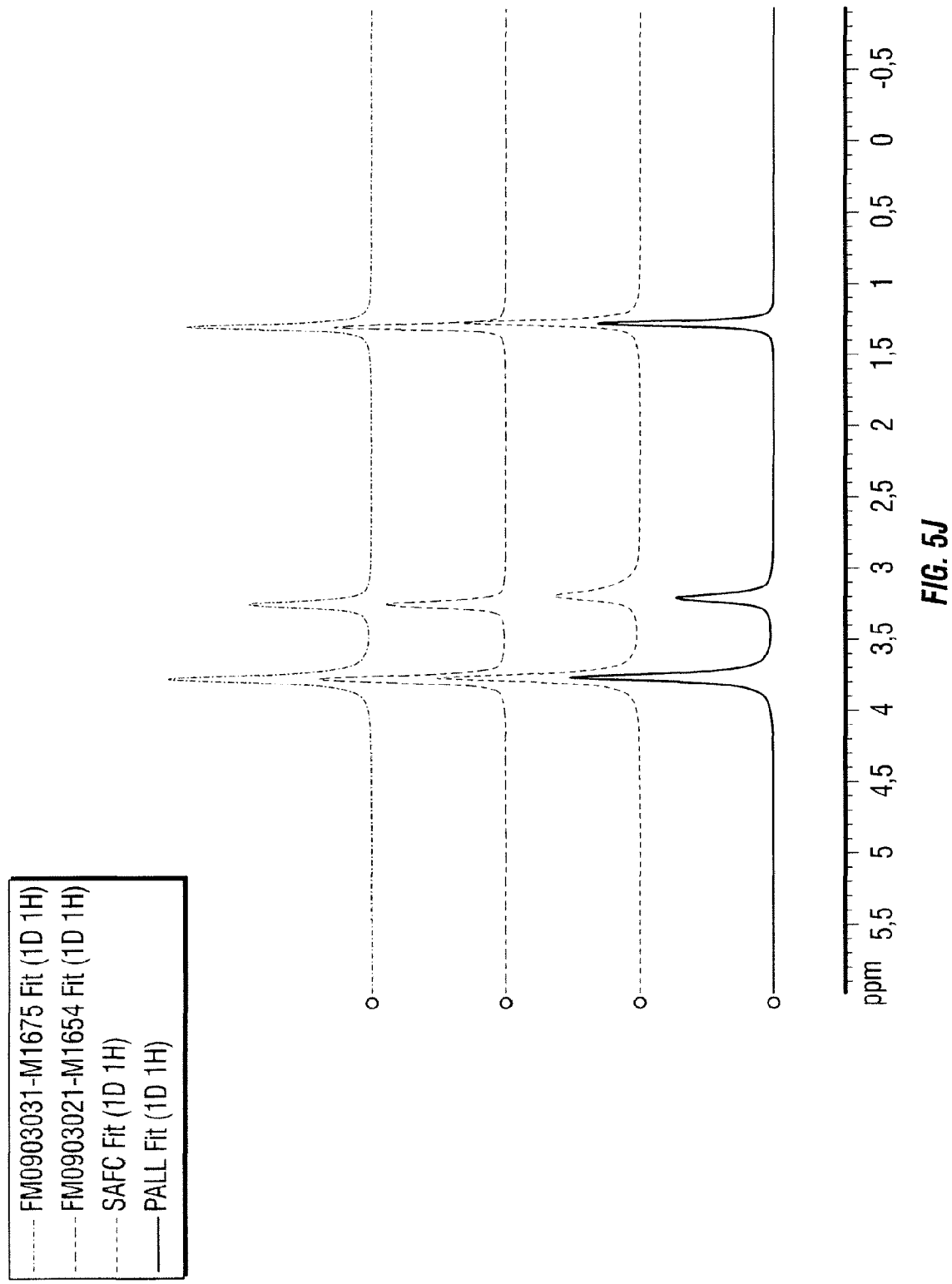

A peak located at 8.4 ppm was identified in the FM0903031-M1675 and FM0903021-M1654 spectra (FIG. 5H).

Semi-quantitative approach was employed to analyze the spectra. The superposition of the four spectra (FIG. 5I) illustrates the variations in the intensity and width at half height of peaks B and C. A deconvolution of mass A, B, and C was performed for each spectrum for quantification (FIG. 5J) using computer software. The amplitude values of peaks B and C calculated and normalized to the peak area A are summarized in Table 15.

TABLE 15

| Sample | A | B | C |
| --- | --- | --- | --- |
| PALL FMP 130 | 100 | 47.7 | 52.1 |
| SAFC FMP 128 | 100 | 57.4 | 62.50 |
| FM0903031-M1675 | 100 | 49.5 | 62.30 |
| FM0903021-M1654 | 100 | 49.7 | 60.90 |

Without wishing to be bound by any theory, the differences observed for peaks B and C among different samples can be explained, in part, as follows: Differences in the chemical shifts and widths at half height may be attributed to residual degrees of anisotropy between different samples. Even if the swelling in water combined with the rotation magic angle allows to average the anisotropy of displacement chemical and dipolar couplings, these effects are not completely canceled. These residual effects observable for the NMR spectra may be attributed to the degree of cross-linking in different samples. Different surfaces may be explained by the differences in the microstructure of the polymers. The differences in the presence or absence of small organic molecules may be explained by a difference in the manufacturing process or by a difference in the materials used. The differences in the chemical shift and width at half height observed for peaks B and C can be used to differentiate the sources of the samples.

Example 15

Administration of Microspheres in Patients with Liver Cancers

This study is carried out according to a modified procedure described in Xu et al. (2009) *World J Gastroenterol* 15(29): 3664-3669. Briefly, embolization (optionally TACE) is performed in patients after cross-sectional images are reviewed. A French vascular sheath is placed into the femoral artery, and a Mickaelson catheter is advanced into the celiac and superior mesenteric arteries. Contrast is injected into the arteries during rapid-sequence radiographic imaging. Arterial branches supplying the tumors are then located. The venous phase is carefully examined for patency of the portal veins. A Tracker catheter is advanced through the Mickaelson catheter to the arterial branches supplying the tumors. The mixture of doxorubicin (~50 mg), mitomycin (~10 mg), and lipiodol (~4-15 mL) is injected into the arterial branches until hemostasis was achieved. If the tumors have no shrinkage 2 weeks after the procedure, a second embolization can be performed.

The interventional radiologist then performs an arteriogram to identify the branches of the hepatic artery supplying the tumor(s) and threads smaller catheters into these branches. This is done to maximize the amount of the chemotherapeutic dose that is directed to the tumor.

When a blood vessel supplying tumor has been selected, microspheres alone or, in the case of TACE, alternating aliquots of the chemotherapy dose and of microspheres prepared according to Examples 7 or 8 (or other microsphere provided herein), or microspheres in combination with the chemotherapy agent, are injected through the catheter. The total microsphere and/or chemotherapeutic dose may be given in one vessel's distribution, or it may be divided among several vessels supplying the tumor(s).

Example 16

Administration of Microspheres in Patients with Prostate Cancer

Patients diagnosed with prostate cancer are divided up into two groups, a test group and a control group. Patients from the test group are treated with embolization, using microspheres prepared according to Example 7 or 8 (or other microspheres provided herein).

Biopsies are performed in patients with visible prostate tumors. Patients whose prostate tumors are diagnosed to be caners are treated with embolization. Before treatment, sizes of the prostate cancer tumors and levels of the blood PSA in patients having the prostate cancer tumors are recorded.

Prior to the embolization procedure, a prophylactic single dose of 200 mg ciprofloxacin is given. Intervention is performed under local anesthesia through the right trans-femoral approach. Initial pelvic angiography is performed to evaluate the iliac vessels and prostate arteries during the arterial and late phases. Selective digital subtraction angiography of the right and left internal iliac arteries is performed using a 5-Fr Cobra 2 catheter to better assess the blood supply to the prostate. Superselective catheterization of the right and left inferior vesicle arteries is then performed using a microcatheter (Embocath; Biosphere Medical, Rockland, Me., USA) and angiography is performed by manually injecting 3-5 ml of contrast medium to ensure that the tip of the microcatheter is inside or at the ostium of the prostatic arteries. Microspheres prepared according to Examples 7 or 8 are calibrated to 300-500 µm in diameter are used for embolization. Each 2-ml vial of microspheres is diluted in a mixture of 20 ml of 50% iodinated contrast medium plus 50% normal saline solution. The mixture is slowly injected under fluoroscopic guidance. Embolization of the prostate arteries arising from the inferior vesical arteries is performed to stasis without reflux of the mixture to undesired arteries. Follow-up angiography is performed manually with the microcatheter at the inferior vesical artery and using the pump with the 5-Fr catheter at the anterior branch of the internal iliac artery checking any further blood supply to the prostate. Embolization is then performed on the other side using the same technique.

Weekly measurements of the tumor size are recorded. Tumor volume is calculated (tumor volume=0-5 (L+W)×L× W×0.5236, where L=tumor length and W=width). The tumor volume at the time of embolization is served as the point of reference for future comparison of that tumor's size variation. The weekly variations of each tumor volume are recorded as percent differentiation from the original measurement at embolization. The blood PSA levels are followed and compared with the levels at the time of embolization.

Example 17

Administration of Microspheres in Patients with Arteriovenous Malformation

Patients with brain arteriovenous malformations (BAVM) receive embolization according to a modified procedure described Gao et al. (2009) *Chinese Medical Journal* 122 (16):1851-1856. Briefly, embolization is carried out under general anesthesia without systemic heparinization. During the procedure, systolic blood pressure is controlled between 100 and 110 mmHg. Catheterization is performed using a transfemoral approach with standard coaxial techniques. The guiding catheter is flushed via a pressure bag with saline containing 2500 U heparin/L. Navigation of a DMSO-compatible microcatheter (UltraFlow or Marathon; ev3; USA) to the target is performed with a combination of flow-guided and wire-guided techniques using a 0.010-inch or a 0.008-inch wire (Silverspeed or Mirage; ev3; USA). Once the microcatheter tip is in the desired position, the injection of microspheres prepared according to Example 7 or 8 (or other microspheres provided herein) is carried out as follows: 1) the microcatheter is flushed with 5 ml normal saline; 2) 0.25 ml DMSO is injected into the microcatheter to fill the dead space; 3) microspheres aspirated into a 1 ml syringe, and 0.25 ml of this amount is injected over for 40 seconds to fill the microcatheter and to replace the DMSO in the dead space; 4) slow injection of the microsphere solution is then continued under fluoroscopy.

After embolization, patient blood pressure is strictly monitored for 48 hours in the intensive care unit. In rare event the microcatheter sticking in the arterial feeder, heparin is intravenously administered (750-1000 U/hour) for 72 hours, followed by oral aspirin for 3 months at a dose of 250 mg/d. The BAVM nidus size is then monitored by yearly MRI. If after three years the AVM is still not obliterated, radiosurgery is considered.

Example 18

Administration of Microspheres in a Porcine Model of a Benign Prostatic Hyperplasia The study is carried out according to a modified procedure described in Sun et al. (2008) *Radiology* 246: 783-789. Briefly, pigs are randomly assigned to the embolization group or the control group. After fasting for 24 hours, all male pig are each premedicated with 0.1 mg of diazepam per kilogram of body weight, 10 mg/kg ketamine, and 0.01 mg/kg atropine intramuscularly. Anesthesia is initiated with 2 mg/kg propofol (i.v.) and maintained with 2.0%-2.5% halothane. Each pig is connected to an anesthesia system and a mechanical ventilator after endotracheally intubated. The groin area and lower abdomen were shaved and draped in a sterile manner.

Femoral arterial access is gained percutaneously with a 5-F introducer sheath. Pelvic angiography is performed, a 5-F Cobra catheter is inserted into the aorta and the catheter tip is shaped into a Waltman loop from the contralateral external iliac artery. With road map guidance, selective catheterization to the internal iliac artery on both sides is achieved. Angiography is performed in the two arteries. The control group animals then recovered from anesthesia.

Selective embolization of the prostate is performed in the embolization group. After the systemic distribution of heparin (150 IU of heparin/kilogram of body weight), a 3-F infusion catheter is inserted coaxially through the Cobra catheter and selectively placed in the prostatic branch of the inferior vesical artery. Superselective angiography is performed by manually injecting 1 mL of contrast medium to ensure that the tip of the microinfusion catheter is at the desired site. Microspheres prepared according to Example 7 or 8 (or other microspheres provided herein) are calibrated to 500-700 µm in diameter. Each vial of microspheres, containing 2.0 mL of microsphere particles, is diluted in a mixture of 20 mL of 50% iodinated contrast medium plus 50% normal saline solution. The mixture is slowly injected with fluoroscopic guidance. Embolization is immediately terminated once hemostasis is achieved without reflux of the mixture to undesired arteries. Follow-up angiography is performed. Subsequently, embolization is performed on the other side by using the same technique. The animals are allowed to recover from anesthesia under care. After embolization, all animals are checked twice a day for 72 hours and then once daily for 1 week for possible complications associated with embolization.

Example 19

Administration of Microspheres in Patients with Uterine Fibroids

Uterine artery embolization (UAE) is carried out according to a modified procedure described in Pelage et al. (2000) *Radiology* 215:428-431. Briefly, UAE is performed by an interventional radiologist and involves complete occlusion of either one or both uterine arteries with particulate emboli to cause ischaemic necrosis of the uterine fibroids. The closure of the arteries is considered permanent, thereby blocking blood supply to the fibroid but without any permanent adverse effect on the otherwise normal uterus. UAE is performed under local anaesthetic, sometimes with conscious sedation, epidural or spinal anaesthetic. Prophylactic antibiotics may also be administered. A vascular sheath of 4 or 5 French diameter is inserted directly into the woman's femoral artery and the contralateral uterine artery is then selectively catheterised. The catheter may then be manoeuvred to the ipsilateral uterine artery and the process repeated.

In this study, microspheres prepared according to Example 7 or 8 (or other microspheres provided herein) are calibrated to 700-900 µm in diameter and administered. Occlusion of the uterine vessels is confirmed by angiography and the catheter removed. The woman is exposed to approximately 20 rad (20cGy) of ionizing radiation to the ovaries. Successful UAE totally occludes both uterine vessels. The normal myometrium (muscle of the womb) rapidly establishes a new blood supply through collateral vessels from the ovarian and the vaginal circulations.

The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "a microsphere" includes a mixture of two or more such microspheres. Additionally, ordinarily skilled artisans will recognize that operational sequence must be set forth in some specific order for the purpose of explanation and claiming, but the present invention contemplates various changes beyond such specific order.

What is claimed is:

1. A method of making microspheres, comprising:
preparing an aqueous solution comprising:
(i) a N-tris-hydroxymethyl methylacrylamide monomer,
(ii) a diethylaminoethylacrylamide monomer,
(iii) a N,N-methylene-bis-acrylamide monomer, and
(iv) gelatin;
adding the aqueous solution into a liquid organic phase that has low miscibility in water using a feed system, before or while stirring; thereby producing microspheres comprising a copolymer comprising a N-tris-hydroxymethyl methylacrylamide monomer unit, a diethylaminoethylacrylamide monomer unit and a N,N-methylene-bis-acrylamide monomer unit; wherein the feed system comprises feed equipment that is disposed in the liquid organic phase, and wherein the aqueous solution is passed through the feed equipment and infected into the liquid organic phase; and crosslinking the gelatin.

2. The method of claim 1, wherein the feed system comprises feed ring equipment that is placed in the liquid organic phase, and wherein the step of adding the aqueous solution into the liquid organic phase comprises passing the aqueous solution through the feed ring equipment into the liquid organic phase.

3. The method of claim 1, wherein the feed system comprises a longitudinal axis and a plurality of spaced fingers extending outward from a cross-member connected to the longitudinal axis.

4. The method of claim 2, wherein the feed system comprises a first pump and a second pump, wherein the aqueous solution is injected through the first pump into the feed ring equipment and wherein an aqueous ammonium persulfate solution is injected through the second pump into the feed ring equipment.

5. The method of claim 4, wherein the aqueous solution is injected through the first pump into the feed ring equipment and the aqueous ammonium persulfate solution is injected through the second pump into the feed ring equipment simultaneously.

6. The method of claim 1, further comprising:

subjecting the microspheres to ultrasonication.

7. The method of claim 6, wherein the step of subjecting the microspheres to ultrasonication occurs prior to the step of crosslinking the gelatin.

8. The method of claim 1, wherein the method does not comprise sieving the microspheres.

9. The method of claim 1, wherein the liquid organic phase has 15% or less miscibility in water at 25° C.

10. The method of claim 1, wherein the liquid organic phase comprises an oil.

11. The method of claim 1, wherein the N-tris-hydroxymethyl methylacrylamide monomer comprises less than 9% of impurities and/or the diethylaminoethylacrylamide monomer comprises less than 2% of impurities.

12. The method of claim 1, wherein (i) the microspheres comprise about 10% or less, 9% or less, 8% or less, 7% or less, 6% or less, 5% or less, 4% or less, 3% or less, 2% or less or 1% or less of impurities, (ii) the microspheres comprise 90% or more, 91% or more, 92% or more, 93% or more, 94% or more, 95% or more, 96% or more, 97% or more, 98% or more or 99% or more by weight of the N-tris-hydroxymethyl methylacrylamide, the diethylaminoethylacrylamide, the N,N-methylene-bis-acrylamide and the gelatin, or (iii) a combination of (i) and (ii).

13. The method of claim 1, wherein the microspheres exhibit in a $^1$H NMR spectrum, a first peak from about 3.5 ppm to about 4 ppm, a second peak from about 3 ppm to about 3.5 ppm, and a third peak from about 1 ppm to about 1.5 ppm; and wherein (i) the integration ratio of the second peak to the first peak is from 0.50 to about 0.65, (ii) the integration ratio of the third peak to the first peak is from 0.61 to about 0.75, or (iii) a combination thereof.

14. The method of claim 1, wherein the microspheres have a diameter from about 1 μm to about 2000 μm, from 40 μm to about 120 μm, from about 100 μm to about 300 μm, from about 300 μm to about 500 μm, from about 500 μm to about 700 μm, from about 700 μm to about 900 μm, or from about 900 μm to about 1200 μm.

15. The method of claim 1, wherein less than 1% of the microspheres are aggregated microspheres.

16. A method of making microspheres, comprising:

preparing an aqueous solution comprising:

(i) a N-tris-hydroxymethyl methylacrylamide monomer, (ii) a diethylaminoethylacrylamide monomer, (iii) a N,N-methylene-bis-acrylamide monomer, and (iv) gelatin;

adding the aqueous solution into a liquid organic phase that has low miscibility in water using a feed system, before or while stirring; thereby producing microspheres comprising a copolymer comprising a N-tris-hydroxymethyl methylacrylamide monomer unit, a diethylaminoethylacrylamide monomer unit and a N,N-methylene-bis-acrylamide monomer unit; wherein the feed system comprises a longitudinal axis and a plurality of spaced fingers extending outward from a cross-member connected to the longitudinal axis, wherein the aqueous solution is passed through the feed system and injected into the liquid organic phase; and crosslinking the gelatin.

17. The method of claim 16, further comprising:

subjecting the microspheres to ultrasonication.

18. The method of claim 17, wherein the step of subjecting the microspheres to ultrasonication occurs prior to the step of crosslinking the gelatin.

19. The method of claim 16, wherein the method does not comprise sieving the microspheres.

20. The method of claim 16, wherein the liquid organic phase has 15% or less miscibility in water at 25° C.

21. The method of claim 16, wherein the liquid organic phase comprises an oil.

22. A method of making microspheres, comprising:

preparing an aqueous solution comprising:

(i) a N-tris-hydroxymethyl methylacrylamide monomer, (ii) a diethylaminoethylacrylamide monomer, (iii) a N,N-methylene-bis-acrylamide monomer, and (iv) gelatin;

adding the aqueous solution into a liquid organic phase that has low miscibility in water using a feed system, before or while stirring; thereby producing microspheres comprising a copolymer comprising a N-tris-hydroxymethyl methylacrylamide monomer unit, a diethylaminoethylacrylamide monomer unit and a N,N-methylene-bis-acrylamide monomer unit; wherein the feed system comprises feed ring equipment, wherein the aqueous solution is passed through the feed ring equipment and into the liquid organic phase; and crosslinking the gelatin.

23. The method of claim 22, further comprising:

subjecting the microspheres to ultrasonication.

24. The method of claim 22, wherein the liquid organic phase comprises an oil.

* * * * *

UNITED STATES PATENT AND TRADEMARK OFFICE
CERTIFICATE OF CORRECTION

PATENT NO. : 9,439,861 B2  
APPLICATION NO. : 13/890038  
DATED : September 13, 2016  
INVENTOR(S) : Philippe Reb et al.

Page 1 of 1

It is certified that error appears in the above-identified patent and that said Letters Patent is hereby corrected as shown below:

In the Claims

Column 65, Line 2 reads, ". . . and infected into the liquid . . ." which should read ". . . and injected into the liquid . . ."

Signed and Sealed this  
Twenty-first Day of February, 2017

Michelle K. Lee  
*Director of the United States Patent and Trademark Office*